(12) United States Patent
Chene et al.

(10) Patent No.: US 11,147,868 B2
(45) Date of Patent: Oct. 19, 2021

(54) IMMUNOGENIC CONSTRUCT COMPRISING AN EBV-CELL ANTIGEN AND A TARGETING MOIETY AND APPLICATIONS THEREOF

(71) Applicants: Institut National de la Sante et de la Recherche Medicale (INSERM), Paris (FR); Centre National de la Recherche Scientifique (CNRS), Paris (FR); Universite de Paris, Paris (FR); Institut National Transfusion Sanguine, Paris (FR)

(72) Inventors: Arnaud Chene, Paris (FR); Benoit Gamain, Plaisir (FR); Stéphane Gangnard, Paris (FR)

(73) Assignees: Institut National de la Sante et de la Recherche Medicale (INSERM), Paris (FR); Centre National de la Recherche Scientifique (CNRS), Paris (FR); Université de Paris, Paris (FR); Institut National Transfusion Sanguine, Paris (FR)

(*) Notice: Subject to any disclaimer, the term of this patent is extended or adjusted under 35 U.S.C. 154(b) by 0 days.

(21) Appl. No.: 16/061,807

(22) PCT Filed: Dec. 15, 2016

(86) PCT No.: PCT/EP2016/081309
§ 371 (c)(1),
(2) Date: Jun. 13, 2018

(87) PCT Pub. No.: WO2017/103020
PCT Pub. Date: Jun. 22, 2017

(65) Prior Publication Data
US 2018/0360950 A1    Dec. 20, 2018

(30) Foreign Application Priority Data

Dec. 15, 2015 (EP) .................................... 15307014

(51) Int. Cl.
| | |
|---|---|
| *A61K 39/245* | (2006.01) |
| *C07K 16/28* | (2006.01) |
| *A61K 39/25* | (2006.01) |
| *C12N 7/00* | (2006.01) |
| *C07K 16/20* | (2006.01) |
| *A61K 39/00* | (2006.01) |

(52) U.S. Cl.
CPC ............ *A61K 39/245* (2013.01); *A61K 39/25* (2013.01); *C07K 16/205* (2013.01); *C07K 16/28* (2013.01); *C07K 16/2887* (2013.01); *C07K 16/2896* (2013.01); *C12N 7/00* (2013.01); *A61K 2039/572* (2013.01); *A61K 2039/585* (2013.01); *A61K 2039/60* (2013.01); *A61K 2039/6025* (2013.01); *A61K 2039/6031* (2013.01); *A61K 2039/6056* (2013.01); *A61K 2039/6087* (2013.01); *C07K 2317/569* (2013.01); *C07K 2317/622* (2013.01); *C07K 2317/732* (2013.01); *C07K 2317/92* (2013.01); *C07K 2319/01* (2013.01); *C07K 2319/30* (2013.01); *C07K 2319/74* (2013.01); *C12N 2710/16211* (2013.01); *C12N 2710/16234* (2013.01); *C12N 2710/16271* (2013.01); *Y02A 50/30* (2018.01)

(58) Field of Classification Search
None
See application file for complete search history.

(56) References Cited

FOREIGN PATENT DOCUMENTS

| | | |
|---|---|---|
| DE | 103 07 517 A1 | 9/2004 |
| JP | 2013/535508 A | 9/2013 |
| JP | 2015/516376 A | 6/2015 |
| WO | WO 2007/060192 | 5/2007 |
| WO | WO-2012-021834 A1 | 2/2012 |
| WO | WO-2013-139789 A1 | 9/2013 |

OTHER PUBLICATIONS

Gen Bank Accession YP_001129448, (2010), BFRF3 [Human herpesvirus 4 type 2].*
Gen Bank Accession YP_401651, (2013), capsid protein VP26 [Human herpesvirus 4].*
Aird et al., Plasmodium falciparum *picks (on)* EPCR, 123(2) Blood 163-167 (Nov. 18, 2013).
Birch et al., *Identification of malaria parasite-infected red blood cell surface aptamers by inertial microfluidic SELEX (I-SELEX)*, 5(11347) Scientific Reports 1-16 (2015).
Chan et al., *A Simplified, Sensitive Phagocytic Assay for Malaria Cultures Facilitated by Flow Cytometry of Differentially-Stained Cell Populations*, 7(6) PLoS ONE 1-10 (Jun. 2012).
Chen et al., *Fusion Protein Linkers: Property, Design and Functionality*, 65(10) Adv. Drug Delivery Review 1357-1369 (Oct. 15, 2013).
Clausen et al., *Structural and Functional Insight into How the Plasmodium falciparum VAR2CSA Protein Mediates Binding to Chondroitin Sulfate in a Placental Malaria*, 287(28) Journal of Biological Chemistry 23332-23345 (Jul. 6, 2012).

(Continued)

*Primary Examiner* — Benjamin P Blumel
(74) *Attorney, Agent, or Firm* — Panitch Schwarze Belisario & Nadel LLP

(57) ABSTRACT

The present invention generally relates to an immunogenic construct, useful for redirecting an EBV-existing immune response towards an undesired target cell and/or microorganism, to methods for preparing said conjugate, to a pharmaceutical applications comprising said conjugate, and to medical applications thereof.

16 Claims, 22 Drawing Sheets
Specification includes a Sequence Listing.

(56) References Cited

OTHER PUBLICATIONS

Conrath et al., *Antigen Binding and Solubility Effects upon the Veneering of a Camel VHH in Framework-2 to Mimic a VH*, 350 J. Mol. Biol. 112-125 (2005).

Estévez et al., *Nanoparticle-Aptamer Conjugates for Cancer Cell Targeting and Detection*, 624 Cancer Nanotechnology, Methods in Molecular Biology 235-248 (2010).

Eudes et al., *A generalized analysis of hydrophobic and loop clusters within globular protein sequences*, 7(2) BMC Structural Biology 1-22 (Jan. 8, 2007).

Gurer et al., *Targeting the nuclear antigen 1 of Epstein-Barr virus to the human endocytic receptor DEC-205 stimulates protective T-cell responses*, 112(4) Blood (Aug. 15, 2008).

Harboe et al., *Advances in assay of complement function and activation*, 63 Advanced Drug Delivery Reviews 976-987 (2011).

Hu et al., *A flexible peptide linker enhances the immunoreactivity of two copies HBsAg preS1 21-47 fusion protein*, 107 Journal of Biotechnology 83-90 (2004).

Hu et al., *Identification of the immunogenic domains in HBsAg preS1 region using overlapping pres 1 fragment fusion proteins*, 11(14) World Journal of Gastroenterology 2088-2094 (2005).

Jiang et al., *Advances in the assessment and control of the effector functions of therapeutic antibodies*, 10 Nature Reviews 101-110 (Feb. 2011).

Kalland et al., *Targeting of superantigens*, 22 Cell Biophysics 147-164 (1993).

Lambert et al., *Antigen Reversal Identifies Targets of Opsonizing IgGs against Pregnancy-Associated Malaria*, 82(11) Infection and Immunity 4842-4853 (Nov. 2014).

Liu et al., *Production of a Mouse-Human Chimeric Monoclonal Antibody to CD20 with Potent Fc-Dependent Biologic Activity*, 139(10) The Journal of Immunology 3521-3256 (Nov. 15, 1987).

Nunes-Silva et al., *Llama immunization with full-length VAR2CSA generates cross-reactive and inhibitory single-domain antibodies against the DBL1X domain*, 4(7373) Scientific Reports 1-9 (2014).

Olafsen et al., *Recombinant anti-CD20 antibody fragments for microPET imaging of B-cell lymphoma*, 50(9) J. Nucl. Med 1500-1508 (Sep. 2009).

Otz et al., *A bispecific single-chain antibody that mediates target cell-restricted, supra-agonistic CD28 stimulation and killing of lymphoma cells*, 23 Leukemia 71-77 (2009).

Škrlec et al., *Non-immunoglobulin scaffolds: a focus on their targets*, 33(7) Trends in Biotechnology 1-11 (2015).

Smolarek et al., *A recombinant dromedary antibody fragment (VHH or nanobody) directed against human Duffy antigen receptor for chemokines*, 67 Cell. Mol. Life. Sci. 3371-3387 (2010).

Srivastava et al., *Var2CSA Minimal CSA Biding Region Is Located within the N-Terminal Region* 6(5) PLoS ONE 1-10 (May 2011).

Stoltenburg et al., *SELEX—A (r)evolutionary method to generate high-affinity nucleic acid ligands*, 24 Biomolecular Engineering 381-403 (2007).

Sundström et al., *Antibodies to specific EBNA-1 domains and HLA DRB1*1501 interact as risk factors for multiple sclerosis*, 215 Journal of Neurommunology 102-107 (2009).

Vogt et al., *Heparan sulfate on endothelial cells mediates the binding of Plasmodium falciparum—infected erythrocytes via the DBL1α domain of PfEMP1*, 101 (6) Blood 2405-2411 (Mar. 2003).

Wu et al., *Targeting Hepatocytes for Drug and Gene Delivery: Emerging Novel Approaches and Applications*, 7 Frontiers in Bioscience d717-d725 (Mar. 1, 2002).

Zeicke et al., *Utilizing the folate receptor for active targeting of cancer nanotherapeutics*, 3 Nano Reviews 1-11 (2012).

Kristian et al., *Retargeting pre-existing human antibodies to a bacterial pathogen with an alpha-Gal conjugated aptamer*, 93 J. Mol. Med 619-631 (2015).

Thompson et al., *Epstein-Barr Virus and Cancer*, 10 Clinical Cancer Research 803-821 (Feb. 1, 2004).

\* cited by examiner

FIGURE 3

| Construct | Ka (1/Ms) | Kd (1/s) | $K_D$ M |
|---|---|---|---|
| $DARC_{VHH}$ | 2.126E+7 | 0.001915 | 9.00 E-11 |
| $DARC_{VHH}$-EBV P18F2 | 1.374E+9 | 0.03781 | 2.75 E-11 |
| $DARC_{VHH}$-EBV P18F3 | 2.969E+7 | 0.002202 | 7.42 E-11 |
| $DARC_{VHH}$-EBV P18F4 | 1.363E+7 | 7.698E-4 | 5.65 E-11 |
| $VAR2CSA_{VHH}$ | 3.298E+5 | 1.602E-4 | 4.86 E-10 |
| $VAR2CSA_{VHH}$-EBV P18F2 | 4.540E+4 | 3.288E-4 | 7.24  E-9 |
| $VAR2CSA_{VHH}$-EBV P18F3 | 3.032E+5 | 1.674E-4 | 5.52 E-10 |

FIGURE 5

|  a  |  b  |  c  |
|---|---|---|
| PBS<br>PBS<br>PBS | PBS<br>PBS<br>Anti-hIgG (Fab)$_2$ | DARC$_{VHH}$-EBV P18F3<br>PBS<br>Anti-hIgG (Fab)$_2$ |
| DARC$_{VHH}$-EBV P18F3<br>Plasma 1/3<br>Anti-hIgG (Fab)$_2$ | DARC$_{VHH}$-EBV P18F3<br>Plasma 1/6<br>Anti-hIgG (Fab)$_2$ | DARC$_{VHH}$-EBV P18F3<br>Plasma 1/12<br>Anti-hIgG (Fab)$_2$ |
|  d  |  e  |  f  |

FIGURE 8B

SEQUENCE LISTING

<160> NUMBER OF SEQ ID NOS: 86

<210> SEQ ID NO 1
<211> LENGTH: 1
<212> TYPE: PRT
<213> ORGANISM: artificial
<220> FEATURE:
<223> OTHER INFORMATION: polyproline linker (can be repeated between 2
      and 8, inclusive)

<400> SEQUENCE: 1

Pro
1

<210> SEQ ID NO 2
<211> LENGTH: 1
<212> TYPE: PRT
<213> ORGANISM: artificial
<220> FEATURE:
<223> OTHER INFORMATION: polyglycine linker (can be repeated between 6
      and 8, inclusive)

<400> SEQUENCE: 2

Gly
1

<210> SEQ ID NO 3
<211> LENGTH: 5
<212> TYPE: PRT
<213> ORGANISM: artificial
<220> FEATURE:
<223> OTHER INFORMATION: glycine-serine linker (can be repeated between
      2 and 5, inclusive)

<400> SEQUENCE: 3

Gly Gly Gly Gly Ser
1               5

<210> SEQ ID NO 4
<211> LENGTH: 7
<212> TYPE: PRT
<213> ORGANISM: artificial
<220> FEATURE:
<223> OTHER INFORMATION: Alpha-helix-forming linker A(EAAAK)nA (amino
      acid sequence from position 2 to position 6 can be repeated
      between 2 and 5, inclusive)

<400> SEQUENCE: 4

Ala Glu Ala Ala Ala Lys Ala
1               5

<210> SEQ ID NO 5
<211> LENGTH: 5
<212> TYPE: PRT
<213> ORGANISM: artificial
<220> FEATURE:
<223> OTHER INFORMATION: proline-alanine linker

<400> SEQUENCE: 5

Pro Ala Pro Ala Pro
1               5

<210> SEQ ID NO 6
<211> LENGTH: 5
<212> TYPE: PRT
<213> ORGANISM: artificial
<220> FEATURE:
<223> OTHER INFORMATION: glycine-serine linker (repeated between 2 and -continued 5, inclusive)

<400> SEQUENCE: 6

Gly Gly Gly Gly Ser
1               5

<210> SEQ ID NO 7
<211> LENGTH: 20
<212> TYPE: PRT
<213> ORGANISM: artificial
<220> FEATURE:
<223> OTHER INFORMATION: glycine-serine linker

<400> SEQUENCE: 7

Gly Gly Gly Gly Ser Gly Gly Gly Ser Gly Gly Gly Gly Ser Gly
1               5                   10                  15

Gly Gly Gly Ser
            20

<210> SEQ ID NO 8
<211> LENGTH: 126
<212> TYPE: PRT
<213> ORGANISM: artificial
<220> FEATURE:
<223> OTHER INFORMATION: DARC VHH

<400> SEQUENCE: 8

Met Ala Gln Val Gln Leu Gln Glu Ser Gly Gly Ser Val Gln Ala
1               5                   10                  15

Gly Gly Ser Leu Arg Leu Ser Cys Ala Ala Ser Gly Tyr Ala Phe Ser
                20                  25                  30

Ser Tyr Cys Met Ala Trp Phe Arg Gln Val Pro Gly Lys Glu Arg Glu
            35                  40                  45

Gly Val Ala Ser Ile Asn Ser Asp Gly Glu Arg Arg Gly Tyr Ala Asp
        50                  55                  60

Ser Val Lys Gly Arg Phe Thr Val Ser Arg Asp Asn Ala Lys Asn Thr
65                  70                  75                  80

Val Tyr Leu Gln Met Asn Ser Leu Lys Pro Glu Asp Thr Ala Ile Tyr
                85                  90                  95

Tyr Cys Ala Ala Lys Arg Val Val Gly Gly Arg Tyr Cys Gly Gly
            100                 105                 110

Val Ser Ser Trp Gly Gln Gly Thr Gln Val Thr Val Ser Ser
        115                 120                 125

<210> SEQ ID NO 9
<211> LENGTH: 128
<212> TYPE: PRT
<213> ORGANISM: artificial
<220> FEATURE:
<223> OTHER INFORMATION: DARC VHH with restriction site

<400> SEQUENCE: 9

Met Ala Gln Val Gln Leu Gln Glu Ser Gly Gly Ser Val Gln Ala
1               5                   10                  15

Gly Gly Ser Leu Arg Leu Ser Cys Ala Ala Ser Gly Tyr Ala Phe Ser
                20                  25                  30

Ser Tyr Cys Met Ala Trp Phe Arg Gln Val Pro Gly Lys Glu Arg Glu
            35                  40                  45

Gly Val Ala Ser Ile Asn Ser Asp Gly Glu Arg Arg Gly Tyr Ala Asp
        50                  55                  60

```
Ser Val Lys Gly Arg Phe Thr Val Ser Arg Asp Asn Ala Lys Asn Thr
 65                  70                  75                  80

Val Tyr Leu Gln Met Asn Ser Leu Lys Pro Glu Asp Thr Ala Ile Tyr
                     85                  90                  95

Tyr Cys Ala Ala Lys Arg Val Val Gly Gly Arg Tyr Cys Gly Gly Gly
                100                 105                 110

Val Ser Ser Trp Gly Gln Gly Thr Gln Val Thr Val Ser Ser Ala Ser
            115                 120                 125
```

<210> SEQ ID NO 10
<211> LENGTH: 123
<212> TYPE: PRT
<213> ORGANISM: artificial
<220> FEATURE:
<223> OTHER INFORMATION: VAR2CSA VHH

<400> SEQUENCE: 10

```
Met Ala Gln Val Gln Leu Gln Glu Ser Gly Gly Gly Leu Val Gln Ala
 1               5                  10                  15

Gly Gly Ser Leu Arg Leu Ser Cys Ala Phe Ser Gly Ser Ile Phe Lys
                20                  25                  30

Met Gly Trp Phe Arg Gln Ala Pro Gly Lys Glu Arg Glu Phe Val Ala
             35                  40                  45

Ala Ile Arg Trp Ser Gly Gly Ser Thr Tyr Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asp Ser Leu Lys Pro Glu Asp Thr Ala Val Tyr Tyr Cys Ala
                 85                  90                  95

Ala Thr Trp Asp Leu Ala Gly Trp Asn Thr Val Asp Glu Tyr Asp Tyr
            100                 105                 110

Trp Gly Gln Gly Thr Gln Val Thr Val Ser Ser
            115                 120
```

<210> SEQ ID NO 11
<211> LENGTH: 125
<212> TYPE: PRT
<213> ORGANISM: artificial
<220> FEATURE:
<223> OTHER INFORMATION: VAR2CSA VHH with restriction site

<400> SEQUENCE: 11

```
Met Ala Gln Val Gln Leu Gln Glu Ser Gly Gly Gly Leu Val Gln Ala
 1               5                  10                  15

Gly Gly Ser Leu Arg Leu Ser Cys Ala Phe Ser Gly Ser Ile Phe Lys
                20                  25                  30

Met Gly Trp Phe Arg Gln Ala Pro Gly Lys Glu Arg Glu Phe Val Ala
             35                  40                  45

Ala Ile Arg Trp Ser Gly Gly Ser Thr Tyr Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asp Ser Leu Lys Pro Glu Asp Thr Ala Val Tyr Tyr Cys Ala
                 85                  90                  95

Ala Thr Trp Asp Leu Ala Gly Trp Asn Thr Val Asp Glu Tyr Asp Tyr
            100                 105                 110

Trp Gly Gln Gly Thr Gln Val Thr Val Ser Ser Ala Ser
            115                 120                 125
```

<210> SEQ ID NO 12
<211> LENGTH: 118
<212> TYPE: PRT
<213> ORGANISM: artificial
<220> FEATURE:
<223> OTHER INFORMATION: VSG VHH

<400> SEQUENCE: 12

```
Asp Val Gln Leu Val Glu Ser Gly Gly Gly Ser Val Gln Ala Gly Gly
  1               5                  10                  15

Ser Leu Arg Leu Ser Cys Ala Val Ser Gly Ser Thr Tyr Ser Pro Cys
             20                  25                  30

Thr Thr Gly Trp Tyr Arg Gln Ala Pro Gly Lys Glu Arg Glu Trp Val
         35                  40                  45

Ser Ser Ile Ser Ser Pro Gly Thr Ile Tyr Tyr Gln Asp Ser Val Lys
     50                  55                  60

Gly Arg Phe Thr Ile Ser Arg Asp Asn Ala Lys Asn Thr Val Tyr Leu
 65                  70                  75                  80

Gln Met Asn Ser Leu Gln Arg Glu Asp Thr Gly Met Tyr Tyr Cys Gln
                 85                  90                  95

Ile Gln Cys Gly Val Arg Ser Ile Arg Glu Tyr Trp Gly Gln Gly Thr
            100                 105                 110

Gln Val Thr Val Ser Ser
        115
```

<210> SEQ ID NO 13
<211> LENGTH: 120
<212> TYPE: PRT
<213> ORGANISM: artificial
<220> FEATURE:
<223> OTHER INFORMATION: VSG VHH with restriction site

<400> SEQUENCE: 13

```
Asp Val Gln Leu Val Glu Ser Gly Gly Gly Ser Val Gln Ala Gly Gly
  1               5                  10                  15

Ser Leu Arg Leu Ser Cys Ala Val Ser Gly Ser Thr Tyr Ser Pro Cys
             20                  25                  30

Thr Thr Gly Trp Tyr Arg Gln Ala Pro Gly Lys Glu Arg Glu Trp Val
         35                  40                  45

Ser Ser Ile Ser Ser Pro Gly Thr Ile Tyr Tyr Gln Asp Ser Val Lys
     50                  55                  60

Gly Arg Phe Thr Ile Ser Arg Asp Asn Ala Lys Asn Thr Val Tyr Leu
 65                  70                  75                  80

Gln Met Asn Ser Leu Gln Arg Glu Asp Thr Gly Met Tyr Tyr Cys Gln
                 85                  90                  95

Ile Gln Cys Gly Val Arg Ser Ile Arg Glu Tyr Trp Gly Gln Gly Thr
            100                 105                 110

Gln Val Thr Val Ser Ser Ala Ser
        115                 120
```

<210> SEQ ID NO 14
<211> LENGTH: 198
<212> TYPE: PRT
<213> ORGANISM: artificial
<220> FEATURE:
<223> OTHER INFORMATION: EPCR amino-acid 18-210

<400> SEQUENCE: 14

```
Ser Asp Gly Leu Gln Arg Leu His Met Leu Gln Ile Ser Tyr Phe Arg
1               5                   10                  15

Asp Pro Tyr His Val Trp Tyr Gln Gly Asn Ala Ser Leu Gly Gly His
            20                  25                  30

Leu Thr His Val Leu Glu Gly Pro Asp Thr Asn Thr Thr Ile Ile Gln
        35                  40                  45

Leu Gln Pro Leu Gln Glu Pro Glu Ser Trp Ala Arg Thr Gln Ser Gly
    50                  55                  60

Leu Gln Ser Tyr Leu Leu Gln Phe His Gly Leu Val Arg Leu Val His
65                  70                  75                  80

Gln Glu Arg Thr Leu Ala Phe Pro Leu Thr Ile Arg Cys Phe Leu Gly
                85                  90                  95

Cys Glu Leu Pro Pro Glu Gly Ser Arg Ala His Val Phe Phe Glu Val
            100                 105                 110

Ala Val Asn Gly Ser Ser Phe Val Ser Phe Arg Pro Glu Arg Ala Leu
        115                 120                 125

Trp Gln Ala Asp Thr Gln Val Thr Ser Gly Val Val Thr Phe Thr Leu
    130                 135                 140

Gln Gln Leu Asn Ala Tyr Asn Arg Thr Arg Tyr Glu Leu Arg Glu Phe
145                 150                 155                 160

Leu Glu Asp Thr Cys Val Gln Tyr Val Gln Lys His Ile Ser Ala Glu
                165                 170                 175

Asn Thr Lys Gly Ser Gln Thr Ser Arg Ser Tyr Thr Ser Leu Val Leu
            180                 185                 190

Gly Val Leu Val Gly Ser
            195

<210> SEQ ID NO 15
<211> LENGTH: 176
<212> TYPE: PRT
<213> ORGANISM: Epstein Barr virus
<220> FEATURE:
<221> NAME/KEY: MISC_FEATURE
<223> OTHER INFORMATION: consensus full length EBV P18 antigen
<220> FEATURE:
<221> NAME/KEY: VARIANT
<222> LOCATION: (2)..(2)
<223> OTHER INFORMATION: Ala can be replaced by Ser
<220> FEATURE:
<221> NAME/KEY: VARIANT
<222> LOCATION: (126)..(126)
<223> OTHER INFORMATION: Ala can be replaced by Val
<220> FEATURE:
<221> NAME/KEY: VARIANT
<222> LOCATION: (136)..(136)
<223> OTHER INFORMATION: Ser can be replaced by Asn
<220> FEATURE:
<221> NAME/KEY: VARIANT
<222> LOCATION: (148)..(148)
<223> OTHER INFORMATION: Ala can be absent
<220> FEATURE:
<221> NAME/KEY: VARIANT
<222> LOCATION: (149)..(149)
<223> OTHER INFORMATION: Ser can be absent
<220> FEATURE:
<221> NAME/KEY: VARIANT
<222> LOCATION: (165)..(165)
<223> OTHER INFORMATION: Gln can be replaced by His

<400> SEQUENCE: 15

Met Ala Arg Arg Leu Pro Lys Pro Thr Leu Gln Gly Arg Leu Glu Ala
1               5                   10                  15

Asp Phe Pro Asp Ser Pro Leu Leu Pro Lys Phe Gln Glu Leu Asn Gln
            20                  25                  30
```

```
Asn Asn Leu Pro Asn Asp Val Phe Arg Glu Ala Gln Arg Ser Tyr Leu
         35                  40                  45

Val Phe Leu Thr Ser Gln Phe Cys Tyr Glu Glu Tyr Val Gln Arg Thr
     50                  55                  60

Phe Gly Val Pro Arg Arg Gln Arg Ala Ile Asp Lys Arg Gln Arg Ala
 65              70                  75                      80

Ser Val Ala Gly Ala Gly Ala His Ala His Leu Gly Gly Ser Ser Ala
             85                  90                  95

Thr Pro Val Gln Gln Ala Gln Ala Ala Ser Ala Gly Thr Gly Ala
            100                 105                 110

Leu Ala Ser Ser Ala Pro Ser Thr Ala Val Ala Gln Ser Ala Thr Pro
            115                 120                 125

Ser Val Ser Ser Ile Ser Ser Leu Arg Ala Ala Thr Ser Gly Ala
            130                 135                 140

Thr Ala Ala Ala Ser Ala Ala Ala Val Asp Thr Gly Ser Gly Gly
145                 150                 155                 160

Gly Gly Gln Pro Gln Asp Thr Ala Pro Arg Gly Ala Arg Lys Lys Gln
                165                 170                 175
```

<210> SEQ ID NO 16
<211> LENGTH: 162
<212> TYPE: PRT
<213> ORGANISM: Epstein Barr virus
<220> FEATURE:
<221> NAME/KEY: MISC_FEATURE
<223> OTHER INFORMATION: consensus full length EBV 23 antigen
<220> FEATURE:
<221> NAME/KEY: VARIANT
<222> LOCATION: (39)..(39)
<223> OTHER INFORMATION: Gln can be replaced by Arg
<220> FEATURE:
<221> NAME/KEY: VARIANT
<222> LOCATION: (55)..(55)
<223> OTHER INFORMATION: Ala can be replaced by Val
<220> FEATURE:
<221> NAME/KEY: VARIANT
<222> LOCATION: (56)..(56)
<223> OTHER INFORMATION: Pro can be replaced by Thr
<220> FEATURE:
<221> NAME/KEY: VARIANT
<222> LOCATION: (89)..(89)
<223> OTHER INFORMATION: Asp can be replaced by Glu
<220> FEATURE:
<221> NAME/KEY: VARIANT
<222> LOCATION: (104)..(104)
<223> OTHER INFORMATION: Met can be replaced by Leu
<220> FEATURE:
<221> NAME/KEY: VARIANT
<222> LOCATION: (106)..(106)
<223> OTHER INFORMATION: Asn can be replaced by Lys
<220> FEATURE:
<221> NAME/KEY: VARIANT
<222> LOCATION: (132)..(132)
<223> OTHER INFORMATION: Thr can be replaced by Pro
<220> FEATURE:
<221> NAME/KEY: VARIANT
<222> LOCATION: (134)..(134)
<223> OTHER INFORMATION: Pro can be replaced by Leu or Ser
<220> FEATURE:
<221> NAME/KEY: VARIANT
<222> LOCATION: (135)..(135)
<223> OTHER INFORMATION: Arg can be replaced by Asn or can be absent
<220> FEATURE:
<221> NAME/KEY: VARIANT
<222> LOCATION: (136)..(136)
<223> OTHER INFORMATION: Glu can be replaced by Asp or can be absent
<220> FEATURE:
<221> NAME/KEY: VARIANT
<222> LOCATION: (137)..(137)

```
<223> OTHER INFORMATION: Ser can be replaced by Pro or can be absent
<220> FEATURE:
<221> NAME/KEY: VARIANT
<222> LOCATION: (138)..(138)
<223> OTHER INFORMATION: Asn can be replaced by Ser
<220> FEATURE:
<221> NAME/KEY: VARIANT
<222> LOCATION: (142)..(142)
<223> OTHER INFORMATION: Ala can be replaced by Thr, Ser or Asn
<220> FEATURE:
<221> NAME/KEY: VARIANT
<222> LOCATION: (148)..(148)
<223> OTHER INFORMATION: Ser can be absent
<220> FEATURE:
<221> NAME/KEY: VARIANT
<222> LOCATION: (149)..(149)
<223> OTHER INFORMATION: Arg can be absent
<220> FEATURE:
<221> NAME/KEY: VARIANT
<222> LOCATION: (153)..(153)
<223> OTHER INFORMATION: Arg can be replaced by Cys
<220> FEATURE:
<221> NAME/KEY: VARIANT
<222> LOCATION: (155)..(155)
<223> OTHER INFORMATION: Ala can be replaced by Ser

<400> SEQUENCE: 16

Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Gly Ser Glu
            20                  25                  30

Asn Lys Ala Leu Lys Gln Gln Val Leu Arg Gly Gly Ala Cys Ala Ser
        35                  40                  45

Ser Thr Ser Val Pro Ser Ala Pro Val Pro Pro Glu Pro Leu Thr
    50                  55                  60

Ala Arg Gln Arg Glu Val Met Ile Thr Gln Ala Thr Gly Arg Leu Ala
65                  70                  75                  80

Ser Gln Ala Met Lys Lys Ile Glu Asp Lys Val Arg Lys Ser Val Asp
                85                  90                  95

Gly Val Thr Thr Arg Asn Glu Met Glu Asn Ile Leu Gln Asn Leu Thr
            100                 105                 110

Leu Arg Ile Gln Val Ser Met Leu Gly Ala Lys Gly Pro Ser Pro
        115                 120                 125

Gly Glu Gly Thr Arg Pro Arg Glu Ser Asn Asp Pro Asn Ala Thr Arg
    130                 135                 140

Arg Ala Arg Ser Arg Ser Arg Gly Arg Glu Ala Lys Lys Val Gln Ile
145                 150                 155                 160

Ser Asp

<210> SEQ ID NO 17
<211> LENGTH: 176
<212> TYPE: PRT
<213> ORGANISM: Epstein Barr virus B95-8 strain
<220> FEATURE:
<221> NAME/KEY: MISC_FEATURE
<223> OTHER INFORMATION: wt full length EBV P18 antigen

<400> SEQUENCE: 17

Met Ala Arg Arg Leu Pro Lys Pro Thr Leu Gln Gly Arg Leu Glu Ala
1               5                   10                  15

Asp Phe Pro Asp Ser Pro Leu Leu Pro Lys Phe Gln Glu Leu Asn Gln
            20                  25                  30

Asn Asn Leu Pro Asn Asp Val Phe Arg Glu Ala Gln Arg Ser Tyr Leu
        35                  40                  45
```

```
Val Phe Leu Thr Ser Gln Phe Cys Tyr Glu Glu Tyr Val Gln Arg Thr
 50                  55                  60

Phe Gly Val Pro Arg Arg Gln Arg Ala Ile Asp Lys Arg Gln Arg Ala
 65                  70                  75                  80

Ser Val Ala Gly Ala Gly Ala His Ala His Leu Gly Gly Ser Ser Ala
                 85                  90                  95

Thr Pro Val Gln Gln Ala Gln Ala Ala Ser Ala Gly Thr Gly Ala
                100                 105                 110

Leu Ala Ser Ser Ala Pro Ser Thr Ala Val Ala Gln Ser Ala Thr Pro
            115                 120                 125

Ser Val Ser Ser Ile Ser Ser Leu Arg Ala Ala Thr Ser Gly Ala
            130                 135                 140

Thr Ala Ala Ala Ser Ala Ala Ala Val Asp Thr Gly Ser Gly Gly
145                 150                 155                 160

Gly Gly Gln Pro His Asp Thr Ala Pro Arg Gly Ala Arg Lys Lys Gln
                165                 170                 175
```

<210> SEQ ID NO 18
<211> LENGTH: 176
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P18 antigen

<400> SEQUENCE: 18

```
Met Ala Arg Arg Leu Pro Lys Pro Thr Leu Gln Gly Arg Leu Glu Ala
  1               5                  10                  15

Asp Phe Pro Asp Ser Pro Leu Leu Pro Lys Phe Gln Glu Leu Asn Gln
                 20                  25                  30

Asn Leu Pro Asn Asp Val Phe Arg Glu Ala Gln Arg Ser Tyr Leu
             35                  40                  45

Val Phe Leu Thr Ser Gln Phe Cys Tyr Glu Glu Tyr Val Gln Arg Thr
 50                  55                  60

Phe Gly Val Pro Arg Arg Gln Arg Ala Ile Asp Lys Arg Gln Arg Ala
 65                  70                  75                  80

Ser Val Ala Gly Ala Gly Ala His Ala His Leu Gly Gly Ser Ser Ala
                 85                  90                  95

Thr Pro Val Gln Gln Ala Gln Ala Ala Ser Ala Gly Thr Gly Ala
                100                 105                 110

Leu Ala Ser Ser Ala Pro Ser Thr Ala Val Ala Gln Ser Ala Thr Pro
            115                 120                 125

Ser Val Ser Ser Ile Ser Ser Leu Arg Ala Ala Thr Ser Gly Ala
            130                 135                 140

Thr Ala Ala Ala Ser Ala Ala Ala Val Asp Thr Gly Ser Gly Gly
145                 150                 155                 160

Gly Gly Gln Pro His Asp Thr Ala Pro Arg Gly Ala Arg Lys Lys Gln
                165                 170                 175
```

<210> SEQ ID NO 19
<211> LENGTH: 174
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P18 antigen

<400> SEQUENCE: 19

```
Met Ala Arg Arg Leu Pro Lys Pro Thr Leu Gln Gly Arg Leu Glu Ala
1               5                   10                  15

Asp Phe Pro Asp Ser Pro Leu Leu Pro Lys Phe Gln Glu Leu Asn Gln
            20                  25                  30

Asn Asn Leu Pro Asn Asp Val Phe Arg Glu Ala Gln Arg Ser Tyr Leu
        35                  40                  45

Val Phe Leu Thr Ser Gln Phe Cys Tyr Glu Glu Tyr Val Gln Arg Thr
    50                  55                  60

Phe Gly Val Pro Arg Arg Gln Arg Ala Ile Asp Lys Arg Gln Arg Ala
65                  70                  75                  80

Ser Val Ala Gly Ala Gly Ala His Ala His Leu Gly Gly Ser Ser Ala
                85                  90                  95

Thr Pro Val Gln Gln Ala Gln Ala Ala Ala Ser Ala Gly Thr Gly Ala
            100                 105                 110

Leu Ala Ser Ser Ala Pro Ser Thr Ala Val Ala Gln Ser Ala Thr Pro
        115                 120                 125

Ser Val Ser Ser Ser Ile Ser Ser Leu Arg Ala Ala Thr Ser Gly Ala
    130                 135                 140

Thr Ala Ala Ala Ala Ala Val Asp Thr Gly Ser Gly Gly Gly
145                 150                 155                 160

Gln Pro Gln Asp Thr Ala Pro Arg Gly Ala Arg Lys Lys Gln
                165                 170
```

<210> SEQ ID NO 20
<211> LENGTH: 176
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P18 antigen

<400> SEQUENCE: 20

```
Met Ala Arg Arg Leu Pro Lys Pro Thr Leu Gln Gly Arg Leu Glu Ala
1               5                   10                  15

Asp Phe Pro Asp Ser Pro Leu Leu Pro Lys Phe Gln Glu Leu Asn Gln
            20                  25                  30

Asn Asn Leu Pro Asn Asp Val Phe Arg Glu Ala Gln Arg Ser Tyr Leu
        35                  40                  45

Val Phe Leu Thr Ser Gln Phe Cys Tyr Glu Glu Tyr Val Gln Arg Thr
    50                  55                  60

Phe Gly Val Pro Arg Arg Gln Arg Ala Ile Asp Lys Arg Gln Arg Ala
65                  70                  75                  80

Ser Val Ala Gly Ala Gly Ala His Ala His Leu Gly Gly Ser Ser Ala
                85                  90                  95

Thr Pro Val Gln Gln Ala Gln Ala Ala Ala Ser Ala Gly Thr Gly Ala
            100                 105                 110

Leu Ala Ser Ser Ala Pro Ser Thr Ala Val Ala Gln Ser Ala Thr Pro
        115                 120                 125

Ser Val Ser Ser Ser Ile Ser Asn Leu Arg Ala Ala Thr Ser Gly Ala
    130                 135                 140

Thr Ala Ala Ala Ser Ala Ala Ala Val Asp Thr Gly Ser Gly Gly
145                 150                 155                 160

Gly Gly Gln Pro Gln Asp Thr Ala Pro Arg Gly Ala Arg Lys Lys Gln
                165                 170                 175
```

<210> SEQ ID NO 21
<211> LENGTH: 176
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P18 antigen

<400> SEQUENCE: 21

```
Met Ala Arg Arg Leu Pro Lys Pro Thr Leu Gln Gly Arg Leu Glu Ala
1               5                   10                  15

Asp Phe Pro Asp Ser Pro Leu Leu Pro Lys Phe Gln Glu Leu Asn Gln
            20                  25                  30

Asn Asn Leu Pro Asn Asp Val Phe Arg Glu Ala Gln Arg Ser Tyr Leu
        35                  40                  45

Val Phe Leu Thr Ser Gln Phe Cys Tyr Glu Glu Tyr Val Gln Arg Thr
    50                  55                  60

Phe Gly Val Pro Arg Arg Gln Arg Ala Ile Asp Lys Arg Gln Arg Ala
65                  70                  75                  80

Ser Val Ala Gly Ala Gly Ala His Ala His Leu Gly Gly Ser Ser Ala
                85                  90                  95

Thr Pro Val Gln Gln Ala Gln Ala Ala Ser Ala Gly Thr Gly Ala
            100                 105                 110

Leu Ala Ser Ser Ala Pro Ser Thr Ala Val Ala Gln Ser Val Thr Pro
        115                 120                 125

Ser Val Ser Ser Ser Ile Ser Ser Leu Arg Ala Ala Thr Ser Gly Ala
    130                 135                 140

Thr Ala Ala Ala Ser Ala Ala Ala Val Asp Thr Gly Ser Gly Gly
145                 150                 155                 160

Gly Gly Gln Pro Gln Asp Thr Ala Pro Arg Gly Ala Arg Lys Lys Gln
                165                 170                 175
```

<210> SEQ ID NO 22
<211> LENGTH: 176
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P18 antigen

<400> SEQUENCE: 22

```
Met Ser Arg Arg Leu Pro Lys Pro Thr Leu Gln Gly Arg Leu Glu Ala
1               5                   10                  15

Asp Phe Pro Asp Ser Pro Leu Leu Pro Lys Phe Gln Glu Leu Asn Gln
            20                  25                  30

Asn Asn Leu Pro Asn Asp Val Phe Arg Glu Ala Gln Arg Ser Tyr Leu
        35                  40                  45

Val Phe Leu Thr Ser Gln Phe Cys Tyr Glu Glu Tyr Val Gln Arg Thr
    50                  55                  60

Phe Gly Val Pro Arg Arg Gln Arg Ala Ile Asp Lys Arg Gln Arg Ala
65                  70                  75                  80

Ser Val Ala Gly Ala Gly Ala His Ala His Leu Gly Gly Ser Ser Ala
                85                  90                  95

Thr Pro Val Gln Gln Ala Gln Ala Ala Ser Ala Gly Thr Gly Ala
            100                 105                 110

Leu Ala Ser Ser Ala Pro Ser Thr Ala Val Ala Gln Ser Ala Thr Pro
        115                 120                 125

Ser Val Ser Ser Ser Ile Ser Ser Leu Arg Ala Ala Thr Ser Gly Ala
```

```
            130                 135                 140
Thr Ala Ala Ala Ser Ala Ala Ala Val Asp Thr Gly Ser Gly Gly
145                 150                 155                 160

Gly Gly Gln Pro Gln Asp Thr Ala Pro Arg Gly Ala Arg Lys Lys Gln
                165                 170                 175
```

<210> SEQ ID NO 23
<211> LENGTH: 162
<212> TYPE: PRT
<213> ORGANISM: Epstein Barr virus B95-8 strain
<220> FEATURE:
<221> NAME/KEY: MISC_FEATURE
<223> OTHER INFORMATION: wt full length EBV P23 antigen

<400> SEQUENCE: 23

```
Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Glu Ser Glu
                20                  25                  30

Asn Lys Ala Leu Lys Gln Gln Val Leu Arg Gly Gly Ala Cys Ala Ser
            35                  40                  45

Ser Thr Ser Val Pro Ser Ala Pro Val Pro Pro Glu Pro Leu Thr
        50                  55                  60

Ala Arg Gln Arg Glu Val Met Ile Thr Gln Ala Thr Gly Arg Leu Ala
65                  70                  75                  80

Ser Gln Ala Met Lys Lys Ile Glu Asp Lys Val Arg Lys Ser Val Asp
                85                  90                  95

Gly Val Thr Thr Arg Asn Glu Met Glu Asn Ile Leu Gln Asn Leu Thr
            100                 105                 110

Leu Arg Ile Gln Val Ser Met Leu Gly Ala Lys Gly Gln Pro Ser Pro
        115                 120                 125

Gly Glu Gly Thr Arg Pro Arg Glu Ser Asn Asp Pro Asn Ala Thr Arg
    130                 135                 140

Arg Ala Arg Ser Arg Ser Arg Gly Arg Glu Ala Lys Lys Val Gln Ile
145                 150                 155                 160

Ser Asp
```

<210> SEQ ID NO 24
<211> LENGTH: 162
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P23 antigen

<400> SEQUENCE: 24

```
Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Glu Ser Glu
                20                  25                  30

Asn Lys Ala Leu Lys Gln Gln Val Leu Arg Gly Gly Ala Cys Ala Ser
            35                  40                  45

Ser Thr Ser Val Pro Ser Ala Pro Val Pro Pro Glu Pro Leu Thr
        50                  55                  60

Ala Arg Gln Arg Glu Val Met Ile Thr Gln Ala Thr Gly Arg Leu Ala
65                  70                  75                  80

Ser Gln Ala Met Lys Lys Ile Glu Asp Lys Val Arg Lys Ser Val Asp
                85                  90                  95
```

```
Gly Val Thr Thr Arg Asn Glu Met Glu Asn Ile Leu Gln Asn Leu Thr
                100                 105                 110

Leu Arg Ile Gln Val Ser Met Leu Gly Ala Lys Gly Gln Pro Ser Pro
            115                 120                 125

Gly Glu Gly Thr Arg Leu Arg Glu Ser Asn Asp Pro Asn Ala Thr Arg
        130                 135                 140

Arg Ala Arg Ser Arg Ser Arg Gly Arg Glu Ala Lys Lys Val Gln Ile
145                 150                 155                 160

Ser Asp

<210> SEQ ID NO 25
<211> LENGTH: 159
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P23 antigen

<400> SEQUENCE: 25

Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Glu Ser Glu
            20                  25                  30

Asn Lys Ala Leu Lys Gln Gln Val Leu Arg Gly Gly Ala Cys Ala Ser
        35                  40                  45

Ser Thr Ser Val Pro Ser Ala Pro Val Pro Pro Glu Pro Leu Thr
    50                  55                  60

Ala Arg Gln Arg Glu Val Met Ile Thr Gln Ala Thr Gly Arg Leu Ala
65                  70                  75                  80

Ser Gln Ala Met Lys Lys Ile Glu Asp Lys Val Arg Lys Ser Val Asp
                85                  90                  95

Gly Val Thr Thr Arg Asn Glu Met Glu Asn Ile Leu Gln Asn Leu Thr
                100                 105                 110

Leu Arg Ile Gln Val Ser Met Leu Gly Ala Lys Gly Gln Pro Ser Pro
            115                 120                 125

Gly Glu Gly Thr Arg Pro Asn Asp Pro Asn Ala Thr Arg Arg Ala Arg
        130                 135                 140

Ser Arg Ser Arg Gly Arg Glu Ala Lys Lys Val Gln Ile Ser Asp
145                 150                 155

<210> SEQ ID NO 26
<211> LENGTH: 159
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P23 antigen

<400> SEQUENCE: 26

Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Glu Ser Glu
            20                  25                  30

Asn Lys Ala Leu Lys Gln Gln Val Leu Arg Gly Gly Ala Cys Ala Ser
        35                  40                  45

Ser Thr Ser Val Pro Ser Ala Pro Val Pro Pro Glu Pro Leu Thr
    50                  55                  60
```

```
Ala Arg Gln Arg Glu Val Met Ile Thr Gln Ala Thr Gly Arg Leu Ala
 65                  70                  75                  80

Ser Gln Ala Met Lys Lys Ile Glu Asp Lys Val Arg Lys Ser Val Asp
                 85                  90                  95

Gly Val Thr Thr Arg Asn Glu Met Glu Lys Ile Leu Gln Asn Leu Thr
            100                 105                 110

Leu Arg Ile Gln Val Ser Met Leu Gly Ala Lys Gly Gln Pro Ser Pro
            115                 120                 125

Gly Glu Gly Thr Arg Pro Asn Asp Pro Asn Ala Thr Arg Arg Ala Arg
        130                 135                 140

Ser Arg Ser Arg Gly Arg Glu Ala Lys Lys Val Gln Ile Ser Asp
145                 150                 155
```

<210> SEQ ID NO 27
<211> LENGTH: 162
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P23 antigen

<400> SEQUENCE: 27

```
Met Ser Ala Pro Arg Lys Val Arg Leu Pro Ser Val Lys Ala Val Asp
 1               5                  10                  15

Met Ser Met Glu Asp Met Ala Ala Arg Leu Ala Arg Leu Glu Ser Glu
             20                  25                  30

Asn Lys Ala Leu Lys Gln Gln Val Leu Arg Gly Gly Ala Cys Ala Ser
         35                  40                  45

Ser Thr Ser Val Pro Ser Ala Pro Val Pro Pro Glu Pro Leu Thr
 50                  55                  60

Ala Arg Gln Arg Glu Val Met Ile Thr Gln Ala Thr Gly Arg Leu Ala
 65                  70                  75                  80

Ser Gln Ala Met Lys Lys Ile Glu Asp Lys Val Arg Lys Ser Val Asp
                 85                  90                  95

Gly Val Thr Thr Arg Asn Glu Leu Glu Asn Ile Leu Gln Asn Leu Thr
            100                 105                 110

Leu Arg Ile Gln Val Ser Met Leu Gly Ala Lys Gly Gln Pro Ser Pro
            115                 120                 125

Gly Glu Gly Thr Arg Pro Arg Glu Ser Ser Asp Pro Asn Ala Thr Arg
        130                 135                 140

Arg Ala Arg Ser Arg Ser Arg Gly Arg Glu Ala Lys Lys Val Gln Ile
145                 150                 155                 160

Ser Asp
```

<210> SEQ ID NO 28
<211> LENGTH: 162
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P23 antigen

<400> SEQUENCE: 28

```
Met Ser Ala Pro Arg Lys Val Arg Leu Pro Ser Val Lys Ala Val Asp
 1               5                  10                  15

Met Ser Met Glu Asp Met Ala Ala Arg Leu Ala Arg Leu Glu Ser Glu
             20                  25                  30

Asn Lys Ala Leu Lys Gln Gln Val Leu Arg Gly Gly Ala Cys Ala Ser
```

```
Ser Thr Ser Val Pro Ser Val Pro Val Pro Pro Glu Pro Leu Thr
         50                  55                  60

Ala Arg Gln Arg Glu Val Met Ile Thr Gln Ala Thr Gly Arg Leu Ala
 65                  70                  75                  80

Ser Gln Ala Met Lys Lys Ile Glu Asp Lys Val Arg Lys Ser Val Asp
                 85                  90                  95

Gly Val Thr Thr Arg Asn Glu Met Glu Asn Ile Leu Gln Asn Leu Thr
            100                 105                 110

Leu Arg Ile Gln Val Ser Met Leu Gly Ala Lys Gly Gln Pro Ser Pro
        115                 120                 125

Gly Glu Gly Thr Arg Pro Arg Glu Ser Asn Asp Pro Asn Ala Thr Arg
    130                 135                 140

Arg Ala Arg Ser Arg Ser Arg Gly Arg Glu Ala Lys Lys Val Gln Ile
145                 150                 155                 160

Ser Asp

<210> SEQ ID NO 29
<211> LENGTH: 159
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P23 antigen

<400> SEQUENCE: 29

Met Ser Ala Pro Arg Lys Val Arg Leu Pro Ser Val Lys Ala Val Asp
  1               5                  10                  15

Met Ser Met Glu Asp Met Ala Ala Arg Leu Ala Arg Leu Glu Ser Glu
             20                  25                  30

Asn Lys Ala Leu Lys Gln Arg Val Leu Arg Gly Gly Ala Cys Ala Ser
         35                  40                  45

Ser Thr Ser Val Pro Ser Ala Pro Val Pro Pro Glu Pro Leu Thr
     50                  55                  60

Ala Arg Gln Arg Glu Val Met Ile Thr Gln Ala Thr Gly Arg Leu Ala
 65                  70                  75                  80

Ser Gln Ala Met Lys Lys Ile Glu Asp Lys Val Arg Lys Ser Val Asp
                 85                  90                  95

Gly Val Thr Thr Arg Asn Glu Met Glu Asn Ile Leu Gln Asn Leu Thr
            100                 105                 110

Leu Arg Ile Gln Val Ser Met Leu Gly Ala Lys Gly Gln Pro Ser Pro
        115                 120                 125

Gly Glu Gly Thr Arg Pro Asn Asp Pro Asn Ala Thr Arg Arg Ala Arg
    130                 135                 140

Ser Arg Ser Arg Gly Arg Glu Ala Lys Lys Val Gln Ile Ser Asp
145                 150                 155

<210> SEQ ID NO 30
<211> LENGTH: 159
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P23 antigen

<400> SEQUENCE: 30

Met Ser Ala Pro Arg Lys Val Arg Leu Pro Ser Val Lys Ala Val Asp
  1               5                  10                  15
```

Met Ser Met Glu Asp Met Ala Ala Arg Leu Ala Arg Leu Glu Ser Glu
            20                  25                  30

Asn Lys Ala Leu Lys Gln Gln Val Leu Arg Gly Gly Ala Cys Ala Ser
            35                  40                  45

Ser Thr Ser Val Pro Ser Ala Thr Val Pro Pro Glu Pro Leu Thr
 50                  55                  60

Ala Arg Gln Arg Glu Val Met Ile Thr Gln Ala Thr Gly Arg Leu Ala
 65                  70                  75                  80

Ser Gln Ala Met Lys Lys Ile Glu Asp Lys Val Arg Lys Ser Val Asp
                85                  90                  95

Gly Val Thr Thr Arg Asn Glu Met Glu Asn Ile Leu Gln Asn Leu Thr
            100                 105                 110

Leu Arg Ile Gln Val Ser Met Leu Gly Ala Lys Gly Gln Pro Ser Pro
            115                 120                 125

Gly Glu Gly Thr Arg Pro Asn Asp Pro Asn Ala Thr Arg Ala Arg
130                 135                 140

Ser Arg Ser Arg Gly Arg Glu Ala Lys Lys Val Gln Ile Ser Asp
145                 150                 155

<210> SEQ ID NO 31
<211> LENGTH: 160
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P23 antigen

<400> SEQUENCE: 31

Met Ser Ala Pro Arg Lys Val Arg Leu Pro Ser Val Lys Ala Val Asp
 1               5                  10                  15

Met Ser Met Glu Asp Met Ala Ala Arg Leu Ala Arg Leu Glu Ser Glu
            20                  25                  30

Asn Lys Ala Leu Lys Gln Gln Val Leu Arg Gly Gly Ala Cys Ala Ser
            35                  40                  45

Ser Thr Ser Val Pro Ser Ala Pro Val Pro Pro Glu Pro Leu Thr
 50                  55                  60

Ala Arg Gln Arg Glu Val Met Ile Thr Gln Ala Thr Gly Arg Leu Ala
 65                  70                  75                  80

Ser Gln Ala Met Lys Lys Ile Glu Asp Lys Val Arg Lys Ser Val Asp
                85                  90                  95

Gly Val Thr Thr Arg Asn Glu Met Glu Asn Ile Leu Gln Asn Leu Thr
            100                 105                 110

Leu Arg Ile Gln Val Ser Met Leu Gly Ala Lys Gly Gln Pro Ser Pro
            115                 120                 125

Gly Glu Gly Thr Arg Pro Arg Glu Ser Asn Asp Pro Asn Ala Thr Arg
130                 135                 140

Arg Ala Arg Ser Arg Gly Arg Glu Ala Lys Lys Val Gln Ile Ser Asp
145                 150                 155                 160

<210> SEQ ID NO 32
<211> LENGTH: 162
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P23 antigen

<400> SEQUENCE: 32

```
Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Glu Ser Glu
            20                  25                  30

Asn Lys Ala Leu Lys Gln Gln Val Leu Arg Gly Gly Ala Cys Ala Ser
        35                  40                  45

Ser Thr Ser Val Pro Ser Ala Pro Val Pro Pro Glu Pro Leu Thr
    50                  55                  60

Ala Arg Gln Arg Glu Val Met Ile Thr Gln Ala Thr Gly Arg Leu Ala
65                  70                  75                  80

Ser Gln Ala Met Lys Lys Ile Glu Asp Lys Val Arg Lys Ser Val Asp
                85                  90                  95

Gly Val Thr Thr Arg Asn Glu Met Glu Asn Ile Leu Gln Asn Leu Thr
                100                 105                 110

Leu Arg Ile Gln Val Ser Met Leu Gly Ala Lys Gly Gln Pro Ser Pro
            115                 120                 125

Gly Glu Gly Thr Arg Ser Arg Glu Ser Asn Asp Pro Asn Ala Thr Arg
130                 135                 140

Arg Ala Arg Ser Arg Ser Arg Gly Arg Glu Ala Lys Lys Val Gln Ile
145                 150                 155                 160

Ser Asp

<210> SEQ ID NO 33
<211> LENGTH: 162
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P23 antigen

<400> SEQUENCE: 33

Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Glu Ser Glu
            20                  25                  30

Asn Lys Ala Leu Lys Gln Gln Val Leu Arg Gly Gly Ala Cys Ala Ser
        35                  40                  45

Ser Thr Ser Val Pro Ser Ala Pro Val Pro Pro Glu Pro Leu Thr
    50                  55                  60

Ala Arg Gln Arg Glu Val Met Ile Thr Gln Ala Thr Gly Arg Leu Ala
65                  70                  75                  80

Ser Gln Ala Met Lys Lys Ile Glu Asp Lys Val Arg Lys Ser Val Asp
                85                  90                  95

Gly Val Thr Thr Arg Asn Glu Met Glu Asn Ile Leu Gln Asn Leu Thr
                100                 105                 110

Leu Arg Ile Gln Val Ser Met Leu Gly Ala Lys Gly Gln Pro Ser Pro
            115                 120                 125

Gly Glu Gly Pro Arg Pro Arg Glu Ser Asn Asp Pro Asn Ala Thr Arg
130                 135                 140

Arg Ala Arg Ser Arg Ser Arg Gly Arg Glu Ala Lys Lys Val Gln Ile
145                 150                 155                 160

Ser Asp

<210> SEQ ID NO 34
<211> LENGTH: 162
```

```
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P23 antigen

<400> SEQUENCE: 34

Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Glu Ser Glu
                20                  25                  30

Asn Lys Ala Leu Lys Gln Gln Val Leu Arg Gly Gly Ala Cys Ala Ser
            35                  40                  45

Ser Thr Ser Val Pro Ser Ala Pro Val Pro Pro Glu Pro Leu Thr
50                  55                  60

Ala Arg Gln Arg Glu Val Met Ile Thr Gln Ala Thr Gly Arg Leu Ala
65                  70                  75                  80

Ser Gln Ala Met Lys Lys Ile Glu Asp Lys Val Arg Lys Ser Val Asp
                85                  90                  95

Gly Val Thr Thr Arg Asn Glu Met Glu Asn Ile Leu Gln Asn Leu Thr
            100                 105                 110

Leu Arg Ile Gln Val Ser Met Leu Gly Ala Lys Gly Gln Pro Ser Pro
        115                 120                 125

Gly Glu Gly Thr Arg Pro Arg Glu Ser Asn Asp Pro Asn Thr Thr Arg
130                 135                 140

Arg Ala Arg Ser Arg Ser Arg Gly Arg Glu Ala Lys Lys Val Gln Ile
145                 150                 155                 160

Ser Asp

<210> SEQ ID NO 35
<211> LENGTH: 159
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P23 antigen

<400> SEQUENCE: 35

Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Glu Ser Glu
                20                  25                  30

Asn Lys Ala Leu Lys Gln Gln Val Leu Arg Gly Gly Ala Cys Ala Ser
            35                  40                  45

Ser Thr Ser Val Pro Ser Ala Pro Val Pro Pro Glu Pro Leu Thr
50                  55                  60

Ala Arg Gln Arg Glu Val Met Ile Thr Gln Ala Thr Gly Arg Leu Ala
65                  70                  75                  80

Ser Gln Ala Met Lys Lys Ile Glu Asp Lys Val Arg Lys Ser Val Asp
                85                  90                  95

Gly Val Thr Thr Arg Asn Glu Met Glu Lys Ile Leu Gln Asn Leu Thr
            100                 105                 110

Leu Arg Ile Gln Val Ser Met Leu Gly Ala Lys Gly Gln Pro Ser Pro
        115                 120                 125

Gly Glu Gly Thr Arg Pro Asn Asp Pro Asn Ala Thr Arg Arg Ala Arg
130                 135                 140

Ser Arg Ser Arg Gly Arg Glu Ala Lys Lys Val Gln Ile Ser Asp
```

```
145                 150                 155
```

<210> SEQ ID NO 36
<211> LENGTH: 162
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P23 antigen

<400> SEQUENCE: 36

```
Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Glu Ser Glu
            20                  25                  30

Asn Lys Ala Leu Lys Gln Gln Val Leu Arg Gly Gly Ala Cys Ala Ser
        35                  40                  45

Ser Thr Ser Val Pro Ser Ala Pro Val Pro Pro Glu Pro Leu Thr
    50                  55                  60

Ala Arg Gln Arg Glu Val Met Ile Thr Gln Ala Thr Gly Arg Leu Ala
65                  70                  75                  80

Ser Gln Ala Met Lys Lys Ile Glu Glu Lys Val Arg Lys Ser Val Asp
                85                  90                  95

Gly Val Thr Thr Arg Asn Glu Met Glu Asn Ile Leu Gln Asn Leu Thr
            100                 105                 110

Leu Arg Ile Gln Val Ser Met Leu Gly Ala Lys Gly Gln Pro Ser Pro
        115                 120                 125

Gly Glu Gly Thr Arg Pro Arg Glu Ser Asn Asp Pro Asn Ala Thr Arg
    130                 135                 140

Arg Ala Arg Ser Arg Ser Arg Gly Arg Glu Ala Lys Lys Val Gln Ile
145                 150                 155                 160

Ser Asp
```

<210> SEQ ID NO 37
<211> LENGTH: 162
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P23 antigen

<400> SEQUENCE: 37

```
Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Glu Ser Glu
            20                  25                  30

Asn Lys Ala Leu Lys Gln Gln Val Leu Arg Gly Gly Ala Cys Ala Ser
        35                  40                  45

Ser Thr Ser Val Pro Ser Ala Pro Val Pro Pro Glu Pro Leu Thr
    50                  55                  60

Ala Arg Gln Arg Glu Val Met Ile Thr Gln Ala Thr Gly Arg Leu Ala
65                  70                  75                  80

Ser Gln Ala Met Lys Lys Ile Glu Asp Lys Val Arg Lys Ser Val Asp
                85                  90                  95

Gly Val Thr Thr Arg Asn Glu Met Glu Asn Ile Leu Gln Asn Leu Thr
            100                 105                 110

Leu Arg Ile Gln Val Ser Met Leu Gly Ala Lys Gly Gln Pro Ser Pro
        115                 120                 125
```

```
Gly Glu Gly Thr Arg Pro Arg Glu Ser Asn Asp Pro Asn Ser Thr Arg
        130                 135                 140

Arg Ala Arg Ser Arg Ser Arg Gly Arg Glu Ala Lys Lys Val Gln Ile
145                 150                 155                 160

Ser Asp

<210> SEQ ID NO 38
<211> LENGTH: 162
<212> TYPE: PRT
<213> ORGANISM: Epstein Barr virus alternative strain
<220> FEATURE:
<221> NAME/KEY: MISC_FEATURE
<223> OTHER INFORMATION: wt full length EBV P23 antigen

<400> SEQUENCE: 38

Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Glu Ser Glu
            20                  25                  30

Asn Lys Ala Leu Lys Gln Gln Val Leu Arg Gly Gly Ala Cys Ala Ser
        35                  40                  45

Ser Thr Ser Val Pro Ser Ala Pro Val Pro Pro Glu Pro Leu Thr
    50                  55                  60

Ala Arg Gln Arg Glu Val Met Ile Thr Gln Ala Thr Gly Arg Leu Ala
65                  70                  75                  80

Ser Gln Ala Met Lys Lys Ile Glu Asp Lys Val Arg Lys Ser Val Asp
                85                  90                  95

Gly Val Thr Thr Arg Asn Glu Met Glu Asn Ile Leu Gln Asn Leu Thr
            100                 105                 110

Leu Arg Ile Gln Val Ser Met Leu Gly Ala Lys Gly Gln Pro Ser Pro
        115                 120                 125

Gly Glu Gly Thr Arg Leu Arg Glu Ser Asn Asp Pro Asn Ala Thr Arg
    130                 135                 140

Arg Ala Arg Ser Arg Ser Arg Gly Cys Glu Ser Lys Lys Val Gln Ile
145                 150                 155                 160

Ser Asp

<210> SEQ ID NO 39
<211> LENGTH: 176
<212> TYPE: PRT
<213> ORGANISM: artificial
<220> FEATURE:
<223> OTHER INFORMATION: consensus EBV mutated P18 antigen (C56S)*
<220> FEATURE:
<221> NAME/KEY: VARIANT
<222> LOCATION: (2)..(2)
<223> OTHER INFORMATION: Ala can be replaced by Ser
<220> FEATURE:
<221> NAME/KEY: VARIANT
<222> LOCATION: (126)..(126)
<223> OTHER INFORMATION: Ala can be replaced by Val
<220> FEATURE:
<221> NAME/KEY: VARIANT
<222> LOCATION: (136)..(136)
<223> OTHER INFORMATION: Ser can be replaced by Asn
<220> FEATURE:
<221> NAME/KEY: VARIANT
<222> LOCATION: (148)..(148)
<223> OTHER INFORMATION: Ala can be absent
<220> FEATURE:
<221> NAME/KEY: VARIANT
<222> LOCATION: (149)..(149)
<223> OTHER INFORMATION: Ser can be absent
```

```
<220> FEATURE:
<221> NAME/KEY: VARIANT
<222> LOCATION: (165)..(165)
<223> OTHER INFORMATION: Gln can be replaced by His

<400> SEQUENCE: 39

Met Ala Arg Arg Leu Pro Lys Pro Thr Leu Gln Gly Arg Leu Glu Ala
1               5                   10                  15

Asp Phe Pro Asp Ser Pro Leu Leu Pro Lys Phe Gln Glu Leu Asn Gln
            20                  25                  30

Asn Leu Pro Asn Asp Val Phe Arg Glu Ala Gln Arg Ser Tyr Leu
        35                  40                  45

Val Phe Leu Thr Ser Gln Phe Ser Tyr Glu Glu Tyr Val Gln Arg Thr
50                  55                  60

Phe Gly Val Pro Arg Arg Gln Arg Ala Ile Asp Lys Arg Gln Arg Ala
65                  70                  75                  80

Ser Val Ala Gly Ala Gly Ala His Ala His Leu Gly Gly Ser Ser Ala
                85                  90                  95

Thr Pro Val Gln Gln Ala Gln Ala Ala Ser Ala Gly Thr Gly Ala
            100                 105                 110

Leu Ala Ser Ser Ala Pro Ser Thr Ala Val Ala Gln Ser Ala Thr Pro
            115                 120                 125

Ser Val Ser Ser Ile Ser Ser Leu Arg Ala Ala Thr Ser Gly Ala
        130                 135                 140

Thr Ala Ala Ala Ser Ala Ala Ala Val Asp Thr Gly Ser Gly Gly
145                 150                 155                 160

Gly Gly Gln Pro Gln Asp Thr Ala Pro Arg Gly Ala Arg Lys Lys Gln
                165                 170                 175

<210> SEQ ID NO 40
<211> LENGTH: 162
<212> TYPE: PRT
<213> ORGANISM: artificial
<220> FEATURE:
<223> OTHER INFORMATION: consensus EBV mutated P23 antigen (C46S)*
<220> FEATURE:
<221> NAME/KEY: VARIANT
<222> LOCATION: (39)..(39)
<223> OTHER INFORMATION: Gln can be replaced by Arg
<220> FEATURE:
<221> NAME/KEY: VARIANT
<222> LOCATION: (55)..(55)
<223> OTHER INFORMATION: Ala can be replaced by Val
<220> FEATURE:
<221> NAME/KEY: VARIANT
<222> LOCATION: (56)..(56)
<223> OTHER INFORMATION: Pro can be replaced by Thr
<220> FEATURE:
<221> NAME/KEY: VARIANT
<222> LOCATION: (89)..(89)
<223> OTHER INFORMATION: Asp can be replaced by Glu
<220> FEATURE:
<221> NAME/KEY: VARIANT
<222> LOCATION: (104)..(104)
<223> OTHER INFORMATION: Met can be replaced by Leu
<220> FEATURE:
<221> NAME/KEY: VARIANT
<222> LOCATION: (106)..(106)
<223> OTHER INFORMATION: Asn can be replaced by Lys
<220> FEATURE:
<221> NAME/KEY: VARIANT
<222> LOCATION: (132)..(132)
<223> OTHER INFORMATION: Thr can be replaced by Pro
<220> FEATURE:
<221> NAME/KEY: VARIANT
<222> LOCATION: (134)..(134)
<223> OTHER INFORMATION: Pro can be replaced by Leu or Ser
```

```
<220> FEATURE:
<221> NAME/KEY: VARIANT
<222> LOCATION: (135)..(135)
<223> OTHER INFORMATION: Arg can be replaced by Asn or can be absent
<220> FEATURE:
<221> NAME/KEY: VARIANT
<222> LOCATION: (136)..(136)
<223> OTHER INFORMATION: Glu can be replaced by Asp or can be absent
<220> FEATURE:
<221> NAME/KEY: VARIANT
<222> LOCATION: (137)..(137)
<223> OTHER INFORMATION: Ser can be replaced by Pro or can be absent
<220> FEATURE:
<221> NAME/KEY: VARIANT
<222> LOCATION: (138)..(138)
<223> OTHER INFORMATION: Asn can be replaced by Ser
<220> FEATURE:
<221> NAME/KEY: VARIANT
<222> LOCATION: (142)..(142)
<223> OTHER INFORMATION: Ala can be replaced by Thr, Ser or Asn
<220> FEATURE:
<221> NAME/KEY: VARIANT
<222> LOCATION: (148)..(148)
<223> OTHER INFORMATION: Ser can be absent
<220> FEATURE:
<221> NAME/KEY: VARIANT
<222> LOCATION: (149)..(149)
<223> OTHER INFORMATION: Arg can be absent
<220> FEATURE:
<221> NAME/KEY: VARIANT
<222> LOCATION: (153)..(153)
<223> OTHER INFORMATION: Arg can be replaced by Cys
<220> FEATURE:
<221> NAME/KEY: VARIANT
<222> LOCATION: (155)..(155)
<223> OTHER INFORMATION: Ala can be replaced by Ser

<400> SEQUENCE: 40

Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Glu Ser Glu
                20                  25                  30

Asn Lys Ala Leu Lys Gln Gln Val Leu Arg Gly Gly Ala Ser Ala Ser
            35                  40                  45

Ser Thr Ser Val Pro Ser Ala Pro Val Pro Pro Glu Pro Leu Thr
50                  55                  60

Ala Arg Gln Arg Glu Val Met Ile Thr Gln Ala Thr Gly Arg Leu Ala
65                  70                  75                  80

Ser Gln Ala Met Lys Lys Ile Glu Asp Lys Val Arg Lys Ser Val Asp
                85                  90                  95

Gly Val Thr Thr Arg Asn Glu Met Glu Asn Ile Leu Gly Asn Leu Thr
            100                 105                 110

Leu Arg Ile Gln Val Ser Met Leu Gly Ala Lys Gly Gln Pro Ser Pro
        115                 120                 125

Gly Glu Gly Thr Arg Pro Arg Glu Ser Asn Asp Pro Asn Ala Thr Arg
    130                 135                 140

Arg Ala Arg Ser Arg Ser Arg Gly Arg Glu Ala Lys Lys Val Gln Ile
145                 150                 155                 160

Ser Asp

<210> SEQ ID NO 41
<211> LENGTH: 176
<212> TYPE: PRT
<213> ORGANISM: artificial
<220> FEATURE:
<223> OTHER INFORMATION: EBV mutated P18 antigen (C56S)*
```

```
<400> SEQUENCE: 41

Met Ala Arg Arg Leu Pro Lys Pro Thr Leu Gln Gly Arg Leu Glu Ala
1               5                   10                  15

Asp Phe Pro Asp Ser Pro Leu Leu Pro Lys Phe Gln Glu Leu Asn Gln
            20                  25                  30

Asn Asn Leu Pro Asn Asp Val Phe Arg Glu Ala Gln Arg Ser Tyr Leu
        35                  40                  45

Val Phe Leu Thr Ser Gln Phe Ser Tyr Glu Gly Tyr Val Gln Arg Thr
50                  55                  60

Phe Gly Val Pro Arg Arg Gln Arg Ala Ile Asp Lys Arg Gln Arg Ala
65                  70                  75                  80

Ser Val Ala Gly Ala Gly Ala His Ala His Leu Gly Ser Ser Ala
                85                  90                  95

Thr Pro Val Gln Gln Ala Gln Ala Ala Ser Ala Gly Thr Gly Ala
            100                 105                 110

Leu Ala Ser Ser Ala Pro Ser Thr Ala Val Gln Ser Ala Thr Pro
        115                 120                 125

Ser Val Ser Ser Ser Ile Ser Ser Leu Arg Ala Ala Thr Ser Gly Ala
    130                 135                 140

Thr Ala Ala Ala Ser Ala Ala Ala Val Asp Thr Gly Ser Gly Gly
145                 150                 155                 160

Gly Gly Gln Pro His Asp Thr Ala Pro Arg Gly Ala Arg Lys Lys Gln
                165                 170                 175

<210> SEQ ID NO 42
<211> LENGTH: 162
<212> TYPE: PRT
<213> ORGANISM: artificial
<220> FEATURE:
<223> OTHER INFORMATION: EBV mutated P23 antigen (C46S)*

<400> SEQUENCE: 42

Met Ser Ala Pro Arg Lys Val Arg Leu Pro Ser Val Lys Ala Val Asp
1               5                   10                  15

Met Ser Met Glu Asp Met Ala Ala Arg Leu Ala Arg Leu Glu Ser Glu
            20                  25                  30

Asn Lys Ala Leu Lys Gln Gln Val Leu Arg Gly Gly Ala Ser Ala Ser
        35                  40                  45

Ser Thr Ser Val Pro Ser

```
<211> LENGTH: 23
<212> TYPE: PRT
<213> ORGANISM: artificial
<220> FEATURE:
<223> OTHER INFORMATION: consensus EBV P18 antigen fragment F4
<220> FEATURE:
<221> NAME/KEY: VARIANT
<222> LOCATION: (12)..(12)
<223> OTHER INFORMATION: Gln can be replaced by His

<400> SEQUENCE: 43

Val Asp Thr Gly Ser Gly Gly Gly Gly Gln Pro Gln Asp Thr Ala Pro
1               5                   10                  15

Arg Gly Ala Arg Lys Lys Gln
            20

<210> SEQ ID NO 44
<211> LENGTH: 94
<212> TYPE: PRT
<213> ORGANISM: artificial
<220> FEATURE:
<223> OTHER INFORMATION: consensus EBV P18 antigen fragment F3'
<220> FEATURE:
<221> NAME/KEY: VARIANT
<222> LOCATION: (44)..(44)
<223> OTHER INFORMATION: Ala can be replaced by Val
<220> FEATURE:
<221> NAME/KEY: VARIANT
<222> LOCATION: (54)..(54)
<223> OTHER INFORMATION: Ser can be replaced by Asn
<220> FEATURE:
<221> NAME/KEY: VARIANT
<222> LOCATION: (66)..(66)
<223> OTHER INFORMATION: Ala can be absent
<220> FEATURE:
<221> NAME/KEY: VARIANT
<222> LOCATION: (67)..(67)
<223> OTHER INFORMATION: Ser can be absent
<220> FEATURE:
<221> NAME/KEY: VARIANT
<222> LOCATION: (83)..(83)
<223> OTHER INFORMATION: Gln can be replaced by His

<400> SEQUENCE: 44

Ala Gly Ala Gly Ala His Ala His Leu Gly Gly Ser Ser Ala Thr Pro
1               5                   10                  15

Val Gln Gln Ala Gln Ala Ala Ala Ser Ala Gly Thr Gly Ala Leu Ala
            20                  25                  30

Ser Ser Ala Pro Ser Thr Ala Val Ala Gln Ser Ala Thr Pro Ser Val
        35                  40                  45

Ser Ser Ser Ile Ser Ser Leu Arg Ala Ala Thr Ser Gly Ala Thr Ala
    50                  55                  60

Ala Ala Ser Ala Ala Ala Ala Val Asp Thr Gly Ser Gly Gly Gly Gly
65                  70                  75                  80

Gln Pro Gln Asp Thr Ala Pro Arg Gly Ala Arg Lys Lys Gln
                85                  90

<210> SEQ ID NO 45
<211> LENGTH: 84
<212> TYPE: PRT
<213> ORGANISM: artificial
<220> FEATURE:
<223> OTHER INFORMATION: consensus EBV P18 antigen fragment F2-F4
<220> FEATURE:
<221> NAME/KEY: VARIANT
<222> LOCATION: (57)..(57)
<223> OTHER INFORMATION: Ala can be replaced by Val
<220> FEATURE:
<221> NAME/KEY: VARIANT
```

```
<222> LOCATION: (67)..(67)
<223> OTHER INFORMATION: Ser can be replaced by Asn
<220> FEATURE:
<221> NAME/KEY: VARIANT
<222> LOCATION: (79)..(79)
<223> OTHER INFORMATION: Ala can be absent
<220> FEATURE:
<221> NAME/KEY: VARIANT
<222> LOCATION: (80)..(80)
<223> OTHER INFORMATION: Ser can be absent

<400> SEQUENCE: 45

Arg Gln Arg Ala Ile Asp Lys Arg Gln Arg Ala Ser Val Ala Gly Ala
1               5                   10                  15

Gly Ala His Ala His Leu Gly Gly Ser Ser Ala Thr Pro Val Gln Gln
            20                  25                  30

Ala Gln Ala Ala Ala Ser Ala Gly Thr Gly Ala Leu Ala Ser Ser Ala
        35                  40                  45

Pro Ser Thr Ala Val Ala Gln Ser Ala Thr Pro Ser Val Ser Ser
    50                  55                  60

Ile Ser Ser Leu Arg Ala Ala Thr Ser Gly Ala Thr Ala Ala Ala Ser
65                  70                  75                  80

Ala Ala Ala Ala

<210> SEQ ID NO 46
<211> LENGTH: 71
<212> TYPE: PRT
<213> ORGANISM: artificial
<220> FEATURE:
<223> OTHER INFORMATION: Consensus EBV P18 antigen fragment F3'-F4
<220> FEATURE:
<221> NAME/KEY: VARIANT
<222> LOCATION: (44)..(44)
<223> OTHER INFORMATION: Ala can be replaced by Val
<220> FEATURE:
<221> NAME/KEY: VARIANT
<222> LOCATION: (54)..(54)
<223> OTHER INFORMATION: Ser can be replaced by Asn
<220> FEATURE:
<221> NAME/KEY: VARIANT
<222> LOCATION: (66)..(66)
<223> OTHER INFORMATION: Ala can be absent
<220> FEATURE:
<221> NAME/KEY: VARIANT
<222> LOCATION: (67)..(67)
<223> OTHER INFORMATION: Ser can be absent

<400> SEQUENCE: 46

Ala Gly Ala Gly Ala His Ala His Leu Gly Gly Ser Ser Ala Thr Pro
1               5                   10                  15

Val Gln Gln Ala Gln Ala Ala Ala Ser Ala Gly Thr Gly Ala Leu Ala
            20                  25                  30

Ser Ser Ala Pro Ser Thr Ala Val Ala Gln Ser Ala Thr Pro Ser Val
        35                  40                  45

Ser Ser Ser Ile Ser Ser Leu Arg Ala Ala Thr Ser Gly Ala Thr Ala
    50                  55                  60

Ala Ala Ser Ala Ala Ala Ala
65                  70

<210> SEQ ID NO 47
<211> LENGTH: 20
<212> TYPE: PRT
<213> ORGANISM: artificial
<220> FEATURE:
<223> OTHER INFORMATION: Consensus EBV P18 antigen fragment P18F5
<220> FEATURE:
```

```
<221> NAME/KEY: VARIANT
<222> LOCATION: (2)..(2)
<223> OTHER INFORMATION: Ala can be replaced by Val
<220> FEATURE:
<221> NAME/KEY: VARIANT
<222> LOCATION: (12)..(12)
<223> OTHER INFORMATION: Ser can be replaced by Asn

<400> SEQUENCE: 47

Ser Ala Thr Pro Ser Val Ser Ser Ile Ser Ser Leu Arg Ala Ala
1               5                   10                  15

Thr Ser Gly Ala
            20

<210> SEQ ID NO 48
<211> LENGTH: 10
<212> TYPE: PRT
<213> ORGANISM: artificial
<220> FEATURE:
<223> OTHER INFORMATION: Consensus EBV P18 antigen fragment P18F6
<220> FEATURE:
<221> NAME/KEY: VARIANT
<222> LOCATION: (8)..(8)
<223> OTHER INFORMATION: Ser can be replaced by Asn

<400> SEQUENCE: 48

Ser Val Ser Ser Ser Ile Ser Ser Leu Arg
1               5                   10

<210> SEQ ID NO 49
<211> LENGTH: 107
<212> TYPE: PRT
<213> ORGANISM: artificial
<220> FEATURE:
<223> OTHER INFORMATION: consensus EBV P18 antigen fragment F2
<220> FEATURE:
<221> NAME/KEY: VARIANT
<222> LOCATION: (57)..(57)
<223> OTHER INFORMATION: Ala can be replaced by Val
<220> FEATURE:
<221> NAME/KEY: VARIANT
<222> LOCATION: (67)..(67)
<223> OTHER INFORMATION: Ser can be replaced by Asn
<220> FEATURE:
<221> NAME/KEY: VARIANT
<222> LOCATION: (79)..(79)
<223> OTHER INFORMATION: Ala can be absent
<220> FEATURE:
<221> NAME/KEY: VARIANT
<222> LOCATION: (80)..(80)
<223> OTHER INFORMATION: Ser can be absent
<220> FEATURE:
<221> NAME/KEY: VARIANT
<222> LOCATION: (96)..(96)
<223> OTHER INFORMATION: Gln can be replaced by His

<400> SEQUENCE: 49

Arg Gln Arg Ala Ile Asp Lys Arg Gln Arg Ala Ser Val Ala Gly Ala
1               5                   10                  15

Gly Ala His Ala His Leu Gly Gly Ser Ser Ala Thr Pro Val Gln Gln
            20                  25                  30

Ala Gln Ala Ala Ser Ala Gly Thr Gly Ala Leu Ala Ser Ser Ala
        35                  40                  45

Pro Ser Thr Ala Val Ala Gln Ser Ala Thr Pro Ser Val Ser Ser Ser
    50                  55                  60

Ile Ser Ser Leu Arg Ala Ala Thr Ser Gly Ala Thr Ala Ala Ala Ser
65                  70                  75                  80

Ala Ala Ala Ala Val Asp Thr Gly Ser Gly Gly Gly Gly Gln Pro Gln
```

-continued

```
                85                  90                  95

Asp Thr Ala Pro Arg Gly Ala Arg Lys Lys Gln
            100                 105

<210> SEQ ID NO 50
<211> LENGTH: 60
<212> TYPE: PRT
<213> ORGANISM: artificial
<220> FEATURE:
<223> OTHER INFORMATION: consensus EBV P23 antigen fragment F3
<220> FEATURE:
<221> NAME/KEY: VARIANT
<222> LOCATION: (2)..(2)
<223> OTHER INFORMATION: Met can be replaced by Leu
<220> FEATURE:
<221> NAME/KEY: VARIANT
<222> LOCATION: (4)..(4)
<223> OTHER INFORMATION: Asn can be replaced by Lys
<220> FEATURE:
<221> NAME/KEY: VARIANT
<222> LOCATION: (30)..(30)
<223> OTHER INFORMATION: Thr can be replaced by Pro
<220> FEATURE:
<221> NAME/KEY: VARIANT
<222> LOCATION: (32)..(32)
<223> OTHER INFORMATION: Pro can be replaced by Leu or Ser
<220> FEATURE:
<221> NAME/KEY: VARIANT
<222> LOCATION: (33)..(33)
<223> OTHER INFORMATION: Arg can be replaced by Asn or can be absent
<220> FEATURE:
<221> NAME/KEY: VARIANT
<222> LOCATION: (34)..(34)
<223> OTHER INFORMATION: Glu can be replaced by Asp or can be absent
<220> FEATURE:
<221> NAME/KEY: VARIANT
<222> LOCATION: (35)..(35)
<223> OTHER INFORMATION: Ser can be replaced by Pro or can be absent
<220> FEATURE:
<221> NAME/KEY: VARIANT
<222> LOCATION: (36)..(36)
<223> OTHER INFORMATION: Asn can be replaced by Ser
<220> FEATURE:
<221> NAME/KEY: VARIANT
<222> LOCATION: (40)..(40)
<223> OTHER INFORMATION: Ala can be replaced by Thr, Ser or Asn
<220> FEATURE:
<221> NAME/KEY: VARIANT
<222> LOCATION: (46)..(46)
<223> OTHER INFORMATION: Ser can be absent
<220> FEATURE:
<221> NAME/KEY: VARIANT
<222> LOCATION: (47)..(47)
<223> OTHER INFORMATION: Arg can be absent
<220> FEATURE:
<221> NAME/KEY: VARIANT
<222> LOCATION: (51)..(51)
<223> OTHER INFORMATION: Arg can be replaced by Cys
<220> FEATURE:
<221> NAME/KEY: VARIANT
<222> LOCATION: (53)..(53)
<223> OTHER INFORMATION: Ala can be replaced by Ser

<400> SEQUENCE: 50

Glu Met Glu Asn Ile Leu Gln Asn Leu Thr Leu Arg Ile Gln Val Ser
1               5                   10                  15

Met Leu Gly Ala Lys Gly Gln Pro Ser Pro Gly Glu Gly Thr Arg Pro
            20                  25                  30

Arg Glu Ser Asn Asp Pro Asn Ala Thr Arg Arg Ala Arg Ser Arg Ser
        35                  40                  45

Arg Gly Arg Glu Ala Lys Lys Val Gln Ile Ser Asp
    50                  55                  60
```

```
<210> SEQ ID NO 51
<211> LENGTH: 88
<212> TYPE: PRT
<213> ORGANISM: artificial
<220> FEATURE:
<223> OTHER INFORMATION: consensus EBV P23 antigen fragment F2
<220> FEATURE:
<221> NAME/KEY: VARIANT
<222> LOCATION: (15)..(15)
<223> OTHER INFORMATION: Asp can be replaced by Glu
<220> FEATURE:
<221> NAME/KEY: VARIANT
<222> LOCATION: (30)..(30)
<223> OTHER INFORMATION: Met can be replaced by Leu
<220> FEATURE:
<221> NAME/KEY: VARIANT
<222> LOCATION: (32)..(32)
<223> OTHER INFORMATION: Asn can be replaced by Lys
<220> FEATURE:
<221> NAME/KEY: VARIANT
<222> LOCATION: (58)..(58)
<223> OTHER INFORMATION: Thr can be replaced by Pro
<220> FEATURE:
<221> NAME/KEY: VARIANT
<222> LOCATION: (60)..(60)
<223> OTHER INFORMATION: Pro can be replaced by Leu or Ser
<220> FEATURE:
<221> NAME/KEY: VARIANT
<222> LOCATION: (61)..(61)
<223> OTHER INFORMATION: Arg can be replaced by Asn or can be absent
<220> FEATURE:
<221> NAME/KEY: VARIANT
<222> LOCATION: (62)..(62)
<223> OTHER INFORMATION: Glu can be replaced by Asp or can be absent
<220> FEATURE:
<221> NAME/KEY: VARIANT
<222> LOCATION: (63)..(63)
<223> OTHER INFORMATION: Ser can be replaced by Pro or can be absent
<220> FEATURE:
<221> NAME/KEY: VARIANT
<222> LOCATION: (64)..(64)
<223> OTHER INFORMATION: Asn can be replaced by Ser
<220> FEATURE:
<221> NAME/KEY: VARIANT
<222> LOCATION: (68)..(68)
<223> OTHER INFORMATION: Ala can be replaced by Thr, Ser or Asn
<220> FEATURE:
<221> NAME/KEY: VARIANT
<222> LOCATION: (74)..(74)
<223> OTHER INFORMATION: Ser can be absent
<220> FEATURE:
<221> NAME/KEY: VARIANT
<222> LOCATION: (75)..(75)
<223> OTHER INFORMATION: Arg can be absent
<220> FEATURE:
<221> NAME/KEY: VARIANT
<222> LOCATION: (79)..(79)
<223> OTHER INFORMATION: Arg can be replaced by Cys
<220> FEATURE:
<221> NAME/KEY: VARIANT
<222> LOCATION: (81)..(81)
<223> OTHER INFORMATION: Ala can be replaced by Ser

<400> SEQUENCE: 51

Ala Thr Gly Arg Leu Ala Ser Gln Ala Met Lys Lys Ile Glu Asp Lys
 1               5                  10                  15

Val Arg Lys Ser Val Asp Gly Val Thr Thr Arg Asn Glu Met Glu Asn
                20                  25                  30

Ile Leu Gln Asn Leu Thr Leu Arg Ile Gln Val Ser Met Leu Gly Ala
            35                  40                  45

Lys Gly Gln Pro Ser Pro Gly Glu Gly Thr Arg Pro Arg Glu Ser Asn
        50                  55                  60

Asp Pro Asn Ala Thr Arg Arg Ala Arg Ser Arg Ser Arg Gly Arg Glu
```

```
            65                  70                  75                  80
Ala Lys Lys Val Gln Ile Ser Asp
                85

<210> SEQ ID NO 52
<211> LENGTH: 23
<212> TYPE: PRT
<213> ORGANISM: artificial
<220> FEATURE:
<223> OTHER INFORMATION: EBV P18 antigen fragment F4

<400> SEQUENCE: 52

Val Asp Thr Gly Ser Gly Gly Gly Gln Pro His Asp Thr Ala Pro
1               5                   10                  15

Arg Gly Ala Arg Lys Lys Gln
            20

<210> SEQ ID NO 53
<211> LENGTH: 92
<212> TYPE: PRT
<213> ORGANISM: artificial
<220> FEATURE:
<223> OTHER INFORMATION: EBV P18 antigen fragment F3'

<400> SEQUENCE: 53

Ala Gly Ala His Ala His Leu Gly Gly Ser Ser Ala Thr Pro Val Gln
1               5                   10                  15

Gln Ala Gln Ala Ala Ala Ser Ala Gly Thr Gly Ala Leu Ala Ser Ser
                20                  25                  30

Ala Pro Ser Thr Ala Val Ala Gln Ser Ala Thr Pro Ser Val Ser Ser
            35                  40                  45

Ser Ile Ser Ser Leu Arg Ala Ala Thr Ser Gly Ala Thr Ala Ala Ala
    50                  55                  60

Ser Ala Ala Ala Val Asp Thr Gly Ser Gly Gly Gly Gln Pro
65                  70                  75                  80

His Asp Thr Ala Pro Arg Gly Ala Arg Lys Lys Gln
                85                  90

<210> SEQ ID NO 54
<211> LENGTH: 84
<212> TYPE: PRT
<213> ORGANISM: artificial
<220> FEATURE:
<223> OTHER INFORMATION: EBV P18 antigen fragment F2-F4

<400> SEQUENCE: 54

Arg Gln Arg Ala Ile Asp Lys Arg Gln Arg Ala Ser Val Ala Gly Ala
1               5                   10                  15

Gly Ala His Ala His Leu Gly Gly Ser Ser Ala Thr Pro Val Gln Gln
                20                  25                  30

Ala Gln Ala Ala Ala Ser Ala Gly Thr Gly Ala Leu Ala Ser Ser Ala
            35                  40                  45

Pro Ser Thr Ala Val Ala Gln Ser Ala Thr Pro Ser Val Ser Ser Ser
    50                  55                  60

Ile Ser Ser Leu Arg Ala Ala Thr Ser Gly Ala Thr Ala Ala Ala Ser
65                  70                  75                  80

Ala Ala Ala Ala

<210> SEQ ID NO 55
<211> LENGTH: 71
```

```
<212> TYPE: PRT
<213> ORGANISM: artificial
<220> FEATURE:
<223> OTHER INFORMATION: EBV P18 antigen fragment F3'-F4

<400> SEQUENCE: 55

Ala Gly Ala Gly Ala His Ala His Leu Gly Gly Ser Ser Ala Thr Pro
1               5                   10                  15

Val Gln Gln Ala Gln Ala Ala Ala Ser Ala Gly Thr Gly Ala Leu Ala
            20                  25                  30

Ser Ser Ala Pro Ser Thr Ala Val Ala Gln Ser Ala Thr Pro Ser Val
        35                  40                  45

Ser Ser Ser Ile Ser Ser Leu Arg Ala Ala Thr Ser Gly Ala Thr Ala
    50                  55                  60

Ala Ala Ser Ala Ala Ala Ala
65                  70

<210> SEQ ID NO 56
<211> LENGTH: 20
<212> TYPE: PRT
<213> ORGANISM: artificial
<220> FEATURE:
<223> OTHER INFORMATION: EBV P18 antigen fragment P18F5

<400> SEQUENCE: 56

Ser Ala Thr Pro Ser Val Ser Ser Ser Ile Ser Ser Leu Arg Ala Ala
1               5                   10                  15

Thr Ser Gly Ala
            20

<210> SEQ ID NO 57
<211> LENGTH: 10
<212> TYPE: PRT
<213> ORGANISM: artificial
<220> FEATURE:
<223> OTHER INFORMATION: EBV P18 antigen fragment P18F6

<400> SEQUENCE: 57

Ser Val Ser Ser Ser Ile Ser Ser Leu Arg
1               5                   10

<210> SEQ ID NO 58
<211> LENGTH: 107
<212> TYPE: PRT
<213> ORGANISM: artificial
<220> FEATURE:
<223> OTHER INFORMATION: EBV P18 antigen fragment F2

<400> SEQUENCE: 58

Arg Gln Arg Ala Ile Asp Lys Arg Gln Arg Ala Ser Val Ala Gly Ala
1               5                   10                  15

Gly Ala His Ala His Leu Gly Gly Ser Ser Ala Thr Pro Val Gln Gln
            20                  25                  30

Ala Gln Ala Ala Ala Ser Ala Gly Thr Gly Ala Leu Ala Ser Ser Ala
        35                  40                  45

Pro Ser Thr Ala Val Ala Gln Ser Ala Thr Pro Ser Val Ser Ser Ser
    50                  55                  60

Ile Ser Ser Leu Arg Ala Ala Thr Ser Gly Ala Thr Ala Ala Ala Ser
65                  70                  75                  80

Ala Ala Ala Ala Val Asp Thr Gly Ser Gly Gly Gly Gln Pro His
                85                  90                  95
```

```
Asp Thr Ala Pro Arg Gly Ala Arg Lys Lys Gln
            100                 105
```

<210> SEQ ID NO 59
<211> LENGTH: 60
<212> TYPE: PRT
<213> ORGANISM: artificial
<220> FEATURE:
<223> OTHER INFORMATION: EBV P23 antigen fragment F3

<400> SEQUENCE: 59

```
Glu Met Glu Asn Ile Leu Gln Asn Leu Thr Leu Arg Ile Gln Val Ser
1               5                   10                  15

Met Leu Gly Ala Lys Gly Gln Pro Ser Pro Gly Glu Gly Thr Arg Pro
            20                  25                  30

Arg Glu Ser Asn Asp Pro Asn Ala Thr Arg Arg Ala Arg Ser Arg Ser
        35                  40                  45

Arg Gly Arg Glu Ala Lys Lys Val Gln Ile Ser Asp
    50                  55                  60
```

<210> SEQ ID NO 60
<211> LENGTH: 88
<212> TYPE: PRT
<213> ORGANISM: artificial
<220> FEATURE:
<223> OTHER INFORMATION: EBV P23 antigen fragment F2

<400> SEQUENCE: 60

```
Ala Thr Gly Arg Leu Ala Ser Gln Ala Met Lys Lys Ile Glu Asp Lys
1               5                   10                  15

Val Arg Lys Ser Val Asp Gly Val Thr Thr Arg Asn Glu Met Glu Asn
            20                  25                  30

Ile Leu Gln Asn Leu Thr Leu Arg Ile Gln Val Ser Met Leu Gly Ala
        35                  40                  45

Lys Gly Gln Pro Ser Pro Gly Glu Gly Thr Arg Pro Arg Glu Ser Asn
    50                  55                  60

Asp Pro Asn Ala Thr Arg Arg Ala Arg Ser Arg Ser Arg Gly Arg Glu
65                  70                  75                  80

Ala Lys Lys Val Gln Ile Ser Asp
                85
```

<210> SEQ ID NO 61
<211> LENGTH: 324
<212> TYPE: PRT
<213> ORGANISM: artificial
<220> FEATURE:
<223> OTHER INFORMATION: conjugate DARC VHH (with restriction site) -
      glycine serine linker - EBV wt full length P18 antigen

<400> SEQUENCE: 61

```
Met Ala Gln Val Gln Leu Gln Glu Ser Gly Gly Gly Ser Val Gln

Val Tyr Leu Gln Met Asn Ser Leu Lys Pro Glu Asp Thr Ala Ile Tyr
                85                  90                  95

Tyr Cys Ala Ala Lys Arg Val Val Gly Gly Arg Tyr Cys Gly Gly Gly
            100                 105                 110

Val Ser Ser Trp Gly Gln Gly Thr Gln Val Thr Val Ser Ser Ala Ser
        115                 120                 125

Gly Gly Gly Gly Ser Gly Gly Gly Ser Gly Gly Gly Ser Gly
130                 135                 140

Gly Gly Gly Ser Met Ala Arg Arg Leu Pro Lys Pro Thr Leu Gln Gly
145                 150                 155                 160

Arg Leu Glu Ala Asp Phe Pro Asp Ser Pro Leu Leu Pro Lys Phe Gln
                165                 170                 175

Glu Leu Asn Gln Asn Asn Leu Pro Asn Asp Val Phe Arg Glu Ala Gln
                180                 185                 190

Arg Ser Tyr Leu Val Phe Leu Thr Ser Gln Phe Cys Tyr Glu Glu Tyr
            195                 200                 205

Val Gln Arg Thr Phe Gly Val Pro Arg Arg Gln Arg Ala Ile Asp Lys
        210                 215                 220

Arg Gln Arg Ala Ser Val Ala Gly Ala Gly Ala His Ala His Leu Gly
225                 230                 235                 240

Gly Ser Ser Ala Thr Pro Val Gln Gln Ala Gln Ala Ala Ala Ser Ala
                245                 250                 255

Gly Thr Gly Ala Leu Ala Ser Ser Ala Pro Ser Thr Ala Val Ala Gln
            260                 265                 270

Ser Ala Thr Pro Ser Val Ser Ser Ile Ser Ser Leu Arg Ala Ala
        275                 280                 285

Thr Ser Gly Ala Thr Ala Ala Ala Ser Ala Ala Ala Ala Val Asp Thr
290                 295                 300

Gly Ser Gly Gly Gly Gln Pro His Asp Thr Ala Pro Arg Gly Ala
305                 310                 315                 320

Arg Lys Lys Gln

<210> SEQ ID NO 62
<211> LENGTH: 324
<212> TYPE: PRT
<213> ORGANISM: artificial
<220> FEATURE:
<223> OTHER INFORMATION: conjugate DARC VHH (with restriction site) -
      glycine serine linker - EBV mutated P18 antigen (C56S)*

<400> SEQUENCE: 62

Met Ala Gln Val Gln Leu Gln Glu Ser Gly Gly Gly Ser Val Gln Ala
1               5                   10                  15

Gly Gly Ser Leu Arg Leu Ser Cys Ala Ala Ser Gly Tyr Ala Phe Ser
            20                  25                  30

Ser

```
Val Ser Ser Trp Gly Gln Gly Thr Gln Val Thr Val Ser Ser Ala Ser
            115                 120                 125

Gly Gly Gly Gly Ser Gly Gly Gly Ser Gly Gly Gly Ser Gly
130                 135                 140

Gly Gly Gly Ser Met Ala Arg Arg Leu Pro Lys Pro Thr Leu Gln Gly
145                 150                 155                 160

Arg Leu Glu Ala Asp Phe Pro Asp Ser Pro Leu Leu Pro Lys Phe Gln
                165                 170                 175

Glu Leu Asn Gln Asn Asn Leu Pro Asn Asp Val Phe Arg Glu Ala Gln
            180                 185                 190

Arg Ser Tyr Leu Val Phe Leu Thr Ser Gln Phe Ser Tyr Glu Glu Tyr
            195                 200                 205

Val Gln Arg Thr Phe Gly Val Pro Arg Arg Gln Arg Ala Ile Asp Lys
        210                 215                 220

Arg Gln Arg Ala Ser Val Ala Gly Ala Gly Ala His Ala His Leu Gly
225                 230                 235                 240

Gly Ser Ser Ala Thr Pro Val Gln Gln Ala Gln Ala Ala Ala Ser Ala
                245                 250                 255

Gly Thr Gly Ala Leu Ala Ser Ser Ala Pro Ser Thr Ala Val Ala Gln
            260                 265                 270

Ser Ala Thr Pro Ser Val Ser Ser Ile Ser Ser Leu Arg Ala Ala
            275                 280                 285

Thr Ser Gly Ala Thr Ala Ala Ala Ser Ala Ala Ala Ala Val Asp Thr
            290                 295                 300

Gly Ser Gly Gly Gly Gln Pro His Asp Thr Ala Pro Arg Gly Ala
305                 310                 315                 320

Arg Lys Lys Gln

<210> SEQ ID NO 63
<211> LENGTH: 304
<212> TYPE: PRT
<213> ORGANISM: artificial
<220> FEATURE:
<223> OTHER INFORMATION: conjugate DARC VHH (with restriction site) -
      EBV mutated P18 antigen (C56S)*

<400> SEQUENCE: 63

Met Ala Gln Val Gln Leu Gln Glu Ser Gly Gly Gly Ser Val Gln Ala
1               5                   10                  15

Gly Gly Ser Leu Arg Leu Ser Cys Ala Ala Ser Gly Tyr Ala Phe Ser
            20                  25                  30

Ser Tyr Cys Met Ala Trp Phe Arg Gln Val Pro Gly Lys Glu Arg Glu
        35                  40                  45

Gly Val Ala Ser Ile Asn Ser Asp Gly Glu Arg Arg Gly Tyr Ala Asp
    50                  55                  60

Ser Val Lys Gly Arg Phe Thr Val Ser Arg Asp Asn Ala Lys Asn Thr
65                  70                  75                  80

Val Tyr Leu Gln Met Asn Ser Leu Lys Pro Glu Asp Thr Ala Ile Tyr
                85                  90                  95

Tyr Cys Ala Ala Lys Arg Val Val Gly Gly Arg Tyr Cys Gly Gly Gly
            100                 105                 110

Val Ser Ser Trp Gly Gln Gly Thr Gln Val Thr Val Ser Ser Ala Ser
            115                 120                 125

Met Ala Arg Arg Leu Pro Lys Pro Thr Leu Gln Gly Arg Leu Glu Ala
        130                 135                 140
```

```
Asp Phe Pro Asp Ser Pro Leu Leu Pro Lys Phe Gln Glu Leu Asn Gln
145                 150                 155                 160

Asn Asn Leu Pro Asn Asp Val Phe Arg Glu Ala Gln Arg Ser Tyr Leu
            165                 170                 175

Val Phe Leu Thr Ser Gln Phe Ser Tyr Glu Glu Tyr Val Gln Arg Thr
        180                 185                 190

Phe Gly Val Pro Arg Arg Gln Arg Ala Ile Asp Lys Arg Gln Arg Ala
    195                 200                 205

Ser Val Ala Gly Ala Gly Ala His Ala His Leu Gly Gly Ser Ser Ala
210                 215                 220

Thr Pro Val Gln Gln Ala Gln Ala Ala Ala Ser Ala Gly Thr Gly Ala
225                 230                 235                 240

Leu Ala Ser Ser Ala Pro Ser Thr Ala Val Ala Gln Ser Ala Thr Pro
                245                 250                 255

Ser Val Ser Ser Ser Ile Ser Ser Leu Arg Ala Ala Thr Ser Gly Ala
            260                 265                 270

Thr Ala Ala Ala Ser Ala Ala Ala Val Asp Thr Gly Ser Gly Gly
        275                 280                 285

Gly Gly Gln Pro His Asp Thr Ala Pro Arg Gly Ala Arg Lys Lys Gln
    290                 295                 300

<210> SEQ ID NO 64
<211> LENGTH: 235
<212> TYPE: PRT
<213> ORGANISM: artificial
<220> FEATURE:
<223> OTHER INFORMATION: conjugate DARC VHH (with restriction site) -
      EBV P18 antigen fragment F2

<400> SEQUENCE: 64

Met Ala Gln Val Gln Leu Gln Glu Ser Gly Gly Gly Ser Val Gln Ala
1               5                   10                  15

Gly Gly Ser Leu Arg Leu Ser Cys Ala Ala Ser Gly Tyr Ala Phe Ser
            20                  25                  30

Ser Tyr Cys Met Ala Trp Phe Arg Gln Val Pro Gly Lys Glu Arg Glu
        35                  40                  45

Gly Val Ala Ser Ile Asn Ser Asp Gly Glu Arg Arg Gly Tyr Ala Asp
    50                  55                  60

Ser Val Lys Gly Arg Phe Thr Val Ser Arg Asp Asn Ala Lys Asn Thr
65                  70                  75                  80

Val Tyr Leu Gln Met Asn Ser Leu Lys Pro Glu Asp Thr Ala Ile Tyr
            85                  90                  95

Tyr Cys Ala Ala Lys Arg Val Val Gly Gly Arg Tyr Cys Gly Gly Gly
        100                 105                 110

Val Ser Ser Trp Gly Gln Gly Thr Gln Val Thr Val Ser Ser Ala Ser
    115                 120                 125

Arg Gln Arg Ala Ile Asp Lys Arg Gln Arg Ala Ser Val Ala Gly Ala
130                 135                 140

Gly Ala His Ala His Leu Gly Gly Ser Ser Ala Thr Pro Val Gln Gln
145                 150                 155                 160

Ala Gln Ala Ala Ala Ser Ala Gly Thr Gly Ala Leu Ala Ser Ser Ala
            165                 170                 175

Pro Ser Thr Ala Val Ala Gln Ser Ala Thr Pro Ser Val Ser Ser Ser
        180                 185                 190

Ile Ser Ser Leu Arg Ala Ala Thr Ser Gly Ala Thr Ala Ala Ala Ser
    195                 200                 205
```

```
Ala Ala Ala Ala Val Asp Thr Gly Ser Gly Gly Gly Gln Pro His
    210                 215                 220

Asp Thr Ala Pro Arg Gly Ala Arg Lys Lys Gln
225                 230                 235

<210> SEQ ID NO 65
<211> LENGTH: 220
<212> TYPE: PRT
<213> ORGANISM: artificial
<220> FEATURE:
<223> OTHER INFORMATION: conjugate DARC VHH (with restriction site) -
      EBV P18 antigen fragment F3'

<400> SEQUENCE: 65

Met Ala Gln Val Gln Leu Gln Glu Ser Gly Gly Gly Ser Val Gln Ala
1               5                   10                  15

Gly Gly Ser Leu Arg Leu Ser Cys Ala Ala Ser Gly Tyr Ala Phe Ser
            20                  25                  30

Ser Tyr Cys Met Ala Trp Phe Arg Gln Val Pro Gly Lys Glu Arg Glu
        35                  40                  45

Gly Val Ala Ser Ile Asn Ser Asp Gly Glu Arg Arg Gly Tyr Ala Asp
    50                  55                  60

Ser Val Lys Gly Arg Phe Thr Val Ser Arg Asp Asn Ala Lys Asn Thr
65                  70                  75                  80

Val Tyr Leu Gln Met Asn Ser Leu Lys Pro Glu Asp Thr Ala Ile Tyr
                85                  90                  95

Tyr Cys Ala Ala Lys Arg Val Val Gly Gly Arg Tyr Cys Gly Gly Gly
            100                 105                 110

Val Ser Ser Trp Gly Gln Gly Thr Gln Val Thr Val Ser Ser Ala Ser
        115                 120                 125

Ala Gly Ala His Ala His Leu Gly Gly Ser Ser Ala Thr Pro Val Gln
    130                 135                 140

Gln Ala Gln Ala Ala Ala Ser Ala Gly Thr Gly Ala Leu Ala Ser Ser
145                 150                 155                 160

Ala Pro Ser Thr Ala Val Ala Gln Ser Ala Thr Pro Ser Val Ser Ser
                165                 170                 175

Ser Ile Ser Ser Leu Arg Ala Ala Thr Ser Gly Ala Thr Ala Ala Ala
            180                 185                 190

Ser Ala Ala Ala Ala Val Asp Thr Gly Ser Gly Gly Gly Gly Gln Pro
        195                 200                 205

His Asp Thr Ala Pro Arg Gly Ala Arg Lys Lys Gln
    210                 215                 220

<210> SEQ ID NO 66
<211> LENGTH: 151
<212> TYPE: PRT
<213> ORGANISM: artificial
<220> FEATURE:
<223> OTHER INFORMATION: conjugate DARC VHH (with restriction site) -
      EBV P18 antigen fragment F4

<400> SEQUENCE: 66

Met Ala Gln Val Gln Leu Gln Glu Ser Gly Gly Gly Ser Val Gln Ala
1               5                   10                  15

Gly Gly Ser Leu Arg Leu Ser Cys Ala Ala Ser Gly Tyr Ala Phe Ser
            20                  25                  30

Ser Tyr Cys Met Ala Trp Phe Arg Gln Val Pro Gly Lys Glu Arg Glu
        35                  40                  45
```

```
Gly Val Ala Ser Ile Asn Ser Asp Gly Glu Arg Arg Gly Tyr Ala Asp
     50                  55                  60

Ser Val Lys Gly Arg Phe Thr Val Ser Arg Asp Asn Ala Lys Asn Thr
 65                  70                  75                  80

Val Tyr Leu Gln Met Asn Ser Leu Lys Pro Glu Asp Thr Ala Ile Tyr
                     85                  90                  95

Tyr Cys Ala Ala Lys Arg Val Val Gly Arg Tyr Cys Gly Gly
                100                 105                 110

Val Ser Ser Trp Gly Gln Gly Thr Gln Val Thr Val Ser Ser Ala Ser
             115                 120                 125

Val Asp Thr Gly Ser Gly Gly Gly Gln Pro His Asp Thr Ala Pro
    130                 135                 140

Arg Gly Ala Arg Lys Lys Gln
145                 150
```

<210> SEQ ID NO 67
<211> LENGTH: 232
<212> TYPE: PRT
<213> ORGANISM: artificial
<220> FEATURE:
<223> OTHER INFORMATION: conjugate VAR2CSA VHH (with restriction site)-
      EBV P18 antigen fragment F2

<400> SEQUENCE: 67

```
Met Ala Gln Val Gln Leu Gln Glu Ser Gly Gly Gly Leu Val Gln Ala
  1               5                  10                  15

Gly Gly Ser Leu Arg Leu Ser Cys Ala Phe Ser Gly Ser Ile Phe Lys
             20                  25                  30

Met Gly Trp Phe Arg Gln Ala Pro Gly Lys Glu Arg Glu Phe Val Ala
         35                  40                  45

Ala Ile Arg Trp Ser Gly Gly Ser Thr Tyr Tyr Ala Asp Ser Val Lys
     50                  55                  60

Gly Arg Phe Thr Ile Ser Arg Asp Asn Ala Lys Asn Thr Val Tyr Leu
 65                  70                  75                  80

Gln Met Asp Ser Leu Lys Pro Glu Asp Thr Ala Val Tyr Tyr Cys Ala
                 85                  90                  95

Ala Thr Trp Asp Leu Ala Gly Trp Asn Thr Val Asp Glu Tyr Asp Tyr
                100                 105                 110

Trp Gly Gln Gly Thr Gln Val Thr Val Ser Ser Ala Ser Arg Gln Arg
             115                 120                 125

Ala Ile Asp Lys Arg Gln Arg Ala Ser Val Ala Gly Ala Gly Ala His
    130                 135                 140

Ala His Leu Gly Gly Ser Ser Ala Thr Pro Val Gln Gln Ala Gln Ala
145                 150                 155                 160

Ala Ala Ser Ala Gly Thr Gly Ala Leu Ala Ser Ser Ala Pro Ser Thr
                165                 170                 175

Ala Val Ala Gln Ser Ala Thr Pro Ser Val Ser Ser Ser Ile Ser Ser
                180                 185                 190

Leu Arg Ala Ala Thr Ser Gly Ala Thr Ala Ala Ala Ser Ala Ala Ala
                195                 200                 205

Ala Val Asp Thr Gly Ser Gly Gly Gly Gln Pro His Asp Thr Ala
    210                 215                 220

Pro Arg Gly Ala Arg Lys Lys Gln
225                 230
```

<210> SEQ ID NO 68
<211> LENGTH: 217
<212> TYPE: PRT
<213> ORGANISM: artificial
<220> FEATURE:
<223> OTHER INFORMATION: conjugate VAR2CSA VHH (with restriction site)-
      EBV P18 antigen fragment F3'

<400> SEQUENCE: 68

Met Ala Gln Val Gln Leu Gln Glu Ser Gly Gly Gly Leu Val Gln Ala
1               5                   10                  15

Gly Gly Ser Leu Arg Leu Ser Cys Ala Phe Ser Gly Ser Ile Phe Lys
            20                  25                  30

Met Gly Trp Phe Arg Gln Ala Pro Gly Lys Glu Arg Glu Phe Val Ala
        35                  40                  45

Ala Ile Arg Trp Ser Gly Gly Ser Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asp Ser Leu Lys Pro Glu Asp Thr Ala Val Tyr Tyr Cys Ala
                85                  90                  95

Ala Thr Trp Asp Leu Ala Gly Trp Asn Thr Val Asp Gly Tyr Asp Tyr
            100                 105                 110

Trp Gly Gln Gly Thr Gln Val Thr Val Ser Ser Ala Ser Ala Gly Ala
        115                 120                 125

His Ala His Leu Gly Gly Ser Ser Ala Thr Pro Val Gln Gln Ala Gln
    130                 135                 140

Ala Ala Ala Ser Ala Gly Thr Gly Ala Leu Ala Ser Ser Ala Pro Ser
145                 150                 155                 160

Thr Ala Val Ala Gln Ser Ala Thr Pro Ser Val Ser Ser Ile Ser
                165                 170                 175

Ser Leu Arg Ala Ala Thr Ser Gly Ala Thr Ala Ala Ser Ala Ala
            180                 185                 190

Ala Ala Val Asp Thr Gly Ser Gly Gly Gly Gln Pro His Asp Thr
        195                 200                 205

Ala Pro Arg Gly Ala Arg Lys Lys Gln
    210                 215

<210> SEQ ID NO 69
<211> LENGTH: 148
<212> TYPE: PRT
<213> ORGANISM: artificial
<220> FEATURE:
<223> OTHER INFORMATION: conjugate VAR2CSA VHH (with restriction site) -
      EBV P18 antigen fragment F4

<400> SEQUENCE: 69

```
Met Ala Gln Val Gln Leu Gln Glu Ser Gly Gly Gly Leu Val Gln Ala
1               5                   10                  15

Gly Gly Ser Leu Arg Leu Ser Cys Ala Phe Ser Gly Ser Ile Phe Lys
            20                  25                  30

Met Gly Trp Phe Arg Gln Ala Pro Gly Lys Glu Arg Glu Phe Val Ala
        35                  40                  45

Ala Ile Arg Trp Ser Gly Gly Ser Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asp Ser Leu Lys Pro Glu Asp Thr Ala Val Tyr Tyr Cys Ala
```

```
                85                  90                  95
Ala Thr Trp Asp Leu Ala Gly Trp Asn Thr Val Asp Glu Tyr Asp Tyr
            100                 105                 110

Trp Gly Gln Gly Thr Gln Val Thr Val Ser Ser Ala Ser Val Asp Thr
            115                 120                 125

Gly Ser Gly Gly Gly Gln Pro His Asp Thr Ala Pro Arg Gly Ala
            130                 135                 140

Arg Lys Lys Gln
145

<210> SEQ ID NO 70
<211> LENGTH: 310
<212> TYPE: PRT
<213> ORGANISM: artificial
<220> FEATURE:
<223> OTHER INFORMATION: conjugate DARC VHH (with restriction site) -
      glycine serine linker - EBV wt full length P23 ant

```
Asn Ala Thr Arg Arg Ala Arg Ser Arg Ser Arg Gly Arg Glu Ala Lys
    290                 295                 300

Lys Val Gln Ile Ser Asp
305                 310

<210> SEQ ID NO 71
<211> LENGTH: 310
<212> TYPE: PRT
<213> ORGANISM: artificial
<220> FEATURE:
<223> OTHER INFORMATION: conjugate DARC VHH (with restriction site) -
      glycine serine linker - EBV mutated P23 antigen (C46S)*

<400> SEQUENCE: 71

Met Ala Gln Val Gln Leu Gln Glu Ser Gly Gly Ser Val Gln Ala
1               5                   10                  15

Gly Gly Ser Leu Arg Leu Ser Cys Ala Ala Ser Gly Tyr Ala Phe Ser
                20                  25                  30

Ser Tyr Cys Met Ala Trp Phe Arg Gln Val Pro Gly Lys Glu Arg Glu
            35                  40                  45

Gly Val Ala Ser Ile Asn Ser Asp Gly Glu Arg Arg Gly Tyr Ala Asp
        50                  55                  60

Ser Val Lys Gly Arg Phe Thr Val Ser Arg Asp Asn Ala Lys Asn Thr
65                  70                  75                  80

Val Tyr Leu Gln Met Asn Ser Leu Lys Pro Glu Asp Thr Ala Ile Tyr
                85                  90                  95

Tyr Cys Ala Ala Lys Arg Val Val Gly Gly Arg Tyr Cys Gly Gly Gly
            100                 105                 110

Val Ser Ser Trp Gly Gln Gly Thr Gln Val Thr Val Ser Ser Ala Ser
        115                 120                 125

Gly Gly Gly Gly Ser Gly Gly Gly Ser Gly Gly Gly Ser Gly
        130                 135                 140

Gly Gly Gly Ser Met Ser Ala Pro Arg Lys Val Arg Leu Pro Ser Val
145                 150                 155                 160

Lys Ala Val Asp Met Ser Met Glu Asp Met Ala Ala Arg Leu Ala Arg
                165                 170                 175

Leu Glu Ser Glu Asn Lys Ala Leu Lys Gln Gln Val Leu Arg Gly Gly
            180                 185                 190

Ala Ser Ala Ser Ser Thr Ser Val Pro Ser Ala Pro Val Pro Pro Pro
        195                 200                 205

Glu Pro Leu Thr Ala Arg Gln Arg Glu Val Met Ile Thr Gln Ala Thr
210                 215                 220

Gly Arg Leu Ala Ser Gln Ala Met Lys Lys Ile Glu Asp Lys Val Arg
225                 230                 235                 240

Lys Ser Val Asp Gly Val Thr Thr Arg Asn Glu Met Glu Asn Ile Leu
                245                 250                 255

Gln Asn Leu Thr Leu Arg Ile Gln Val Ser Met Leu Gly Ala Lys Gly
            260                 265                 270

Gln Pro Ser Pro Gly Glu Gly Thr Arg Pro Arg Glu Ser Asn Asp Pro
        275                 280                 285

Asn Ala Thr Arg Arg Ala Arg Ser Arg Ser Arg Gly Arg Glu Ala Lys
    290                 295                 300

Lys Val Gln Ile Ser Asp
305                 310

<210> SEQ ID NO 72
```

<211> LENGTH: 290
<212> TYPE: PRT
<213> ORGANISM: artificial
<220> FEATURE:
<223> OTHER INFORMATION: conjugate DARC VHH (with restriction site) -
      EBV mutated P23 antigen(C46S)*

<400> SEQUENCE: 72

Met Ala Gln Val G

```
Gly Gly Ser Leu Arg Leu Ser Cys Ala Ala Ser Gly Tyr Ala Phe Ser
             20                  25                  30

Ser Tyr Cys Met Ala Trp Phe Arg Gln Val Pro Gly Lys Glu Arg Glu
         35                  40                  45

Gly Val Ala Ser Ile Asn Ser Asp Gly Glu Arg Arg Gly Tyr Ala Asp
     50                  55                  60

Ser Val Lys Gly Arg Phe Thr Val Ser Arg Asp Asn Ala Lys Asn Thr
65                  70                  75                  80

Val Tyr Leu Gln Met Asn Ser Leu Lys Pro Glu Asp Thr Ala Ile Tyr
                 85                  90                  95

Tyr Cys Ala Ala Lys Arg Val Val Gly Gly Arg Tyr Cys Gly Gly Gly
            100                 105                 110

Val Ser Ser Trp Gly Gln Gly Thr Gln Val Thr Val Ser Ser Ala Ser
            115                 120                 125

Ala Thr Gly Arg Leu Ala Ser Gln Ala Met Lys Lys Ile Glu Asp Lys
    130                 135                 140

Val Arg Lys Ser Val Asp Gly Val Thr Thr Arg Asn Glu Met Glu Asn
145                 150                 155                 160

Ile Leu Gln Asn Leu Thr Leu Arg Ile Gln Val Ser Met Leu Gly Ala
                165                 170                 175

Lys Gly Gln Pro Ser Pro Gly Glu Gly Thr Arg Pro Arg Glu Ser Asn
            180                 185                 190

Asp Pro Asn Ala Thr Arg Arg Ala Arg Ser Arg Ser Arg Gly Arg Glu
        195                 200                 205

Ala Lys Lys Val Gln Ile Ser Asp
    210                 215

<210> SEQ ID NO 74
<211> LENGTH: 188
<212> TYPE: PRT
<213> ORGANISM: artificial
<220> FEATURE:
<223> OTHER INFORMATION: conjugate DARC VHH (with restriction site) -
      EBV P23 antigen fragment F3

<400> SEQUENCE: 74

Met Ala Gln Val Gln Leu Gln Glu Ser Gly Gly Gly Ser Val Gln Ala
1               5                   10                  15

Gly Gly Ser Leu Arg Leu Ser Cys Ala Ala Ser Gly Tyr Ala Phe Ser
             20                  25                  30

Ser Tyr Cys Met Ala Trp Phe Arg Gln Val Pro Gly Lys Glu Arg Glu
         35                  40                  45

Gly Val Ala Ser Ile Asn Ser Asp Gly Glu Arg Arg Gly Tyr Ala Asp
     50                  55                  60

Ser Val Lys Gly Arg Phe Thr Val Ser Arg Asp Asn Ala Lys Asn Thr
65                  70                  75                  80

Val Tyr Leu Gln Met Asn Ser Leu Lys Pro Glu Asp Thr Ala Ile Tyr
                 85                  90                  95

Tyr Cys Ala Ala Lys Arg Val Val Gly Gly Arg Tyr Cys Gly Gly Gly
            100                 105                 110

Val Ser Ser Trp Gly Gln Gly Thr Gln Val Thr Val Ser Ser Ala Ser
            115                 120                 125

Glu Met Glu Asn Ile Leu Gln Asn Leu Thr Leu Arg Ile Gln Val Ser
    130                 135                 140

Met Leu Gly Ala Lys Gly Gln Pro Ser Pro Gly Glu Gly Thr Arg Pro
```

```
                145                 150                 155                 160
Arg Glu Ser Asn Asp Pro Asn Ala Thr Arg Arg Ala Arg Ser Arg Ser
                    165                 170                 175
Arg Gly Arg Glu Ala Lys Lys Val Gln Ile Ser Asp
        180                 185

<210> SEQ ID NO 75
<211> LENGTH: 72
<212> TYPE: PRT
<213> ORGANISM: artificial
<220> FEATURE:
<223> OTHER INFORMATION: Consensus EBV P18 antigen fragment F3
<220> FEATURE:
<221> NAME/KEY: VARIANT
<222> LOCATION: (22)..(22)
<223> OTHER INFORMATION: Ala can be replaced by Val
<220> FEATURE:
<221> NAME/KEY: VARIANT
<222> LOCATION: (32)..(32)
<223> OTHER INFORMATION: Ser can be replaced by Asn
<220> FEATURE:
<221> NAME/KEY: VARIANT
<222> LOCATION: (44)..(44)
<223> OTHER INFORMATION: Ala can be absent
<220> FEATURE:
<221> NAME/KEY: VARIANT
<222> LOCATION: (45)..(45)
<223> OTHER INFORMATION: Ser can be absent
<220> FEATURE:
<221> NAME/KEY: VARIANT
<222> LOCATION: (61)..(61)
<223> OTHER INFORMATION: Gln can be replaced by His

<400> SEQUENCE: 75

Ala Ala Ser Ala Gly Thr Gly Ala Leu Ala Ser Ser Ala Pro Ser Thr
1               5                   10                  15

Ala Val Ala Gln Ser Ala Thr Pro Ser Val Ser Ser Ile Ser Ser
                20                  25                  30

Leu Arg Ala Ala Thr Ser Gly Ala Thr Ala Ala Ala Ser Ala Ala Ala
        35                  40                  45

Ala Val Asp Thr Gly Ser Gly Gly Gly Gln Pro Gln Asp Thr Ala
    50                  55                  60

Pro Arg Gly Ala Arg Lys Lys Gln
65                  70

<210> SEQ ID NO 76
<211> LENGTH: 72
<212> TYPE: PRT
<213> ORGANISM: artificial
<220> FEATURE:
<223> OTHER INFORMATION: EBV P18 antigen fragment F3

<400> SEQUENCE: 76

Ala Ala Ser Ala Gly Thr Gly Ala Leu Ala Ser Ser Ala Pro Ser Thr
1               5                   10                  15

Ala Val Ala Gln Ser Ala Thr Pro Ser Val Ser Ser Ile Ser Ser
                20                  25                  30

Leu Arg Ala Ala Thr Ser Gly Ala Thr Ala Ala Ala Ser Ala Ala Ala
        35                  40                  45

Ala Val Asp Thr Gly Ser Gly Gly Gly Gln Pro His Asp Thr Ala
    50                  55                  60

Pro Arg Gly Ala Arg Lys Lys Gln
65                  70
```

-continued

```
<210> SEQ ID NO 77
<211> LENGTH: 200
<212> TYPE: PRT
<213> ORGANISM: artificial
<220> FEATURE:
<223> OTHER INFORMATION: conjugate DARC VHH (with restriction site) -
      EBV P18 antigen fragment F3

<400> SEQUENCE: 77
```

Met Ala Gln Val Gln Leu Gln Glu Ser Gly Gly Gly Ser Val Gln Ala
1               5                   10                  15

Gly Gly Ser Leu Arg Leu Ser Cys Ala Ala Ser Gly Tyr Ala Phe Ser
            20                  25                  30

Ser Tyr Cys Met Ala Trp Phe Arg Gln Val Pro Gly Lys Glu Arg Glu
        35                  40                  45

Gly Val Ala Ser Ile Asn Ser Asp Gly Glu Arg Arg Gly Tyr Ala Asp
    50                  55                  60

Ser Val Lys Gly Arg Phe Thr Val Ser Arg Asp Asn Ala Lys Asn Thr
65                  70                  75                  80

Val Tyr Leu Gln Met Asn Ser Leu Lys Pro Glu Asp Thr Ala Ile Tyr
                85                  90                  95

Tyr Cys Ala Ala Lys Arg Val Val Gly Gly Arg Tyr Cys Gly Gly Gly
            100                 105                 110

Val Ser Ser Trp Gly Gln Gly Thr Gln Val Thr Val Ser Ser Ala Ser
        115                 120                 125

Ala Ala Ser Ala Gly Thr Gly Ala Leu Ala Ser Ser Ala Pro Ser Thr
    130                 135                 140

Ala Val Ala Gln Ser Ala Thr Pro Ser Val Ser Ser Ile Ser Ser Ser
145                 150                 155                 160

Leu Arg Ala Ala Thr Ser Gly Ala Thr Ala Ala Ser Ala Ala Ala
                165                 170                 175

Ala Val Asp Thr Gly Ser Gly Gly Gly Gln Pro His Asp Thr Ala
            180                 185                 190

Pro Arg Gly Ala Arg Lys Lys Gln
            195                 200

```
<210> SEQ ID NO 78
<211> LENGTH: 197
<212> TYPE: PRT
<213> ORGANISM: artificial
<220> FEATURE:
<223> OTHER INFORMATION: conjugate VAR2CSA VHH (with restriction site)-
      EBV P18 antigen fragment F3

<400> SEQUENCE: 78
```

Met Ala Gln Val Gln Leu Gln Glu Ser Gly Gly Gly Leu Val Gln Ala
1               5                   10                  15

Gly Gly Ser Leu Arg Leu Ser Cys Ala Phe Ser Gly Ser Ile Phe Lys
            20                  25                  30

Met Gly Trp Phe Arg Gln Ala Pro Gly Lys Glu Arg Glu Phe Val Ala
        35                  40                  45

Ala Ile Arg Trp Ser Gly Gly Ser Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asp Ser Leu Lys Pro Glu Asp Thr Ala Val Tyr Tyr Cys Ala
                85                  90                  95

Ala Thr Trp Asp Leu Ala Gly Trp Asn Thr Val Asp Glu Tyr Asp Tyr

```
            100                 105                 110
Trp Gly Gln Gly Thr Gln Val Thr Val Ser Ser Ala Ser Ala Ala Ser
        115                 120                 125

Ala Gly Thr Gly Ala Leu Ala Ser Ser Ala Pro Ser Thr Ala Val Ala
    130                 135                 140

Gln Ser Ala Thr Pro Ser Val Ser Ser Ser Ile Ser Ser Leu Arg Ala
145                 150                 155                 160

Ala Thr Ser Gly Ala Thr Ala Ala Ala Ser Ala Ala Ala Ala Val Asp
                165                 170                 175

Thr Gly Ser Gly Gly Gly Gly Gln Pro His Asp Thr Ala Pro Arg Gly
            180                 185                 190

Ala Arg Lys Lys Gln
        195

<210> SEQ ID NO 79
<211> LENGTH: 270
<212> TYPE: PRT
<213> ORGANISM: artificial
<220> FEATURE:
<223> OTHER INFORMATION: conjugate EPCR amino-acid 18-210 - EBV P18
      antigen fragment F3

<400> SEQUENCE: 79

Ser Asp Gly Leu Gln Arg Leu His Met Leu Gln Ile Ser Tyr Phe Arg
1               5                   10                  15

Asp Pro Tyr His Val Trp Tyr Gln Gly Asn Ala Ser Leu Gly Gly His
            20                  25                  30

Leu Thr His Val Leu Glu Gly Pro Asp Thr Asn Thr Thr Ile Ile Gln
        35                  40                  45

Leu Gln Pro Leu Gln Glu Pro Glu Ser Trp Ala Arg Thr Gln Ser Gly
    50                  55                  60

Leu Gln Ser Tyr Leu Leu Gln Phe His Gly Leu Val Arg Leu Val His
65                  70                  75                  80

Gln Glu Arg Thr Leu Ala Phe Pro Leu Thr Ile Arg Cys Phe Leu Gly
                85                  90                  95

Cys Glu Leu Pro Pro Glu Gly Ser Arg Ala His Val Phe Phe Glu Val
            100                 105                 110

Ala Val Asn Gly Ser Ser Phe Val Ser Phe Arg Pro Glu Arg Ala Leu
        115                 120                 125

Trp Gln Ala Asp Thr Gln Val Thr Ser Gly Val Val Thr Phe Thr Leu
    130                 135                 140

Gln Gln Leu Asn Ala Tyr Asn Arg Thr Arg Tyr Glu Leu Arg Glu Phe
145                 150                 155                 160

Leu Glu Asp Thr Cys Val Gln Tyr Val Gln Lys His Ile Ser Ala Glu
                165                 170                 175

Asn Thr Lys Gly Ser Gln Thr Ser Arg Ser Tyr Thr Ser Leu Val Leu
            180                 185                 190

Gly Val Leu Val Gly Ser Ala Ala Ser Ala Gly Thr Gly Ala Leu Ala
        195                 200                 205

Ser Ser Ala Pro Ser Thr Ala Val Ala Gln Ser Ala Thr Pro Ser Val
    210                 215                 220

Ser Ser Ser Ile Ser Ser Leu Arg Ala Ala Thr Ser Gly Ala Thr Ala
225                 230                 235                 240

Ala Ala Ser Ala Ala Ala Ala Val Asp Thr Gly Ser Gly Gly Gly Gly
                245                 250                 255

```
                  Gln Pro His Asp Thr Ala Pro Arg Gly Ala Arg Lys Lys Gln
                              260                 265                 270

<210> SEQ ID NO 80
<211> LENGTH: 245
<212> TYPE: PRT
<213> ORGANISM: artificial
<220> FEATURE:
<223> OTHER INFORMATION: Anti-CD20 scFv

<400> SEQUENCE: 80

Met Ala Gln Ala Tyr Leu Gln Gln Ser Gly Ala Glu Leu Val Arg Pro
1               5                   10                  15

Gly Ala Ser Val Lys Met Ser Cys Lys Ala Ser Gly Tyr Thr Phe Thr
            20                  25                  30

Ser Tyr Asn Met His Trp Val Lys Gln Thr Pro Arg Gln Gly Leu Glu
        35                  40                  45

Trp Ile Gly Ala Ile Tyr Pro Gly Asn Gly Asp Thr Ser Tyr Asn Gln
    50                  55                  60

Lys Phe Lys Gly Lys Ala Thr Leu Thr Val Asp Lys Ser Ser Ser Thr
65                  70                  75                  80

Ala Tyr Met Gln Leu Ser Ser Leu Thr Ser Glu Asp Ser Ala Val Tyr
                85                  90                  95

Phe Cys Ala Arg Val Val Tyr Tyr Ser Asn Ser Tyr Trp Tyr Phe Asp
            100                 105                 110

Val Trp Gly Thr Gly Thr Thr Val Thr Val Ser Ser Gly Gly Gly Gly
        115                 120                 125

Ser Gly Gly Gly Gly Ser Gly Gly Gly Gly Ser Asp Ile Val Leu Ser
    130                 135                 140

Gln Ser Pro Ala Ile Leu Ser Ala Ser Pro Gly Glu Lys Val Thr Met
145                 150                 155                 160

Thr Cys Arg Ala Ser Ser Ser Val Ser Tyr Met His Trp Tyr Gln Gln
                165                 170                 175

Lys Pro Gly Ser Ser Pro Lys Pro Trp Ile Tyr Ala Pro Ser Asn Leu
            180                 185                 190

Ala Ser Gly Val Pro Ala Arg Phe Ser Gly Ser Gly Ser Gly Thr Ser
        195                 200                 205

Tyr Ser Leu Thr Ile Ser Arg Val Glu Ala Glu Asp Ala Ala Thr Tyr
    210                 215                 220

Tyr Cys Gln Gln Trp Ser Phe Asn Pro Pro Thr Phe Gly Ala Gly Thr
225                 230                 235                 240

Lys Leu Glu Leu Lys
                245

<210> SEQ ID NO 81
<211> LENGTH: 319
<212> TYPE: PRT
<213> ORGANISM: artificial
<220> FEATURE:
<223> OTHER INFORMATION: Anti-CD20 scFv - EBV P18 antigen fragment F3

<400> SEQUENCE: 81

Met Ala Gln Ala Tyr Leu Gln Gln Ser Gly Ala Glu Leu Val Arg Pro
1               5                   10                  15

Gly Ala Ser Val Lys Met Ser Cys Lys Ala Ser Gly Tyr Thr Phe Thr
            20                  25                  30

Ser Tyr Asn Met His Trp Val Lys Gln Thr Pro Arg Gln Gly Leu Glu
        35                  40                  45
```

```
Trp Ile Gly Ala Ile Tyr Pro Gly Asn Gly Asp Thr Ser Tyr Asn Gln
 50                  55                  60

Lys Phe Lys Gly Lys Ala Thr Leu Thr Val Asp Lys Ser Ser Ser Thr
 65                  70                  75                  80

Ala Tyr Met Gln Leu Ser Ser Leu Thr Ser Glu Asp Ser Ala Val Tyr
                 85                  90                  95

Phe Cys Ala Arg Val Val Tyr Tyr Ser Asn Ser Tyr Trp Tyr Phe Asp
                100                 105                 110

Val Trp Gly Thr Gly Thr Thr Val Thr Val Ser Ser Gly Gly Gly Gly
            115                 120                 125

Ser Gly Gly Gly Gly Ser Gly Gly Gly Ser Asp Ile Val Leu Ser
            130                 135                 140

Gln Ser Pro Ala Ile Leu Ser Ala Ser Pro Gly Glu Lys Val Thr Met
145                 150                 155                 160

Thr Cys Arg Ala Ser Ser Ser Val Ser Tyr Met His Trp Tyr Gln Gln
                165                 170                 175

Lys Pro Gly Ser Ser Pro Lys Pro Trp Ile Tyr Ala Pro Ser Asn Leu
                180                 185                 190

Ala Ser Gly Val Pro Ala Arg Phe Ser Gly Ser Gly Ser Gly Thr Ser
                195                 200                 205

Tyr Ser Leu Thr Ile Ser Arg Val Glu Ala Glu Asp Ala Ala Thr Tyr
            210                 215                 220

Tyr Cys Gln Gln Trp Ser Phe Asn Pro Pro Thr Phe Gly Ala Gly Thr
225                 230                 235                 240

Lys Leu Glu Leu Lys Ala Ser Ala Ala Ser Ala Gly Thr Gly Ala Leu
                245                 250                 255

Ala Ser Ser Ala Pro Ser Thr Ala Val Ala Gln Ser Ala Thr Pro Ser
                260                 265                 270

Val Ser Ser Ile Ser Ser Leu Arg Ala Ala Thr Ser Gly Ala Thr
            275                 280                 285

Ala Ala Ala Ser Ala Ala Ala Val Asp Thr Gly Ser Gly Gly Gly
            290                 295                 300

Gly Gln Pro His Asp Thr Ala Pro Arg Gly Ala Arg Lys Lys Gln
305                 310                 315

<210> SEQ ID NO 82
<211> LENGTH: 1016
<212> TYPE: PRT
<213> ORGANISM: artificial
<220> FEATURE:
<223> OTHER INFORMATION: VAR2CSA

<400> SEQUENCE: 82

Met Asp Lys Ser Ser Ile Ala Asn Lys Ile Glu Ala Tyr Leu Gly Ala
  1               5                  10                  15

Lys Ser Asp Asp Ser Lys Ile Asp Gln Ser Leu Lys Ala Asp Pro Ser
                 20                  25                  30

Glu Val Gln Tyr Tyr Gly Ser Gly Gly Asp Gly Tyr Tyr Leu Arg Lys
             35                  40                  45

Asn Ile Cys Lys Ile Thr Val Asn His Ser Asp Ser Gly Thr Asn Asp
 50                  55                  60

Pro Cys Asp Arg Ile Pro Pro Tyr Gly Asn Asp Gln Trp Lys
 65                  70                  75                  80

Cys Ala Ile Ile Leu Ser Lys Val Ser Glu Lys Pro Glu Asn Val Phe
                 85                  90                  95
```

```
Val Pro Pro Arg Arg Gln Arg Met Cys Ile Asn Asn Leu Glu Lys Leu
        100                 105                 110

Asn Val Asp Lys Ile Arg Asp Lys His Ala Phe Leu Ala Asp Val Leu
        115                 120                 125

Leu Thr Ala Arg Asn Glu Gly Glu Arg Ile Val Gln Asn His Pro Asp
        130                 135                 140

Thr Asn Ser Ser Asn Val Cys Asn Ala Leu Glu Arg Ser Phe Ala Asp
145                 150                 155                 160

Ile Ala Asp Ile Ile Arg Gly Thr Asp Leu Trp Lys Gly Thr Asn Ser
                165                 170                 175

Asn Leu Glu Gln Asn Leu Lys Gln Met Phe Ala Lys Ile Arg Glu Asn
        180                 185                 190

Asp Lys Val Leu Gln Asp Lys Tyr Pro Lys Asp Gln Asn Tyr Arg Lys
        195                 200                 205

Leu Arg Glu Asp Trp Trp Asn Ala Asn Arg Gln Lys Val Trp Glu Val
210                 215                 220

Ile Thr Cys Gly Ala Arg Ser Asn Asp Leu Leu Ile Lys Arg Gly Trp
225                 230                 235                 240

Arg Thr Ser Gly Lys Ser Asn Gly Asp Asn Lys Leu Glu Leu Cys Arg
                245                 250                 255

Lys Cys Gly His Tyr Glu Glu Lys Val Pro Thr Lys Leu Asp Tyr Val
        260                 265                 270

Pro Gln Phe Leu Arg Trp Leu Thr Glu Trp Ile Glu Asp Phe Tyr Arg
        275                 280                 285

Glu Lys Gln Asn Leu Ile Asp Asp Met Glu Arg His Arg Glu Glu Cys
        290                 295                 300

Thr Ser Glu Asp His Lys Ser Lys Glu Gly Thr Ser Tyr Cys Ser Thr
305                 310                 315                 320

Cys Lys Asp Lys Cys Lys Lys Tyr Cys Glu Cys Val Lys Lys Trp Lys
                325                 330                 335

Ser Glu Trp Glu Asn Gln Lys Asn Lys Tyr Thr Glu Leu Tyr Gln Gln
        340                 345                 350

Asn Lys Asn Glu Thr Ser Gln Lys Asn Thr Ser Arg Tyr Asp Asp Tyr
        355                 360                 365

Val Lys Asp Phe Phe Lys Lys Leu Glu Ala Asn Tyr Ser Ser Leu Glu
        370                 375                 380

Asn Tyr Ile Lys Gly Asp Pro Tyr Phe Ala Glu Tyr Ala Thr Lys Leu
385                 390                 395                 400

Ser Phe Ile Leu Asn Ser Ser Asp Ala Asn Asn Pro Ser Glu Lys Ile
                405                 410                 415

Gln Lys Asn Asn Asp Glu Val Cys Asn Cys Asn Glu Ser Gly Ile Ala
        420                 425                 430

Ser Val Glu Gln Glu Gln Ile Ser Asp Pro Ser Ser Asn Lys Thr Cys
        435                 440                 445

Ile Thr His Ser Ser Ile Lys Ala Asn Lys Lys Val Cys Lys His
        450                 455                 460

Val Lys Leu Gly Val Arg Glu Asn Asp Lys Asp Leu Arg Val Cys Val
465                 470                 475                 480

Ile Glu His Thr Ser Leu Ser Gly Val Glu Asn Cys Cys Cys Gln Asp
                485                 490                 495

Phe Leu Arg Ile Leu Gln Glu Asn Cys Ser Asp Asn Lys Ser Gly Ser
        500                 505                 510
```

```
Ser Ser Asn Gly Ser Cys Asn Asn Lys Asn Gln Glu Ala Cys Glu Lys
        515                 520                 525

Asn Leu Glu Lys Val Leu Ala Ser Leu Thr Asn Cys Tyr Lys Cys Asp
    530                 535                 540

Lys Cys Lys Ser Glu Gln Ser Lys Lys Asn Asn Lys Asn Trp Ile Trp
545                 550                 555                 560

Lys Lys Ser Ser Gly Lys Glu Gly Gly Leu Gln Lys Glu Tyr Ala Asn
                565                 570                 575

Thr Ile Gly Leu Pro Pro Arg Thr Gln Ser Leu Cys Leu Val Val Cys
            580                 585                 590

Leu Asp Glu Lys Gly Lys Lys Thr Gln Glu Leu Lys Asn Ile Arg Thr
        595                 600                 605

Asn Ser Glu Leu Leu Lys Glu Trp Ile Ile Ala Ala Phe His Glu Gly
    610                 615                 620

Lys Asn Leu Lys Pro Ser His Glu Lys Lys Asn Asp Asp Asn Gly Lys
625                 630                 635                 640

Lys Leu Cys Lys Ala Leu Glu Tyr Ser Phe Ala Asp Tyr Gly Asp Leu
                645                 650                 655

Ile Lys Gly Thr Ser Ile Trp Asp Asn Glu Tyr Thr Lys Asp Leu Glu
            660                 665                 670

Leu Asn Leu Gln Lys Ile Phe Gly Lys Leu Phe Arg Lys Tyr Ile Lys
        675                 680                 685

Lys Asn Asn Thr Ala Glu Gln Asp Thr Ser Tyr Ser Ser Leu Asp Glu
    690                 695                 700

Leu Arg Glu Ser Trp Trp Asn Thr Asn Lys Lys Tyr Ile Trp Leu Ala
705                 710                 715                 720

Met Lys His Gly Ala Gly Met Asn Ser Thr Thr Cys Cys Gly Asp Gly
                725                 730                 735

Ser Val Thr Gly Ser Gly Ser Cys Asp Asp Ile Pro Thr Ile Asp
            740                 745                 750

Leu Ile Pro Gln Tyr Leu Arg Phe Leu Gln Glu Trp Val Glu His Phe
        755                 760                 765

Cys Lys Gln Arg Gln Glu Lys Val Lys Pro Val Ile Glu Asn Cys Lys
    770                 775                 780

Ser Cys Lys Glu Ser Gly Gly Thr Cys Asn Gly Glu Cys Lys Thr Glu
785                 790                 795                 800

Cys Lys Asn Lys Cys Glu Val Tyr Lys Lys Phe Ile Glu Asp Cys Lys
                805                 810                 815

Gly Gly Asp Gly Thr Ala Gly Ser Ser Trp Val Lys Arg Trp Asp Gln
            820                 825                 830

Ile Tyr Lys Arg Tyr Ser Lys Tyr Ile Glu Asp Ala Lys Arg Asn Arg
        835                 840                 845

Lys Ala Gly Thr Lys Asn Cys Gly Pro Ser Ser Thr Thr Asn Ala Ala
    850                 855                 860

Glu Asn Lys Cys Val Gln Ser Asp Ile Asp Ser Phe Phe Lys His Leu
865                 870                 875                 880

Ile Asp Ile Gly Leu Thr Thr Pro Ser Ser Tyr Leu Ser Ile Val Leu
                885                 890                 895

Asp Asp Asn Ile Cys Gly Ala Asp Lys Ala Pro Trp Thr Thr Tyr Thr
            900                 905                 910

Thr Tyr Thr Thr Thr Glu Lys Cys Asn Lys Glu Thr Asp Lys Ser Lys
        915                 920                 925

Leu Gln Gln Cys Asn Thr Ala Val Val Val Asn Val Pro Ser Pro Leu
```

```
              930               935               940
Gly Asn Thr Pro His Gly Tyr Lys Tyr Ala Cys Gln Cys Lys Ile Pro
945                 950               955               960

Thr Asn Glu Glu Thr Cys Asp Asp Arg Lys Glu Tyr Met Asn Gln Trp
                965               970               975

Ser Cys Gly Ser Ala Arg Thr Met Lys Arg Gly Tyr Lys Asn Asp Asn
            980               985               990

Tyr Glu Leu Cys Lys Tyr Asn Gly Val Asp Val Lys Pro Thr Thr Val
        995               1000              1005

Arg Ser Asn Ser Ser Lys Leu Asp
    1010              1015

<210> SEQ ID NO 83
<211> LENGTH: 1088
<212> TYPE: PRT
<213> ORGANISM: artificial
<220> FEATURE:
<223> OTHER INFORMATION: VAR2CSA - EBV P18 antigen fragment F3

<400> SEQUENCE: 83

Met Asp Lys Ser Ser Ile Ala Asn Lys Ile Glu Ala Tyr Leu Gly Ala
1               5                   10                  15

Lys Ser Asp Asp Ser Lys Ile Asp Gln Ser Leu Lys Ala Asp Pro Ser
            20                  25                  30

Glu Val Gln Tyr Tyr Gly Ser Gly Asp Gly Tyr Tyr Leu Arg Lys
        35                  40                  45

Asn Ile Cys Lys Ile Thr Val Asn His Ser Asp Ser Gly Thr Asn Asp
50                  55                  60

Pro Cys Asp Arg Ile Pro Pro Tyr Gly Asp Asn Asp Gln Trp Lys
65                  70                  75                  80

Cys Ala Ile Ile Leu Ser Lys Val Ser Glu Lys Pro Glu Asn Val Phe
                85                  90                  95

Val Pro Pro Arg Arg Gln Arg Met Cys Ile Asn Asn Leu Glu Lys Leu
            100                 105                 110

Asn Val Asp Lys Ile Arg Asp Lys His Ala Phe Leu Ala Asp Val Leu
        115                 120                 125

Leu Thr Ala Arg Asn Glu Gly Glu Arg Ile Val Gln Asn His Pro Asp
    130                 135                 140

Thr Asn Ser Ser Asn Val Cys Asn Ala Leu Glu Arg Ser Phe Ala Asp
145                 150                 155                 160

Ile Ala Asp Ile Ile Arg Gly Thr Asp Leu Trp Lys Gly Thr Asn Ser
                165                 170                 175

Asn Leu Glu Gln Asn Leu Lys Gln Met Phe Ala Lys Ile Arg Glu Asn
            180                 185                 190

Asp Lys Val Leu Gln Asp Lys Tyr Pro Lys Asp Gln Asn Tyr Arg Lys
        195                 200                 205

Leu Arg Glu Asp Trp Trp Asn Ala Asn Arg Gln Lys Val Trp Glu Val
    210                 215                 220

Ile Thr Cys Gly Ala Arg Ser Asn Asp Leu Leu Ile Lys Arg Gly Trp
225                 230                 235                 240

Arg Thr Ser Gly Lys Ser Asn Gly Asp Asn Lys Leu Glu Leu Cys Arg
                245                 250                 255

Lys Cys Gly His Tyr Glu Glu Lys Val Pro Thr Lys Leu Asp Tyr Val
            260                 265                 270

Pro Gln Phe Leu Arg Trp Leu Thr Glu Trp Ile Glu Asp Phe Tyr Arg
```

```
                275                 280                 285
Glu Lys Gln Asn Leu Ile Asp Asp Met Glu Arg His Arg Glu Glu Cys
            290                 295                 300

Thr Ser Glu Asp His Lys Ser Lys Glu Gly Thr Ser Tyr Cys Ser Thr
305                 310                 315                 320

Cys Lys Asp Lys Cys Lys Lys Tyr Cys Glu Cys Val Lys Lys Trp Lys
                325                 330                 335

Ser Glu Trp Glu Asn Gln Lys Asn Lys Tyr Thr Glu Leu Tyr Gln Gln
            340                 345                 350

Asn Lys Asn Glu Thr Ser Gln Lys Asn Thr Ser Arg Tyr Asp Asp Tyr
            355                 360                 365

Val Lys Asp Phe Phe Lys Lys Leu Glu Ala Asn Tyr Ser Ser Leu Glu
            370                 375                 380

Asn Tyr Ile Lys Gly Asp Pro Tyr Phe Ala Glu Tyr Ala Thr Lys Leu
385                 390                 395                 400

Ser Phe Ile Leu Asn Ser Ser Asp Ala Asn Asn Pro Ser Glu Lys Ile
                405                 410                 415

Gln Lys Asn Asn Asp Glu Val Cys Asn Cys Asn Glu Ser Gly Ile Ala
            420                 425                 430

Ser Val Glu Gln Glu Gln Ile Ser Asp Pro Ser Ser Asn Lys Thr Cys
            435                 440                 445

Ile Thr His Ser Ser Ile Lys Ala Asn Lys Lys Val Cys Lys His
            450                 455                 460

Val Lys Leu Gly Val Arg Glu Asn Asp Lys Asp Leu Arg Val Cys Val
465                 470                 475                 480

Ile Glu His Thr Ser Leu Ser Gly Val Glu Asn Cys Cys Gln Asp
                485                 490                 495

Phe Leu Arg Ile Leu Gln Glu Asn Cys Ser Asp Asn Lys Ser Gly Ser
            500                 505                 510

Ser Ser Asn Gly Ser Cys Asn Asn Lys Asn Gln Glu Ala Cys Glu Lys
            515                 520                 525

Asn Leu Glu Lys Val Leu Ala Ser Leu Thr Asn Cys Tyr Lys Cys Asp
530                 535                 540

Lys Cys Lys Ser Glu Gln Ser Lys Lys Asn Asn Lys Asn Trp Ile Trp
545                 550                 555                 560

Lys Lys Ser Ser Gly Lys Glu Gly Gly Leu Gln Lys Glu Tyr Ala Asn
                565                 570                 575

Thr Ile Gly Leu Pro Pro Arg Thr Gln Ser Leu Cys Leu Val Val Cys
            580                 585                 590

Leu Asp Glu Lys Gly Lys Lys Thr Gln Glu Leu Lys Asn Ile Arg Thr
            595                 600                 605

Asn Ser Glu Leu Leu Lys Glu Trp Ile Ile Ala Ala Phe His Glu Gly
            610                 615                 620

Lys Asn Leu Lys Pro Ser His Glu Lys Lys Asn Asp Asp Asn Gly Lys
625                 630                 635                 640

Lys Leu Cys Lys Ala Leu Glu Tyr Ser Phe Ala Asp Tyr Gly Asp Leu
                645                 650                 655

Ile Lys Gly Thr Ser Ile Trp Asp Asn Glu Tyr Thr Lys Asp Leu Glu
            660                 665                 670

Leu Asn Leu Gln Lys Ile Phe Gly Lys Leu Phe Arg Lys Tyr Ile Lys
            675                 680                 685

Lys Asn Asn Thr Ala Glu Gln Asp Thr Ser Tyr Ser Ser Leu Asp Glu
            690                 695                 700
```

Leu Arg Glu Ser Trp Trp Asn Thr Asn Lys Lys Tyr Ile Trp Leu Ala
705                 710                 715                 720

Met Lys His Gly Ala Gly Met Asn Ser Thr Thr Cys Cys Gly Asp Gly
            725                 730                 735

Ser Val Thr Gly Ser Gly Ser Ser Cys Asp Asp Ile Pro Thr Ile Asp
            740                 745                 750

Leu Ile Pro Gln Tyr Leu Arg Phe Leu Gln Glu Trp Val Glu His Phe
            755                 760                 765

Cys Lys Gln Arg Gln Glu Lys Val Lys Pro Val Ile Glu Asn Cys Lys
            770                 775                 780

Ser Cys Lys Glu Ser Gly Gly Thr Cys Asn Gly Glu Cys Lys Thr Glu
785                 790                 795                 800

Cys Lys Asn Lys Cys Glu Val Tyr Lys Lys Phe Ile Glu Asp Cys Lys
            805                 810                 815

Gly Gly Asp Gly Thr Ala Gly Ser Ser Trp Val Lys Arg Trp Asp Gln
            820                 825                 830

Ile Tyr Lys Arg Tyr Ser Lys Tyr Ile Glu Asp Ala Lys Arg Asn Arg
            835                 840                 845

Lys Ala Gly Thr Lys Asn Cys Gly Pro Ser Ser Thr Thr Asn Ala Ala
850                 855                 860

Glu Asn Lys Cys Val Gln Ser Asp Ile Asp Ser Phe Phe Lys His Leu
865                 870                 875                 880

Ile Asp Ile Gly Leu Thr Thr Pro Ser Ser Tyr Leu Ser Ile Val Leu
            885                 890                 895

Asp Asp Asn Ile Cys Gly Ala Asp Lys Ala Pro Trp Thr Thr Tyr Thr
            900                 905                 910

Thr Tyr Thr Thr Thr Glu Lys Cys Asn Lys Glu Thr Asp Lys Ser Lys
            915                 920                 925

Leu Gln Gln Cys Asn Thr Ala Val Val Val Asn Val Pro Ser Pro Leu
930                 935                 940

Gly Asn Thr Pro His Gly Tyr Lys Tyr Ala Cys Gln Cys Lys Ile Pro
945                 950                 955                 960

Thr Asn Glu Glu Thr Cys Asp Asp Arg Lys Glu Tyr Met Asn Gln Trp
            965                 970                 975

Ser Cys Gly Ser Ala Arg Thr Met Lys Arg Gly Tyr Lys Asn Asp Asn
            980                 985                 990

Tyr Glu Leu Cys Lys Tyr Asn Gly Val Asp Val Lys Pro Thr Thr Val
            995                 1000                1005

Arg Ser Asn Ser Ser Lys Leu Asp Ala Ala Ser Ala Gly Thr Gly
    1010                1015                1020

Ala Leu Ala Ser Ser Ala Pro Ser Thr Ala Val Ala Gln Ser Ala
    1025                1030                1035

Thr Pro Ser Val Ser Ser Ser Ile Ser Ser Leu Arg Ala Ala Thr
    1040                1045                1050

Ser Gly Ala Thr Ala Ala Ala Ser Ala Ala Ala Val Asp Thr
    1055                1060                1065

Gly Ser Gly Gly Gly Gly Gln Pro His Asp Thr Ala Pro Arg Gly
    1070                1075                1080

Ala Arg Lys Lys Gln
    1085

<210> SEQ ID NO 84
<211> LENGTH: 5

```
<212> TYPE: PRT
<213> ORGANISM: artificial
<220> FEATURE:
<223> OTHER INFORMATION: glycine-serine linker
<220> FEATURE:
<221> NAME/KEY: VARIANT
<222> LOCATION: (1)..(5)
<223> OTHER INFORMATION: Can be repeated between 2 and 10, inclusive

<400> SEQUENCE: 84

Gly Gly Gly Gly Ser
1               5

<210> SEQ ID NO 85
<211> LENGTH: 5
<212> TYPE: PRT
<213> ORGANISM: artificial
<220> FEATURE:
<223> OTHER INFORMATION: Glycine-serine linker
<220> FEATURE:
<221> NAME/KEY: VARIANT
<222> LOCATION: (1)..(5)
<223> OTHER INFORMATION: Can be repeated between 2 and 6, inclusive

<400> SEQUENCE: 85

Gly Gly Gly Gly Ser
1               5

<210> SEQ ID NO 86
<211> LENGTH: 30
<212> TYPE: PRT
<213> ORGANISM: artificial
<220> FEATURE:
<223> OTHER INFORMATION: glycine-serine linker

<400> SEQUENCE: 86

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

IMMUNOGENIC CONSTRUCT COMPRISING AN EBV-CELL ANTIGEN AND A TARGETING MOIETY AND APPLICATIONS THEREOF

CROSS-REFERENCE TO RELATED APPLICATIONS

This application is a U.S. National Stage Application pursuant to 35 U.S.C. § 371 of International Patent Application PCT/EP2016/081309, filed on Dec. 15, 2016, and published as WO 2017/103020 on Jun. 22, 2017, which claims priority to European Patent Application 15307014.9, filed on Dec. 15, 2015, all of which are incorporated herein by reference in their entireties for all purposes.

The present invention generally relates to an immunogenic construct, useful for redirecting an Epstein-Barr Virus (EBV)-existing immune response towards an undesired target cell and/or microorganism, to methods for preparing said conjugate, to a pharmaceutical applications comprising said conjugate, and to medical applications thereof.

Immunotherapy is a type of treatment intended to modulate (i.e. induce, enhance or suppress) the body's immune responses to fight pathologies such as cancer, infectious diseases and neurodegenerative disorders. Many efforts have been conducted in the past 25 years to design immunogenic agents that can specifically recognize diseased cells and/or pathogens and trigger the elimination of said unwanted elements, either by eliciting a better immune response or by way of direct cytotoxicity. Numerous target-binding agents, such as proteins and antibodies, have been developed for such purpose, and can be conjugated with other active agents, such as microbial toxins or radioactive compounds, etc.

One of the advantages of said agents is their specificity towards their target, as it can not only minimize potential side effects but also maximize the elimination of the target. In this regard, antibodies, in particular monoclonal antibodies (mAbs) and antibody fragments such as VHHs, Fabs or scFvs, have gained a lot of interest in recent years as they have the ability to recognize a single molecular site or epitope on a target cell.

One major mode of action of many therapeutic monoclonal antibodies relies on antibody-dependent cell-mediated cytotoxicity (ADCC). Unfortunately, differential responses to therapeutic mAbs have been reported in the literature and are thought to correlate, at least in part, with specific polymorphisms in Fc receptor gene sequences. This greatly limits their use in a clinical context, as the affinity to Fc receptors is crucial to promote an effective cellular response.

By contrast, VHHs, Fabs and scFvs are not capable of mediating any Fc effector function such as ADCC, opsonic phagocytosis and/or complement activation, because they precisely lack a Fc region. The engineering of a Fc chain in those single chain antibodies would therefore be required in order to obtain a Fc effector function. However, such engineering is cumbersome and is likely to decrease the accessibility of potential cryptic epitopes present in small cellular cavities and clefts.

There is thus a need in the art to identify alternative immunogenic agents, which can overcome the limitations discussed above.

The inventors have herein unexpectedly discovered that an EBV B-cell antigen, conjugated to an antibody that targets a specific cell and/or microorganism, is capable of triggering in vivo an immune response eliminating said unwanted target, more particularly through opsonic phagocytosis. Surprisingly, such response can even be achieved if the antibody is lacking a Fc region. This is most probably rendered possible thanks to the indirect effector function exerted by said EBV antigen. Specific EBV B-cell antigens, and more particularly specific regions within the C-terminal of said antigens, that display the above capacity when conjugated to a target-binding antibody, have further been identified by the inventors.

Therefore, based on the findings disclosed herein, the present invention provides for the first time an immunogenic conjugate comprising a moiety binding to a target cell and/or microorganism and an Epstein-Barr Virus (EBV) B-cell antigen, methods for preparing said conjugate, a pharmaceutical composition comprising said conjugate, and related therapeutic applications.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, nomenclatures used herein, and techniques of molecular biology, biochemistry, chemistry, immunology and pharmacology are those well-known and commonly used in the art. Such techniques are fully explained in the literature (see notably: Molecular cloning: A laboratory manual 4th edition by Sambrook et al., Cold Spring Harbor Laboratory Press-Cold Spring Harbor, N.Y., USA, 2012; Remington: The Science and Practice of Pharmacy, 22nd ed., Mack Publishing Co., Easton, Pa., 2012; Kuby Immunology by Owen et al., 7th ed., Macmillan Education, 2013; Immunology Methods Manual vol. 1-4 by Lefkovits, Academic Press, 1996; Chemistry of Protein and Nucleic Acid Cross-linking and Conjugation by Wong and Jameson, 2nd ed., CRC Press, 2011; The Immunoassay Handbook by Wild et al., 4th ed., Elsevier, 2013; Bioconjugate techniques by Hermanson, 3rd ed., Elsevier, 2013).

The immunogenic conjugate proposed by the present invention can be used to redirect the immune response towards the clearance of a specific unwanted target cell or microorganism, in a subject in need thereof which exhibits an humoral immune response to EBV. Among humoral immune response to EBV, an existing humoral response to EBV can typically be observed upon EBV primo-infection of the subject, while a pre-existing humoral response to EBV can typically be observed for an EBV latent, chronic infection after a primo-infection of the subject with said virus.

So, in a first aspect, the present invention is directed to an immunogenic conjugate comprising:
 i) a moiety binding to a target cell and/or microorganism; and
 ii) an Epstein-Barr Virus (EBV) B-cell antigen.

The term "immunogenic" refers herein to the capacity of eliciting in vivo an immune response when administered to a subject. In the context of the present invention, said immune response, which is thus directly triggered by the conjugate of the invention upon its administration in a subject, is more particularly characterized by an opsonic phagocytosis of the target cell or microorganism, and/or a lysis of the target by antibody-dependent cell-mediated cytotoxicity (ADCC) and/or by antibody-dependent complement activation (and subsequent complement-dependent cytotoxicity (CDC)). Preferably, said immune response is characterized herein by an opsonic phagocytosis of the target cell and/or microorganism. Said immune response more particularly occurs thanks to the binding of the moiety i) to the unwanted target cell and/or microorganism present in a subject, and the immune recognition (i.e. binding) of the EBV B-cell antigen ii) by antibodies of a subject exhibiting a humoral immune response to EBV. As further explained below, said immune response is herein a humoral response (i.e. B-cell response) that does not directly involve MHC molecules, nor the engagement of any TCR (T-cell receptor).

The term "opsonic phagocytosis" relates herein to the process by which an unwanted element (herein, the target cell and/or microorganism) is ingested and eliminated by natural phagocytes, such as macrophages, in a subject. Such process is typically initiated by the binding and cross-linking of phagocytes Fc receptors to the subject antibodies that are complexed (i.e. bound) to the unwanted element, thereby forming an immune complex, which triggers in turn a signal-transduction pathway resulting in phagocytosis of said unwanted element.

The term "antibody-dependent cell-mediated cytotoxicity" or "ADCC" relates herein to the process by which an unwanted element (herein, the target cell and/or microorganism) is eliminated by non-specific cytotoxic cells that express Fc receptors (also known as effector cells), such as natural killers, neutrophils, macrophages and/or eosinophils, in a subject. Such process is typically initiated by the binding of said cells Fc receptors to the subject antibodies that are complexed (i.e. bound) to the unwanted element, which triggers in turn lysis of said unwanted element.

The term "antibody-dependent complement activation" or "classical complement pathway" relates herein to the process by which an unwanted element (herein, the target cell and/or microorganism) is eliminated by a membrane-attack complex (MAC) (also known as terminal complement complex or TCC), in a subject. Such process is typically initiated by the binding of the C1 complement present in plasma and the subject antibodies that are complexed (i.e. bound) to the unwanted element, which in turn activate said C1 complement and triggers a molecular cascade ultimately leading to the formation of a membrane-attack complex that forms large pores in the membrane of the unwanted element, thereby resulting in its lysis.

It is within the skill of the person in the art to test whether the conjugate according to the invention is immunogenic.

Indeed, respective binding of the EBV B-cell antigen ii) to antibodies of a subject and of the moiety i) to the target cell/microorganism can notably be assessed by designing an EBV B-cell antigen-binding assay and a moiety-binding assay using conventional techniques in the art, such as, without limitation, ELISA (enzyme-linked immunosorbent assay), Western-Blot, immunofluorescence assays, flow cytometry or surface plasmon resonance (The Immunoassay Handbook by Wild et al., 4th ed., Elsevier, 2013).

Besides, opsonic phagocytosis, ADCC and antibody-dependent complement activation can be assessed by immunological assays conventionally used in the art, as described notably in the literature by Chan et al. (2012), Jian et al. (2011) and Harboe et al. (2011). The Examples hereafter further provide detailed protocols for assessing target and antigen binding as well as opsonic phagocytosis, ADCC and antibody-dependent complement activation.

The term "conjugate" means herein that the moiety and the EBV B-cell antigen are bound or coupled to one another, either directly or indirectly. Such coupling can be performed by way of any biological or physiochemical means.

In the context of the present invention, it shall nevertheless be understood that such coupling is most preferably a stable coupling for in vivo applications, for example by way of covalent bonding. Indeed, depending upon the mode of administration and the pharmaceutical carriers used to deliver the conjugate to the subject, some bonds might not be well suited as others to withstand certain physiological environments such as the stomach. A stable coupling is further critical for opsonic phagocytosis, ADCC and/or complement activation to take place, as these may be compromised if the moiety targeting the cell and/or the microorganism and the EBV B-cell antigen are not in the vicinity from one another in vivo, due for example to cleavage of the bond between said moiety and/or said antigen.

Accordingly, it is a preferred embodiment to provide an immunogenic conjugate according to the invention, wherein said target-binding moiety is covalently coupled to said Epstein-Barr Virus B-cell antigen. More preferably, said target-binding moiety is covalently coupled to said Epstein-Barr Virus B-cell antigen, with the proviso that said moiety is non-cleavable, in particular in vivo, from said antigen. For example, the covalent bond linking the moiety and the antigen does not comprise a cleavage site, such as a protease cleavage site.

More preferably, said target-binding moiety is covalently and directly coupled to said Epstein-Barr Virus B-cell antigen. In other words, these components of the conjugate are not coupled via any linker. In such case, the immunogenic conjugate according to the invention is said to be consisting of i) a moiety binding to a target cell and/or microorganism, and ii) an Epstein-Barr Virus (EBV) B-cell antigen. For example, the conjugate may form a fusion protein.

Alternatively, said target-binding moiety can be covalently and indirectly coupled to said Epstein-Barr Virus B-cell antigen. In other words, these components of the conjugate are coupled via a linker. Indeed, depending upon the nature of the selected linker, the structure flexibility of the conjugate, its stability and/or solubility can be improved, and it was observed by the inventors that the presence of a linker coupling both components does not alter the immunogenic capacity of the conjugate.

By "linker" or "spacer", it is meant herein a chemical or biological agent, synthetic or natural, capable of coupling two molecules to one another. Chemical linkers are well-known in the art and are typically made of polymer chains of varying lengths, which can be homo- or hetero-bifunctional with identical or non-identical reactive groups and comprise at least one atom, preferably at least one carbon atom. By contrast, biological linkers are typically made of nucleic acid(s) and/or amino acid sequence(s) of varying lengths, and comprise at least one nucleic acid and/or amino acid. As stated above, said coupling is herein stable, i.e. the linker is covalently bound to components i) and ii) and is preferably (itself) non-cleavable, in particular in vivo. Even more preferably, said linker does not comprise a protease cleavage site. Such linkers and methods of coupling molecules, in particular proteins, have been extensively described in the literature, notably by Chen et al. (2013) and in Thermo Scientific: Crosslinking Technical Handbook (2015), and may thus be easily selected and designed by the skilled person in the art. Linkers can also be selected from carbohydrate polymers containing typically 2 to 10 of component sugars (e.g. simple sugars or monosaccharides).

Particularly preferred chemical linkers according to the invention include, without limitation amine-reactive linkers (NHS ester, imidoester), carboxyl-to-amine reactive linkers (carbodiimide), sulfhydryl-reactive linkers (maleimide, thiosulfonate), aldehyde reactive linkers (hydrazide, alikoxyamine), photo-reactive linkers (diazirinz, arylazide), hydroxyl-reactive linkers (isocyanate), and azide-reactive linkers (phosphine), to name a few.

Particularly preferred biological linkers according to the invention include, without limitation, polyproline (P)n (n being an integer typically comprised between 2 and 8) (SEQ ID NO:1), polyglycine (G)n (n being an integer typically comprised between 6 and 8) (SEQ ID NO:2), the glycine-serine linker (GGGGS)n (n being an integer typically comprised between 2 and 10 (SEQ ID NO:84), such as n=2 to 6 (SEQ ID NO:85) or n=2 to 5 (SEQ ID NO:3)), the α-helix-forming peptide linkers such as A(EAAAK)nA (n being an integer typically comprised between 2 and 5) (SEQ ID NO:4), and the proline-alanine linker PAPAP (SEQ ID NO:5) (Chen et al., 2013). A preferred biological irreversible linker according to the invention is the glycine-serine linker (GGGGS)n=2 to 10 (SEQ ID NO:84), such as (GGGGS)n=6 (SEQ ID NO: 86), (GGGGS)n=5 (SEQ ID NO:6), or advantageously (GGGGS)n=4 (SEQ ID NO:7).

By "moiety binding to a target cell and/or microorganism", abbreviated herein as "target-binding moiety" or "targeting moiety", it is meant a molecule that displays an affinity for a cell and/or microorganism of interest and is therefore capable of binding to it, notably onto its surface. The affinity of a molecule for a target of interest can be assessed by measuring the dissociation constant Kd and/or the association constant Ka as notably described in The Immunoassay Handbook by Wild et al., 4th ed., Elsevier (2013). In the context of the present invention, the binding is preferably specific to said cell and/or microorganism, i.e. the moiety is not capable to bind to another target (i.e. no affinity or little affinity for other targets).

The moiety of the immunogenic conjugate can be of proteic or non-proteic nature.

The terms "proteic", "peptidic" and polypeptidic" refer herein to a sequence of amino acids joined by peptide bonds (—NHCO—)-regardless of length or post-translational modification(s)—which can be naturally occurring or synthetic, and which can play a structural and/or functional role in a cell in vitro and/or in vivo.

In a preferred embodiment, said moiety is a ligand-binding protein.

Ligand-binding proteins are indeed of particular interest as they can exhibit a high affinity and selectivity towards their target. Besides, a myriad of ligand-binding proteins are already available in nature and can also be easily designed, tailored and/or produced by recombinant technologies.

The term "ligand-binding protein" encompasses herein any natural or synthetic protein capable of binding to a molecule (i.e. ligand). In other words, in the context of the present invention, said protein is binding to a ligand that is expressed on the surface of the target cell and/or microorganism.

Particularly preferred ligand-binding proteins according to the invention include, without limitation, antibodies, binding fragments thereof, antibody mimetics, cell-surface receptors, cell-surface ligands, and any combination thereof.

Among ligand-binding proteins, antibodies, derivatives and analogs thereof are particularly advantageous, as they exhibit, among others, a highly specific affinity towards their target (usually in the nanomolar range), a prolonged stability (up to several months), and can be easily and rapidly produced by conventional recombinant engineering techniques.

More precisely, the term "antibody" or "immunoglobulin" refers herein to a protein capable of specifically recognizing an antigen. To do so, the antibody's paratope interacts with the antigen's epitope. A whole antibody consists of four polypeptides-two full-length light chains and two full-length heavy chains-which are joined to one another with disulfide bonds to form a Y-shaped protein. Each heavy chain contains one variable (VH) domain followed by a constant domain (CH1), a hinge region, and two or three more constant domains (CH2, CH3 and optionally CH4), while each light chain contains one variable (VL) and one constant (CL) domain. An antibody specifically recognizes its corresponding antigen via the so-called variable region located at each tip of the "Y" and which is specific to each antibody (it represents the antigen binding site), while the ability of the antibody to trigger an immune response is mediated by the Fc region located at the base of the "Y". In mammals, antibodies are divided into five major isotypes known as IgA, IgD, IgE, IgM and IgG, IgG being further divided into four subtypes (IgG1, IgG2, IgG3 and IgG4 in humans). The term "antibody" is intended herein to encompass mono- and polyclonal antibodies (i.e. produced by a single or different clones of B cells), mono-, bi- and multispecific antibodies (i.e. that binds to one or more antigens), as well as mono-, bi- and multivalent antibodies (i.e. that has one or two antigen binding sites). For the purposes of the present invention, the antibody binding to the target cell and/or microorganism is preferably monoclonal and monospecific. Besides, said antibody is preferably humanized according to methods conventionally used in the art (Immunobiology by Janeway et al., 5th edition, Garland publishing, 2001; Therapeutic Monoclonal Antibodies: From Bench to Clinic by An et al., Wiley editions, 2009).

Antibody fragments are herein preferred over whole antibodies, as they exhibit a greater solubility, tissue penetration (in particular solid tissue), and stability towards heat and/or enzymes thanks to their smaller size, as well as a lower production cost.

The term "antibody fragment" or "antibody-binding fragment" refers more specifically to a fragment which retains at least the antigen-binding function of an antibody as defined above. Examples of antibody fragments well-known in the art, include, without limitation Fab antibodies, Fab' antibodies, F(ab')2 antibodies, Fv antibodies, single chain antibodies (scFv), heavy chain antibodies (HCAb) in particular single domain antibodies (sdAb) and any combination thereof.

Fab (fragment antigen binding) antibodies are composed of one variable region of each of the heavy and the light chain, the constant domain of the light chain, and the first constant domain (CH1) of the heavy chain, with an antigen binding site (paratope). Fab' differ from Fab in that they further comprise at least one cysteine residue at the C-terminus of the CH1 domain of the heavy chain, while F(ab')2 consist of two molecules of Fab' with a disulfide bond between the cysteine residues of the hinge region. Fv (variable fragment) antibodies are composed of one variable region of each of the heavy and the light chain, while single chain Fv (scFv) antibodies consist of an Fv in which the respective variable regions of the heavy and the light chain are covalently connected by a peptide linker. Finally, single domain antibodies, which are derived from heavy chain antibodies (HCAb) originally identified in camels and sharks and are also known as domain antibodies, single-domain antibodies or nanobodies (and abbreviated as VHH when produced from camels, and IgNAR or VNAR when produced from cartilaginous fishes such as sharks), solely correspond to the variable region of the heavy chain of antibodies, and are up to this day the smallest antibody fragment containing the original specificity and binding affinity of a parent antibody.

It is within the skill of the person in the art to produce such fragments from a parent antibody, for example by treating a whole antibody with proteases (e.g. by digestion of a whole antibody with papain or pepsin can produce Fab or F(ab')2, respectively), or by way of genetic recombinant technology (e.g. by molecular design and purification of scFv or VHH).

It must further be noted that the above-mentioned antibody fragments can be devoid of Fc region. Interestingly, as illustrated in the Examples hereafter, their lack in Fc region does not alter the capacity of the conjugate to trigger in vivo an immune response eliminating the target, in particular through opsonic phagocytosis, ADCC and/or antibody-dependent complement activation.

Particularly preferred antibody fragments according to the invention are single-domain antibodies.

Indeed, single domain antibodies exhibit superior physico-chemical properties as compared to other antibodies, among which a faster tissue penetration and an ability to recognize cryptic epitopes due to their smaller size (15 kDa), the possibility to be coded by a single gene (which facilitates their engineering and abolishes the risk of partial unfolding as observed with scFv), their capacity to be stored at room temperature, high solubility, and low immunogenic potential.

Besides, as demonstrated in the Examples hereafter, single domain antibodies coupled to an EBV B-cell antigen retain their full functionality and specificity towards their target, while allowing the immunogenic conjugate to be highly recognized by IgG of subjects that are or have been affected by EBV, thereby triggering in vivo an immune response eliminating the target, in particular through opsonic phagocytosis, ADCC and/or antibody-dependent complement activation.

Alternative proteic moieties according to the invention are represented by antibody mimetics. The terms "antibody mimetics", "antibody mimetic scaffolds", "antibody-like scaffolds", "non-antibody scaffolds" and "non-immunoglobulin scaffolds" refer to artificial peptides or proteins that are not structurally related to antibodies and that generally have a lower molecular weight than whole antibodies. Therefore, due to their small size, antibody mimetics exhibit advantageous properties similar to the ones described above for antibody fragments. Examples of suitable antibody mimetics according to the invention include, without limitation, ABDs, adhirons, adnectins/monobodies, affibodies, affilins, affitins/nanofitins, affimers, alphabodies, anticalins, armadillo repeat proteins, atrimers/tetranectins, avimers/maxibodies, centyrins, DARPins, fynomers, Kunitz domains, obodies/OB-folds, pronectins, repebodies, transbodies and trimers X (Skrlec et al., 2015).

Particularly preferred antibodies according to the invention are:
  anti-DARC antibodies, which bind to the Duffy antigen/chemokine receptor of erythrocytes, and more preferably anti-DARC single domain antibodies such as the one described by Smoralek et al. (2010). Most preferably, said anti-DARC antibody according to the invention comprises or consists of the sequence SEQ ID NO:8 or SEQ ID NO:9, most preferably SEQ ID NO:9;
  anti-VAR2CSA antibodies, which bind to the malaria-associated antigen VAR2CSA, and more preferably anti-VAR2CSA single domain antibodies such as the ones described by Nunes et al. (2014). Most preferably, said anti-VAR2CSA antibody according to the invention comprises or consists of the sequence SEQ ID NO:10 or SEQ ID NO:11, most preferably SEQ ID NO:11;
  anti-VSG antibodies, which bind to the Variable Surface Glycoprotein, a major surface antigen typically expressed at the surface of infectious microorganisms such as *Trypanosoma brucei*, and more preferably anti-VSG single domain antibodies such as the one described by Conrath et al. (2005). Most preferably, said anti-VSG antibody comprises or consists of the sequence SEQ ID NO:12 or SEQ ID NO:13, most preferably SEQ ID NO:13; and
  anti-CD20 antibodies, which bind to the Cluster of Differentiation 20 which is typically overexpressed by cancer cells, more preferably anti-CD20 ScFv such as the one described by Otz et al. (2009), Liu et al. (1987) or Olafsen et al.(2009). Most preferably, said anti-CD20 antibody comprises or consists of the sequence SEQ ID NO:80.

In the context of the present invention, an immunogenic conjugate comprising anti-VAR2CSA antibody is indeed intended to treat malaria, while a conjugate comprising an anti-VSG antibody is intended to treat trypanosomiasis (also known as the sleeping sickness) and a conjugate comprising an anti-CD20 antibody is intended to treat cancer.

Cell-surface receptors can alternatively be used as ligand-binding proteins according to the invention. For example, should the target cell be a malaria infected erythrocyte (i.e. an erythrocyte infected by *Plasmodium falciparum*) and/or the target microorganism be *Plasmodium falciparum*, particularly preferred cell-surface receptors to be used as a targeting-moiety include, without limitation, the following endothelial cell receptors: protein C receptor (EPCR) (also known as activated protein C receptor or APC receptor, preferably comprising or consisting of the sequence SEQ ID NO:14), Cluster of Differentiation 36 (CD36), Cluster of Differentiation 31 (CD31 or PECAM-1), intercellular adhesion molecule-1 (ICAM-1), and E-selectin. Indeed, as well-known in the art, cytoadhesion of *Plasmodium falciparum*-infected erythrocytes to endothelial cell receptors is associated with severe malaria (Aird et al., 2014). Hence, an immunogenic conjugate according to the invention comprising any of the above-mentioned endothelial cell receptors would bind to malaria infected erythrocytes, and trigger their elimination.

Cell-surface ligands can alternatively be used as ligand-binding proteins according to the invention. For example, should the target cell be a cancer cell, particularly preferred cell-surface ligands to be used as a targeting-moiety include, without limitation, *Plasmodium falciparum*-derived VAR2CSA fragments which can bind to the Chondroitin Sulfate A (CSA) cell surface receptor. Indeed, as well-known in the art, CSA is typically over-expressed by cancer cells. Hence, an immunogenic conjugate according to the invention comprising any VAR2CSA fragment would bind to cancer cells, and trigger their elimination. Particularly preferred VAR2CSA fragments encompass the CSA binding region, such as the one described by Srivastava et al.(2011) or Clausen et al.(2012), or, more preferably, comprise or consist of the sequence SEQ ID NO:82.

In another preferred embodiment, the target-binding moiety is non-proteic. Indeed, the moiety according to the invention can be a non-proteic ligand that is capable of binding to the surface of a cell and/or to the surface of a microorganism, for example by binding to cell surface receptors.

Particularly preferred non-proteic moieties according to the invention include, without limitation, vitamins such as folates (Zwicke et al., 2012), carbohydrates such as galactose derivatives (Wu et al., 2002), glycosaminoglycans such as chondroitin sulfate, heparin or heparan sulphate (Vogt et al., 2003), small nucleic acids such as DNA or RNA aptamers (Estevez et al.,2010; Birch et al., 2015), and small chemical compounds.

In particular, folates are capable of binding to folate receptors that are highly expressed on the surface of many cancer cells, while some galactose derivatives can bind to the asialoglycoprotein receptor (ASGPR) expressed on hepatocytes and hepatoma cells, while chondroitin sulfate and heparan sulfate can bind to the surface of erythrocytes infected by *Plasmodium falciparum*.

With regard to DNA or RNA aptamers and small chemical compounds, those can be easily designed by the skilled person in the art so as to specifically bind to a target cell and/or microorganism, using conventional methods in the art such as systematic evolution of ligands by exponential enrichment (SELEX) (Stoltenburg et al., 2007).

It should nevertheless be understood that the above examples of proteic and non-proteic targeting-moieties are for illustrative purpose only and are thus not limitative. Hence, any other suitable targeting moiety can be used in the context of the invention, as long as it exhibits the capacity to bind to the cell and/or microorganism of interest.

As stated above, the antigen used in the immunogenic conjugate of the invention is a B-cell antigen isolated from the Epstein-Barr Virus.

The term "antigen" designates herein any molecule (e.g. nucleic acid, peptide, protein, polysaccharide, etc) that can prompt under certain circumstances the generation of antibodies upon administration in a subject, thereby generating an immune response. At the molecular level, an antigen is characterized by at least one, preferably at least two, epitope(s) which corresponds to the region recognized by the immune system, and more specifically by circulating antibodies, B cells or T cells (B and T cell receptors being composed, but not exclusively of membrane-bound antibodies) The term "B-cell antigen" refers to an antigen as defined above which is capable of eliciting a B-cell response, or in other words the production, by B-cells of the immune system, of antibodies specifically directed against said antigen (also known as humoral response). Such B-cell response can thus be detected by measuring antibody titers, such as IgG titers, from the plasma of subjects to which the antigen has been administered. The epitopes of B-cell antigens are characterized as B-epitopes, which are recognized by the corresponding paratopes of antibodies.

For the purposes of the present invention, the B-cell antigen can elicit an existing or pre-existing B-cell (i.e. humoral) immune response in the subject to which the conjugate of the invention is administered. That is, said antigen is one to which B cells of the subject are already sensitized to. More specifically, said B-cell antigen originates from the Epstein-Barr Virus and is as such designated as an "EBV B-cell antigen" or "Epstein-Barr Virus B-cell antigen".

The "Epstein Barr Virus" or "EBV", also known as "human herpes virus-4" or "HHV4", is a common virus belonging to the Herpesviridae family, which infects 95% of the worldwide human population and is implicated in several diseases that include infectious mononucleosis, Burkitt's lymphoma and Hodgkin's lymphoma, to name a few. Following primary infection, EBV establishes a life-long persistent infection characterized by frequent mild viral reactivation to allow shedding and transmission. Primary EBV infection as well as EBV reactivation are marked by high antibody levels and are predominantly of cytophylic type. EBV can be divided into two major subtypes that are EBV type 1 and EBV type 2. During its replication in the infected host, said virus expresses a myriad of antigens against which antibodies can develop (i.e. B-cell antigens), and which are classified among LYDMA (Lymphocyte-defined membrane antigen), EBNA (Epstein-Barr nuclear antigen), EMA (Early membrane antigen), EA (Early antigen), LMA (Late membrane antigen), and VCA (Virus capsid antigen) antigens. These classes of antigens comprise themselves a plurality of antigens: for example, the EBNA class comprises the EBNA-1, EBNA-2, EBNA-3A, EBNA-3B, EBNA-3C, and EBNA-leader protein (EBNA-LP); while the VCA class comprises the antigens P18 (i.e. BFRF3), P23 (i.e. BLRF2), GP125 (i.e. BALF4), P143 (i.e. BNRF1), P150 (i.e. BcLF1) and P40 (i.e. BdRF1).

The Inventors have herein discovered that the Epstein-Barr Virus P18 and P23 antigens, and more particularly specific regions in the vicinity of and/or within the C-terminal of said antigens can, when conjugated to the target-binding moiety as described above, trigger in vivo a humoral (i.e. B-cell) immune response leading to the formation of immune complexes and subsequent elimination of said target, more particularly through opsonic phagocytosis, ADCC and/or antibody-dependent complement activation.

Thus, in a preferred embodiment, said Epstein-Barr Virus B-cell antigen is selected from the group consisting of the P18 antigens of sequence SEQ ID NO:15, the P23 antigens of sequence SEQ ID NO:16, functional variants and functional fragments thereof, and any combination thereof; said sequences being more particularly defined as follows:

SEQ ID NO: 15

MX$_1$RRLPKPTLQGRLEADFPDSPLLPKFQELNQNNLPNDVFREAQRSYLV

FLTSQFCYEEYVQRTFGVPRRQRAIDKRQRASVAGAGAHAHLGGSSATP

VQQAQAAASAGTGALASSAPSTAVAQSX$_2$TPSVSSSISX$_3$LRAATSGATA

AX$_4$X$_5$AAAAVDTGSGGGGQPX$_6$DTAPRGARKKQ, wherein:
  X$_1$ is A or S,
  X$_2$ is A or V,
  X$_3$ is S or N,
  X$_4$ is A or nothing,
  X$_5$ is S or nothing, and
  X$_6$ is Q or H;
and

SEQ ID NO: 16

MSAPRKVRLPSVKAVDMSMEDMAARLARLESENKALKQX$_1$VLRGGACASS

TSVPSX$_2$X$_3$VPPPEPLTARQREVMITQATGRLASQAMKKIEX$_4$KVRKSVD

GVTTRNEX$_5$EX$_6$ILQNLTLRIQVSMLGAKGQPSPGEGX$_7$RX$_8$X$_9$X$_{10}$X$_{11}$X$_{12}$

DPNX$_{13}$TRRARX$_{14}$X$_{15}$SRGX$_{16}$EX$_{17}$KKVQISD, wherein:
  X$_1$ is Q or R,
  X$_2$ is A or V,
  X$_3$ is P or T,
  X$_4$ is D or E,
  X$_5$ is M or L,
  X$_6$ is N or K,
  X$_7$ is T or P,
  X$_8$ is P, L or S,
  X$_9$ is R, N or nothing,
  X$_{10}$ is E, D or nothing,
  X$_{11}$ is S, P or nothing, $X_{12}$ is N or S,
$X_{13}$ is A, T, S or N,
$X_{14}$ is S or nothing,
$X_{15}$ is R or nothing,
$X_{16}$ is R or C, and
$X_{17}$ is A or S.

Particularly preferred P18 antigens according to the invention include, without limitation, the antigens of sequence SEQ ID NO:17 to SEQ ID NO:22; while particularly preferred P23 antigens according to the invention include, without limitation, the antigens of sequence SEQ ID NO:23 to SEQ ID NO:38.

More preferably, the P18 antigen according to the invention is of sequence SEQ ID NO: 17 and/or the P23 antigen according to the invention is of sequence SEQ ID NO:23.

As stated above, the invention further encompasses functional variants and functional fragments of the P18 and P23 antigens described herein.

In this regard, cysteine residue(s) contained within the P18 and P23 antigens may form disulfide bonds with thiol groups contained in the target-binding moiety, which, as illustrated in the Examples hereafter, can alter the solubility and stability of the conjugate. It may thus be desired to design the functional variants and/or functional fragments so that they do not contain any thiol group, i.e. herein any cysteine residue.

Accordingly, it is a preferred embodiment of the invention to provide an immunogenic conjugate as defined above, with the proviso that, when said moiety comprises at least one thiol group, the functional variants and functional fragments of the P18 and/or P23 antigens do not comprise (i.e. are devoid of) any cysteine residue. The thiol group may itself be contained in a cysteine residue, should the moiety be of proteic nature.

A "functional variant" of such EBV B-cell antigen structurally exhibits a different amino acid sequence than the one of said antigen while retaining the capacity of eliciting a B-cell response, and in particular opsonic phagocytosis and/or ADCC and/or complement activation. Variants can be naturally or non-naturally occurring. Non-naturally occurring variants are typically generated by mutagenesis, and can be referred as such as mutated variants. The latter can result from conservative or non-conservative amino acid mutations such as substitutions, deletions and/or additions between the amino acid sequence of reference and the variant. Functional variants encompass herein amino acid sequences which are at least 85% identical after alignment to the amino acid sequence of the native antigen. These variants can also have 90%, 95%, 96%, 97%, 98%, 99%, and 99,999% sequence identity to said amino acid sequence. Identity between amino acid sequences can be typically determined by a global homology alignment.

Functional variants according to the invention that are devoid of any cysteine residue are preferably selected from the group consisting of the P18 antigen functional variants of sequence SEQ ID NO:39 and the P23 antigen functional variants of sequence SEQ ID NO:40, said sequences being more particularly defined as follows:

SEQ ID NO: 39
MX$_1$RRLPKPTLQGRLEADFPDSPLLPKFQELNQNNLPNDVFREAQRSYLV

FLTSQFSYEEYVQRTFGVPRRQRAIDKRQRASVAGAGAHAHLGGSSATP

-continued

VQQAQAAASAGTGALASSAPSTAVAQSX$_2$TPSVSSSISX$_3$LRAATSGATA

AX$_4$X$_5$AAAAVDTGSGGGGQPX$_6$DTAPRGARKKQ, wherein:
  $X_1$ is A or S,
  $X_2$ is A or V,
  $X_3$ is S or N,
  $X_4$ is A or nothing,
  $X_5$ is S or nothing, and
  $X_6$ is Q or H;
and

SEQ ID NO: 40
MSAPRKVRLPSVKAVDMSMEDMAARLARLESENKALKQX$_1$VLRGGASASS

TSVPSX$_2$X$_3$VPPPEPLTARQREVMITQATGRLASQAMKKIEX$_4$KVRKSVD

GVTTRNEX$_5$EX$_6$ILQNLTLRIQVSMLGAKGQPSPGEGX$_7$RX$_8$X$_9$X$_{10}$X$_{11}$X$_{12}$

DPNX$_{13}$TRRARX$_{14}$X$_{15}$SRGX$_{16}$EX$_{17}$KKVQISD, wherein:
  $X_1$ is Q or R,
  $X_2$ is A or V,
  $X_3$ is P or T,
  $X_4$ is D or E,
  $X_5$ is M or L,
  $X_6$ is N or K,
  $X_7$ is T or P,
  $X_8$ is P, L or S,
  $X_9$ is R, N or nothing,
  $X_{10}$ is E, D or nothing,
  $X_{11}$ is S, P or nothing,
  $X_{12}$ is N or S,
  $X_{13}$ is A, T, S or N,
  $X_{14}$ is S or nothing,
  $X_{15}$ is R or nothing,
  $X_{16}$ is R or C, and
  $X_{17}$ is A or S.

Particularly preferred functional variants according to the invention include, without limitation, the P18 antigen functional variant of sequence SEQ ID NO:41 and/or the P23 antigen functional variant of sequence SEQ ID NO:42.

A "functional fragment" of such B-cell antigens contains only parts of the amino acid sequence of said antigen, parts which comprise all the essential regions or epitopes for exhibiting the same biological function as the one of said antigen, i.e. the elicitation of an antibody-mediated immune response, and in particular opsonic phagocytosis and/or ADCC and/or complement activation which can be assessed as described above. These parts can be of various lengths provided that said response is retained.

For example, the functional fragments according to the invention can comprise at least 5 amino acid residues of said antigen, or at least 10 amino acid residues of said antigen, or at least 15 amino acid residues of said antigen, and preferably at least 20 amino acid residues of said antigen.

Preferably, the functional fragments according to the invention comprise between about 5 amino acid residues and about 150 amino acid residues, more preferably between about 10 amino acid residues and about 150 amino acid residues, even more preferably between about 15 amino acid residues and about 100 amino acid residues, and most preferably between about 20 amino acid residues and about 100 amino acid residues.

Yet, preferably, the functional fragments according to the invention comprise between about 5 successive amino acid residues and about 150 successive amino acid residues, more preferably between about 10 successive amino acid residues and about 150 successive amino acid residues, even more preferably between about 15 successive amino acid residues and about 100 successive amino acid residues, and most preferably between about 20 successive amino acid residues and about 100 successive amino acid residues.

Still preferably, functional fragments according to the invention are P18 antigen functional fragments comprising or consisting of at least the sequence selected from the group consisting of SEQ ID NO:43 to SEQ ID NO:49 and SEQ ID NO:75, and/or P23 antigen functional fragments comprising or consisting of at least the sequence selected from the group consisting of SEQ ID NO:50 and SEQ ID NO:51, said sequences being more particularly defined as follows:

SEQ ID NO: 43
VDTGSGGGGQPX$_6$DTAPRGARKKQ, wherein X$_6$ is Q or H;

SEQ ID NO: 44
AGAGAHAHLGGSSATPVQQAQAAASAGTGALASSAPSTAVAQSX$_2$TPSVS SSISX$_3$LRAATSGATAAX$_4$X$_5$AAAAVDTGSGGGGQPX$_6$DTAPRGARKKQ, wherein:
X$_2$ is A or V,
X$_3$ is S or N,
X$_4$ is A or nothing,
X$_5$ is S or nothing, and
X$_6$ is Q or H;

SEQ ID NO: 75
AASAGTGALASSAPSTAVAQSX$_2$TPSVSSSISX$_3$LRAATSGATAAX$_4$X$_5$AA AAVDTGSGGGGQPX$_6$DTAPRGARKKQ, wherein:
X$_2$ is A or V,
X$_3$ is S or N,
X$_4$ is A or nothing,
X$_5$ is S or nothing, and
X$_6$ is Q or H;

SEQ ID NO: 45
RQRAIDKRQRASVAGAGAHAHLGGSSATPVQQAQAAASAGTGALASSAP STAVAQSX$_2$TPSVSSSISX$_3$LRAATSGATAAX$_4$X$_5$AAAA, wherein:
X$_2$ is A or V,
X$_3$ is S or N,
X$_4$ is A or nothing, and
X$_5$ is S or nothing;

SEQ ID NO: 46
AGAGAHAHLGGSSATPVQQAQAAASAGTGALASSAPSTAVAQSX$_2$TPSVS SSISX$_3$LRAATSGATAAX$_4$X$_5$AAAA, wherein:
X$_2$ is A or V,
X$_3$ is S or N,
X$_4$ is A or nothing, and
X$_5$ is S or nothing;

SEQ ID NO: 47
SX$_2$TPSVSSSISX$_3$LRAATSGA, wherein:
X$_2$ is A or V, and
X$_3$ is S or N;

SEQ ID NO: 48
SVSSSISX$_3$LR, wherein:
X$_3$ is S or N;

SEQ ID NO: 49
RQRAIDKRQRASVAGAGAHAHLGGSSATPVQQAQAAASAGTGALASSAPS TAVAQSX$_2$TPSVSSSISX$_3$LRAATSGATAAX$_4$X$_5$AAAAVDTGSGGGGQPX$_6$ DTAPRGARKKQ, wherein:
X$_2$ is A or V,
X$_3$ is S or N,
X$_4$ is A or nothing,
X$_5$ is S or nothing, and
X$_6$ is Q or H;

SEQ ID NO: 50
EX$_5$EX$_6$ILQNLTLRIQVSMLGAKGQPSPGEGX$_7$RX$_8$X$_9$X$_{10}$X$_{11}$X$_{12}$DPNX$_{13}$T RRARX$_{14}$X$_{15}$SRGX$_{16}$EX$_{17}$KKVQISD, wherein:
X$_5$ is M or L,
X$_6$ is N or K,
X$_7$ is T or P,
X$_8$ is P, L or S,
X$_9$ is R, N or nothing,
X$_{10}$ is E, D or nothing,
X$_{11}$ is S, P or nothing,
X$_{12}$ is N or S,
X$_{13}$ is A, T, S or N,
X$_{14}$ is S or nothing,
X$_{15}$ is R or nothing,
X$_{16}$ is R or C, and
X$_{17}$ is A or S;
and SEQ ID NO: 51
ATGRLASQAMKKIEX$_4$KVRKSVDGVTTRNEX$_5$EX$_6$ILQNLTLRIQVSMLG AKGQPSPGEGX$_7$RX$_8$X$_9$X$_{10}$X$_{11}$X$_{12}$DPNX$_{13}$TRRARX$_{14}$X$_{15}$SRGX$_{16}$EX$_{17}$KK VQISD, wherein:
X$_4$ is D or E,
X$_5$ is M or L,
X$_6$ is N or K,
X$_7$ is T or P,
X$_8$ is P, L or S,
X$_9$ is R, N or nothing,
X$_{10}$ is E, D or nothing,
X$_{11}$ is S, P or nothing,
X$_{12}$ is N or S,
X$_{13}$ is A, T, S or N, $X_{14}$ is S or nothing,
$X_{15}$ is R or nothing,
$X_{16}$ is R or C, and
$X_{17}$ is A or S.

According to a preferred embodiment, functional fragments according to the invention are P18 antigen functional fragments comprising or consisting of at least the sequence selected from the group consisting of SEQ ID NO:43 to SEQ ID NO:49, and/or P23 antigen functional fragments comprising or consisting of at least the sequence selected from the group consisting of SEQ ID NO:50 and SEQ ID NO:51.

According to another preferred embodiment, functional fragments according to the invention are P18 antigen functional fragments comprising or consisting of at least the sequence selected from the group consisting of SEQ ID NO:43, SEQ ID NO:75 and SEQ ID NO:45 to SEQ ID NO:49, and/or P23 antigen functional fragments comprising or consisting of at least the sequence selected from the group consisting of SEQ ID NO:50 and SEQ ID NO:51.

According to a more preferred embodiment, functional fragments according to the invention are P18 antigen functional fragments comprising or consisting of at least the sequence selected from the group consisting of SEQ ID NO:43, SEQ ID NO:49 and SEQ ID NO:75, and/or P23 antigen functional fragments comprising or consisting of at least the sequence selected from the group consisting of SEQ ID NO:50 and SEQ ID NO:51.

In particular, in order of preference among the P18 antigen functional fragments, one should select the fragment comprising or consisting of at least the sequence SEQ ID NO:75, followed by SEQ ID NO:49, and at last SEQ ID NO:43. In other words, a most preferred P18 antigen functional fragment according to the invention is the one comprising or consisting of at least the sequence SEQ ID N:75. Indeed, as illustrated in the Examples hereafter, this fragment exhibited the best immune response among the P18 functional antigen fragments tested.

Examples of particularly preferred functional fragments according to the invention include, without limitation, P18 antigen functional fragments comprising or consisting of the sequence selected from the group consisting of SEQ ID NO: 52 to SEQ ID NO:58 and SEQ ID NO: 76, and/or P23 antigen functional fragments comprising or consisting of the sequence selected from the group consisting of SEQ ID NO:59 and SEQ ID NO:60. More preferably, said functional fragments include, without limitation, P18 antigen functional fragments comprising or consisting of the sequence selected from the group consisting of SEQ ID NO: 52 to SEQ ID NO:58, and/or P23 antigen functional fragments comprising or consisting of the sequence selected from the group consisting of SEQ ID NO:59 and SEQ ID NO:60. Yet, even more preferably, said functional fragments include, without limitation, P18 antigen functional fragments comprising or consisting of the sequence selected from the group consisting of SEQ ID NO: 52, SEQ ID NO:76 and SEQ ID NO: 54 to SEQ ID NO:58, and/or P23 antigen functional fragments comprising or consisting of the sequence selected from the group consisting of SEQ ID NO:59 and SEQ ID NO:60. Said fragments are the most preferred EBV B-cell antigens according to the invention as they contain the minimal epitopes necessary for IgG recognition in a subject, and thus for creating in vivo immune complexes and triggering an immune response eliminating the target of interest.

According to a more preferred embodiment, examples of functional fragments according to the invention are P18 antigen functional fragments comprising or consisting of the sequence selected from the group consisting of SEQ ID NO:52, SEQ ID NO:58 and SEQ ID NO:76, and/or P23 antigen functional fragments comprising or consisting of the sequence selected from the group consisting of SEQ ID NO:59 and SEQ ID NO:60.

In particular, in order of preference among the P18 antigen functional fragments, one should select the fragment comprising or consisting of the sequence SEQ ID NO:76, followed by SEQ ID NO:58, and at last SEQ ID NO:52. In other words, a most preferred P18 antigen functional fragment according to the invention is the one comprising or consisting of the sequence SEQ ID N:76. Indeed, as illustrated in the Examples hereafter, this fragment exhibited the best immune response among the P18 functional antigen fragments tested.

As stated above, the above fragments can preferably be devoid of any cysteine residue.

Importantly, the cell and/or microorganism targeted by the binding moiety of the conjugate can be of any origin, as long as one wishes to eliminate said cell and/or microorganism that is present in a subject in need thereof.

Thus, in a preferred embodiment, the target cell is a diseased cell, preferably a cancer cell or a cell infected by a pathogen such as a virus, a bacterium, a fungus and/or a parasite, and/or the target microorganism is a pathogenic microorganism, preferably a virus, a bacterium, a fungus and/or a parasite.

As demonstrated in the Examples hereafter, the Inventors have more particularly designed two distinct immunogenic conjugates intended to target *Plasmodium falciparum*, so as to treat malaria, as well as two distinct immunogenic conjugates intended to target CD20- or CSA-expressing cells, respectively, so as to treat cancer.

Accordingly, in a particularly preferred embodiment, said diseased cell is a malaria infected erythrocyte, and/or said pathogenic microorganism is *Plasmodium falciparum*.

If the diseased cell targeted is a malaria infected erythrocyte, said moiety can preferably be binding to a malaria-associated antigen expressed on the surface of said cell, preferably to *Plasmodium falciparum* erythrocyte membrane protein 1 (PfEMP1) variants such as the VAR2CSA or VAR19 antigen. An example of a moiety binding to VAR19 is the protein C receptor (EPCR, which can comprise or consist of SEQ ID NO:14).

In another particularly preferred embodiment, said diseased cell is a cancer cell.

If the diseased cell is a cancer cell, said moiety can preferably be binding to the CSA expressed on the surface of said cell or, in case of a cancer from B cell origins (B lymphoma), to the Cluster of differentiation 20 (CD20) expressed on the surface of said cell.

The conjugate according to the invention can be prepared by various methods, that may vary depending upon the nature of the target-binding moiety, and/or if a chemical or peptide linker is used to couple said moiety to the EBV B-cell antigen.

Accordingly, in another aspect, the present invention relates to a method for preparing the conjugate of the invention, comprising the step of coupling:
 i) a moiety binding to a target cell and/or microorganism, as described above; to
 ii) an Epstein-Barr Virus (EBV) B-cell antigen, as described above.

To do so, said coupling is preferably covalent as described above, so that the moiety and the EBV B-cell antigen remain in close vicinity to achieve in vivo an immune response eliminating the target, in particular through opsonic phagocytosis, ADCC and/or antibody-dependent complement activation.

More preferably, said coupling is a covalent and non-cleavable, in particular in vivo.

According to a preferred embodiment, the coupling is a chemical coupling.

It is within the skill of the person in the art to perform such coupling, with or without a linker as described above. Conventional ways of coupling molecules have notably been described in Bioconjugate techniques by Hermanson, 3rd ed., Elsevier(2013) and Chemistry of Protein and Nucleic Acid Cross-linking and Conjugation by Wong and Jameson, 2d ed., CRC Press (2011).

For example, the EBV-B cell antigen according to the invention can be chemically coupled to the target-binding moiety through its lysine residues (primary amine groups), by using N-Hydroxysuccinimide Ester (NHS ester) reaction chemistry which can provide the formation of a stable bond for in vivo use of the conjugate.

The skilled person in the art would nevertheless understand that chemical coupling may not necessarily be preferred when the immunogenic conjugate is of entire proteic nature. Indeed, in such case, one can directly rely on recombinant engineering and expression techniques in suitable microorganisms (Molecular cloning: A laboratory manual by Sambrook et al., 4th edition, Cold Spring Harbor Laboratory Press–Cold Spring Harbor, N.Y., USA, 2012).

Accordingly, in another aspect, when the conjugate is a fusion protein, the method for preparing the conjugate of the invention preferably comprises the steps of:

a) transforming a host cell with a vector expressing a nucleic acid encoding the immunogenic conjugate of the invention;

b) growing said host cell in a culture medium; and c) recovering the immunogenic conjugate from said medium.

According to a preferred embodiment, said method further comprises the step of d) purifying the immunogenic conjugate obtained in step c).

Complete details for preparing such conjugate are provided in the Examples described further below.

In conjunction with the foregoing, the invention further relates to a nucleic acid encoding the immunogenic conjugate of the invention, to a vector comprising said nucleic acid (e.g., plasmid, bacterial, and viral vectors), and to a host cell transformed with said vector (e.g. prokaryotic or eukaryotic).

It is a further aspect of the invention to provide a pharmaceutical composition comprising at least one immunogenic conjugate as defined above and at least one pharmaceutically acceptable excipient.

As used herein, the term a "pharmaceutically acceptable excipient" means an inactive or inert, and therefore non-toxic, component, as it is has no pharmacological action, which can be used to improve properties of a composition, such as shelf-life, retention time at the application site, consumer acceptance, etc. It includes, without limitation, surfactants (cationic, anionic, or neutral); surface stabilizers; other enhancers, such as preservatives, wetting or emulsifying agents; solvents; buffers; salt solutions; dispersion medium; isotonic and absorption delaying agents, and the like; that are physiologically compatible. Preferred excipients according to the invention include any of the excipients commonly used in pharmaceutical products, such as, for example, microcrystalline cellulose, lactose, starch, and soybean powder.

Said immunogenic conjugate is preferably present in said composition in an amount sufficient to trigger in vivo an immune response eliminating the target of interest, in particular through opsonic phagocytosis, ADCC and/or antibody-dependent complement activation, or in other words in an effective amount. It is within the skill of the person in the art to determine the desired effective amount of conjugate to deliver by routine methods in the art, e.g. by performing a dose-response experiment with varying doses administered to target cells or animals.

In this regard, the pharmaceutical composition of the invention preferably comprises about 0.000001% to about 10%, preferably about 0.000002% to about 5%, and even more preferably about 0.000005 to about 1% by weight of the composition from one or more immunogenic conjugate according to the invention.

The pharmaceutical composition of the invention may be in any form suitable for the purposes of the invention. For example, said composition may be in a form suitable for parenteral, oral or topical administration, such as a liquid suspension, a solid dosage form (granules, pills, capsules or tablets), or a paste or gel. The term parenteral as used herein includes subcutaneous injection, intravenous, or intramuscular injection.

The pharmaceutical composition can also comprise other active agents, which can facilitate the elimination of the target cell and/or microorganism.

According to a preferred embodiment, said pharmaceutical composition further comprises at least one adjuvant, so as to potentiate the immune response mediated by the conjugate. Some adjuvants are indeed capable of favoring and prolonging the duration of interaction between an antigen and the immune system, while others are capable of recruiting and activating cells of the natural immunity so as to induce an adaptive response. The adjuvants belonging to the former category include, without limitation, mineral compounds such as alum, aluminum hydroxide, aluminum phosphate, calcium phosphate hydroxide; oil-based emulsions such as paraffin oil, starch oil, Freund's complete/incomplete adjuvant (FCA/FIA), saponins (e.g. from the plants Quillaja, Soybean, Polygala senega). The adjuvants belonging to the latter category include, without limitation, immunostimulatory complexes (ISCOMs) such as cytokines (e.g. GM-CSF, Il-1, IL-2, IL6, IL8, IL12, TNF-, IFN-, etc); bacterial products such as heat-shock proteins (HSPs), pathogen-associated molecular patterns (PAMPs), trehalose dimicolate (TDM), muramyldipeptide (MDP), lipopolysaccharide (PLS).

According to a preferred embodiment, the pharmaceutical composition may further comprise at least one therapeutic agent directed against the target cell and/or microorganism. Said therapeutic agent is thus preferably capable of preventing and/or treating, in a subject in need thereof, the condition or disease that is characterized by the presence of the unwanted cell and/or microorganism. For example, the therapeutic agent can be an anti-cancer agent, and anti-viral agent, an antibiotic, an anti-fungal agent and/or an anti-parasitic agent. Preferably, said therapeutic agent is an anti-malaria agent, or an anti-cancer agent.

It is within the skill of ordinary person in the art to select the appropriate adjuvant and/or therapeutic agent for the intended purpose.

The adjuvant or the therapeutic agent can also be administered in association with the immunogenic conjugate of the invention, either simultaneously, separately, or sequentially. Should the conjugate, the adjuvant and/or therapeutic agent be administered in a separate or sequential manner, those may be administered in distinct pharmaceutical forms.

Thus, in another aspect, the invention relates to an immunogenic conjugate of the invention and an adjuvant and/or therapeutic agent as described above, as a combined preparation for a simultaneous, separate, or sequential administration in a subject in need thereof. In other terms, the invention proposes a combined use of the immunogenic conjugate of the invention and the adjuvant and/or therapeutic agent for a simultaneous, separate, or sequential administration in a subject in need thereof.

The immunogenic conjugate of the invention, or the pharmaceutical composition comprising said conjugate, may be used in medical applications which can benefit from the capacity of the conjugate to eliminate, in a specific manner, an unwanted cell and/or microorganism in a subject in need thereof.

Thus, in another aspect, the invention relates to an immunogenic conjugate, or a pharmaceutical composition as described above, for use as a medicament.

Preferably, said medicament is intended for triggering opsonic phagocytosis and/or lysis by ADCC and/or lysis by antibody-dependent complement activation of the target cell and/or microorganism in a subject in need thereof. More preferably, said medicament is intended for triggering opsonic phagocytosis of the target cell and/or microorganism in a subject in need thereof.

For example, the immunogenic conjugate or the pharmaceutical composition can be used for destroying diseased cells including notably cancer cells, or cells infected with a pathogen such as a virus, a bacterium, a fungus and/or a parasite, and/or for destroying a pathogenic microorganism such as a virus, a bacterium, a fungus and/or a parasite.

Thus, in a preferred embodiment, the invention relates to the immunogenic conjugate or pharmaceutical composition of the invention, for use in the treatment of cancer, viral infection, bacterial infection, fungal infection and/or parasitic disease in a subject in need thereof. More precisely, the invention relates to the use of the immunogenic conjugate or pharmaceutical composition of the invention for manufacturing a medicament to treat cancer, viral infection, bacterial infection, fungal infection and/or parasitic disease in a subject in need thereof. In other words, the invention relates to a method for treating cancer, viral infection, bacterial infection, fungal infection and/or parasitic disease in a subject in need thereof, comprising administering the immunogenic conjugate or pharmaceutical composition of the invention, to said subject. Methods of administration of a medicament are well-known to the skilled person in the art, and need not be further detailed herein.

A preferred parasitic disease according to the invention is malaria. Another preferred disease according to the invention is cancer.

The term "treating, "treatment" or "treat" as used herein encompasses, among others, preventing, ameliorating, inhibiting, or curing a deficiency, dysfunction, disease, or other deleterious process, including those that interfere and/or result from a therapy.

The term "subject" refers throughout the specification to a human being or an animal, preferably to a human being. Besides, in the context of the present invention, the subject is exhibiting an existing or pre-existing humoral immune response to EBV.

The present invention will be better understood in the light of the following detailed description of experiments, including examples. Nevertheless, the skilled artisan will appreciate that this detailed description is not limitative and that various modifications, substitutions, omissions, and changes may be made without departing from the scope of the invention.

BRIEF DESCRIPTION OF THE DRAWINGS

FIG. 3. Gel filtration chromatography of the conjugates DARC$_{VHH}$-EBV mutated P18 antigen and DARC$_{VHH}$-EBV P18 antigen fragments as well as of the anti-DARC VHH alone. Following IMAC purification, DARC$_{VHH}$-P18 (056S)* (A), DARC$_{VHH}$-P18F2 (B), DARC$_{VHH}$-P18F3 (C), DARC$_{VHH}$-P18F4 (D), and DARC$_{VHH}$ (E) were subjected to size exclusion chromatography.

FIG. 5. Comparative analysis of the affinity of non-conjugated versus conjugated DARC$_{VHH}$ and VAR2CSA$_{VHH}$ for their respective molecular targets, i.e. DARC and VAR2CSA. Full-length recombinant DARC$_{325}$ and VAR2CSA (3D7-DBL1X-6ε) were immobilized on CM5 chips and analytes were injected at different concentrations. The affinity constants of DARC$_{VHH}$-P18F2, DARC$_{VHH}$-P18F3, DARC$_{VHH}$-P18F4, DARC$_{VHH}$ for DARC$_{325}$ and of VAR2CSA$_{VHH}$-P18F2, VAR2CSA$_{VHH}$-P18F3, VAR2CSA$_{VHH}$ for VAR2CSA were not significantly modified by the EBV-antigen conjugations.

EXAMPLES

Figure 1:
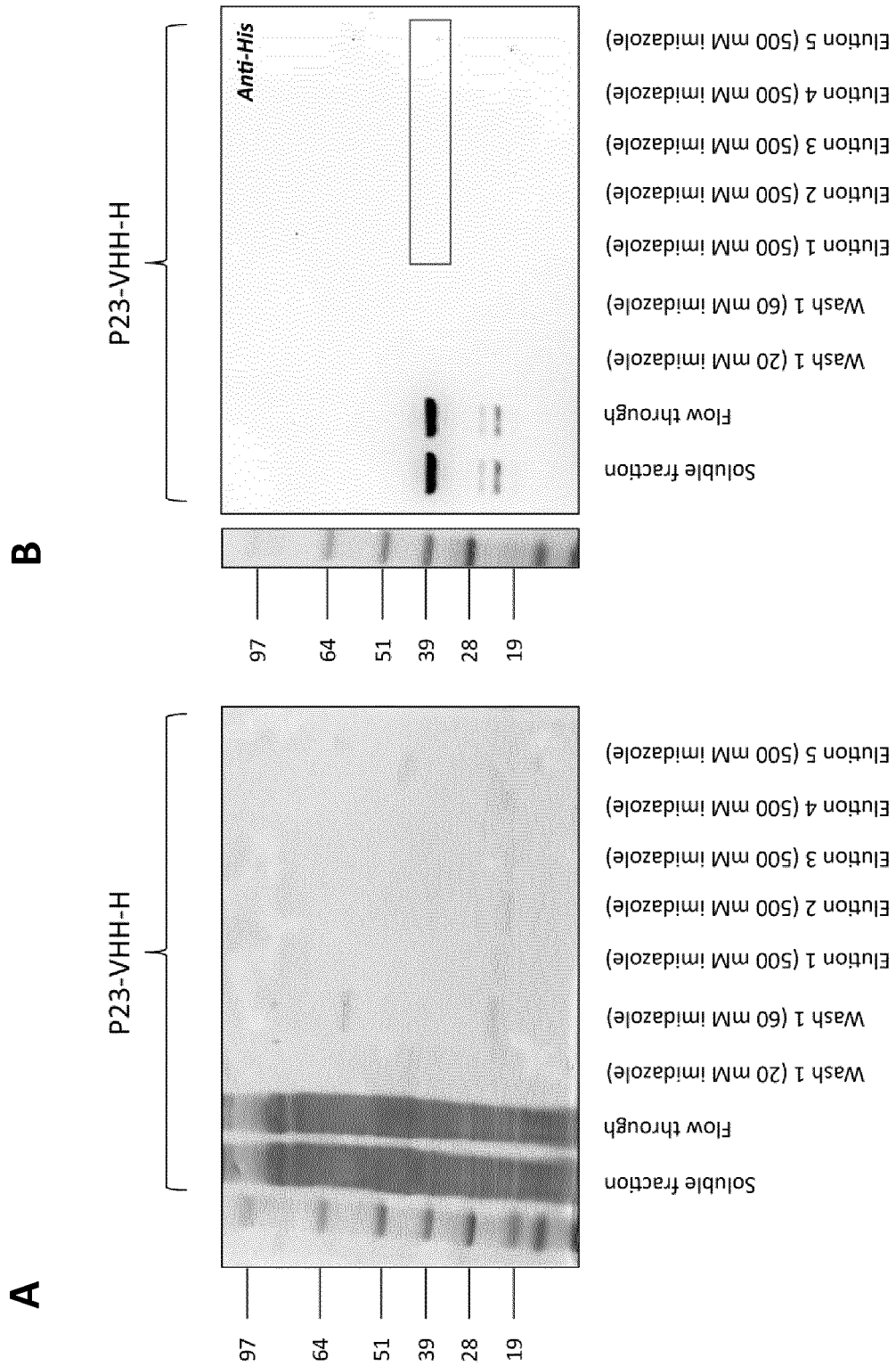
FIG. 1. IMAC purification of the conjugates DARC$_{VHH}$-EBV P18 antigen and DARC$_{VHH}$-EBV P23 antigen. Ni-NTA purification of DARC$_{VHH}$-P23 under native (A-B) or of DARC$_{VHH}$-P18 and DARC$_{VHH}$-P23 under denaturing conditions (C-D). Following SDS PAGE, protein gels were stained with Coomassie blue (A and C) or transferred onto a nitrocellulose membrane for western blot analysis using an anti-His as probing antibody (B and D).
Figure 1:
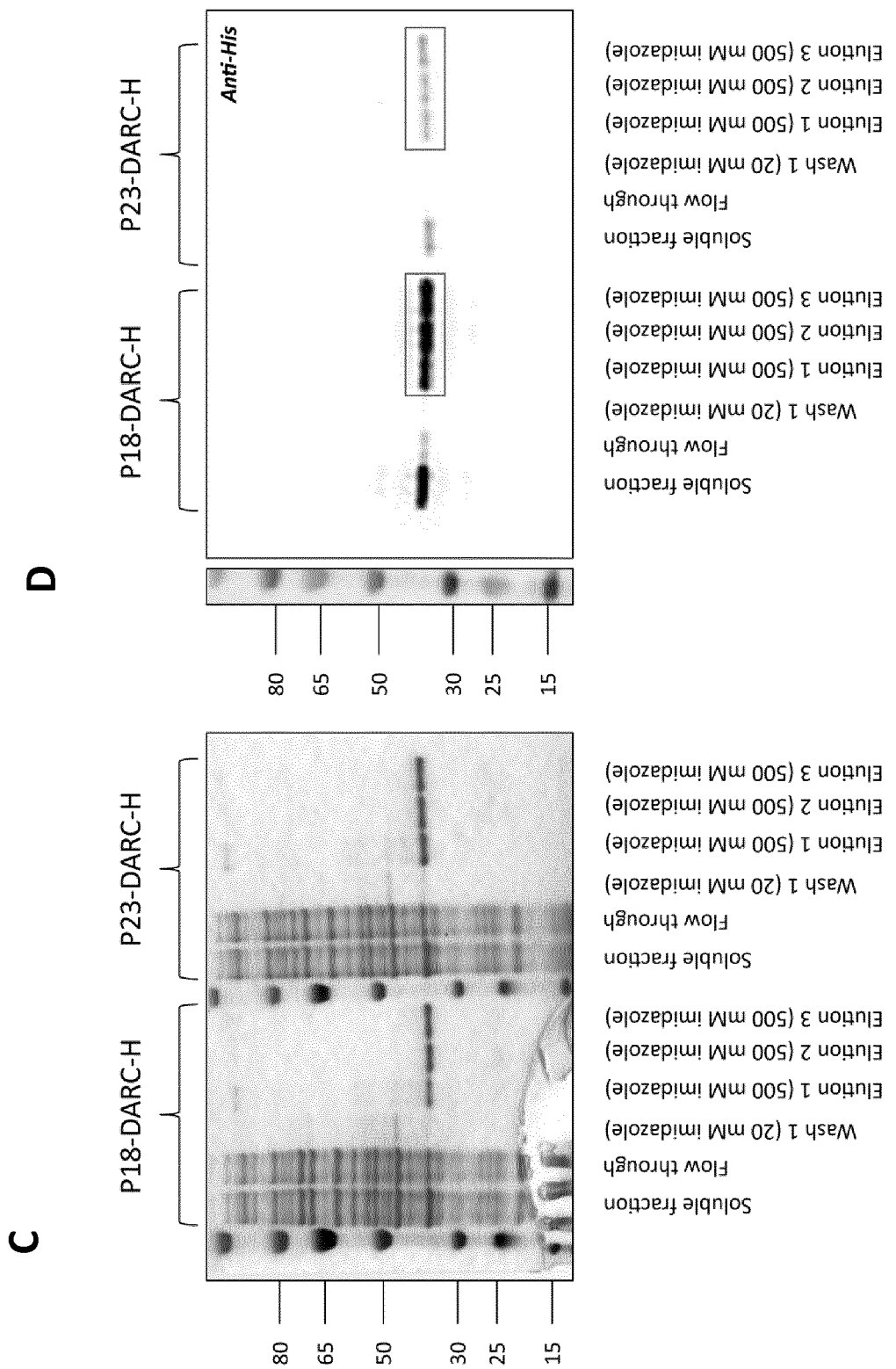

1. Material and Methods 1.1. Construction of the Immunogenic Conjugates According to the Invention The DNA sequences of BFRF3 and BLRF2 encoding for the EBV (B95-8 strain) P18 and P23 proteins were codon-optimized (Integrated DNA Technology) to maximize their expression in *E. coli*. Full length P18 and P23 recoded nucleotide sequences as well as truncated fragments thereof were cloned into the pET28a plasmid (Novagen) in order to express C-terminal His-tagged proteins, for purification purpose.

In some conjugates, a flexible linker of 20 amino-acids $(GGGGS)_4$ (SEQ ID NO: 7) has been added between the binding moiety (VHH, scFv, cell surface receptor, or cell-surface ligand) and the EBV-B cell P18 or P23 antigen in order to maintain, and if possible enhance, the proper functional attributes of the 2 different modules (i.e. of the moiety binding to the target cell and/or microorganism and of the EBV-B cell antigen) (Hu et al., 2004; Chen et al., 2013). The binding moiety sequences (except EPCR) were then inserted between the NcoI and NheI restriction sites of the modified pET28a plasmid. For the EPCR conjugate, the gene encoding soluble EPCR (residues S18-S210; [Uniprot: Q9UNN8; SEQ ID NO:14) was amplified by PCR from a human lung endothelium cDNA library and fused to a recoded gene fragment encoded for P18F3. The EPCR-P18F3 sequence was cloned into a pTT3 vector with a hexa-His C-terminal tag.

In the present study, the following conjugates were thus designed:
- EBV P18 full length antigen fused in frame to $DARC_{VHH}$, with linker;
- EBV P23 full length antigen fused in frame to $DARC_{VHH}$, with linker;
- EBV P18 mutated antigen fused in frame to $DARC_{VHH}$, with and without linker;
- EBV P23 mutated antigen fused in frame to $DARC_{VHH}$, with and without linker;
- various EBV P18 fragments fused in frame to $DARC_{VHH}$, $VAR2CSA_{VHH}$, VAR2CSA, hCD20scFv or EPCR, without linker; and
- various EBV P23 fragments fused in frame to $DARC_{VHH}$, without linker.

These linkers can be summarized in the following Table 1.

TABLE 1

Immunogenic conjugates

| targeting moeity (in N-terminal) | linker | EBV antigen (in C-terminal) | entire corresponding sequence |
|---|---|---|---|
| $DARG_{VHH}$ (SEQ ID NO: 9) Smolarek et al., 2010 | (GGGGS)4 (SEQ ID NO: 7) | P18 (SEQ ID NO: 17) | SEQ ID NO: 61 |
| | (GGGGS)4 (SEQ ID NO: 7) | P18-C565 (SEQ ID NO: 41) | SEQ ID NO: 62 |
| | none | P18-C565 (SEQ ID NO: 41) | SEQ ID NO: 63 |
| | none | P18F2 (SEQ ID NO: 58) | SEQ ID NO: 64 |
| | none | P18F3 (SEQ ID NO: 76) | SEQ ID NO: 77 |
| | none | P18F4 (SEQ ID NO: 52) | SEQ ID NO: 66 |
| $VAR2CSA_{VHH}$ (SEQ ID NO: 11) Nunes et al., 2014 | none | P18F2 (SEQ ID NO: 58) | SEQ ID NO: 67 |
| | none | P18F3 (SEQ ID NO: 76) | SEQ ID NO: 78 |
| | none | P18F4 (SEQ ID NO: 52) | SEQ ID NO: 69 |
| $DARC_{VHH}$ (SEQ ID NO: 9) Smolarek et al., 2010 | (GGGGS)4 (SEQ ID NO: 7) | P23 (SEQ ID NO: 23) | SEQ ID NO: 70 |
| | (GGGGS)4 (SEQ ID NO: 7) | P23-C465 (SEQ ID NO: 42) | SEQ ID NO: 71 |
| | none | P23-C465 (SEQ ID NO: 42) | SEQ ID NO: 72 |
| | none | P23F2 (SEQ ID NO: 60) | SEQ ID NO: 73 |
| | none | P23F3 (SEQ ID NO: 59) | SEQ ID NO: 74 |
| CD20 scFv Otz et al., 2009; Liu et al., 1987 (SEQ ID NO: 80) | none | P18F3 (SEQ ID NO: 76) | SEQ ID NO: 81 |
| VAR2CSA (SEQ ID NO: 82) | none | P18F3 (SEQ ID NO: 76) | SEQ ID NO: 83 |
| EPCR (SEQ ID NO: 14) | none | P18F3 (SEQ ID NO: 76) | SEQ ID NO: 79 |

1.2. Expression and Purification of the Conjugates

For protein expression, SHuffle® E. coli (New England Biolabs) allowing cytoplasmic disulphide bonds formation were transformed with the different pET28a-based conjugates. Bacteria cultures were induced with 0.2 mM IPTG at $OD_{600nm}$ 0.5 and protein expression was carried out at 20° C. for 16 h. For protein purification, bacteria suspensions were thawed on ice and lysis was achieved by passing the cell suspensions through an EmulsiFlex-C5 high-pressure homogenizer. Soluble proteins were subjected to a 2 step purification process. His-tagged proteins were first purified on Ni-NTA Superflow (Qiagen) then passed through a Superdex 200 10/300 GL gel filtration column (GE Healthcare).

In particular, for the EPCR conjugate, FreeStyle 293-F cells (Invitrogen) were grown in Freestyle 293 serum free expression medium and transfected with the pTT3 vector containing the EPCR-P18F3 sequence following Invitrogen's recommendations. 72 hours post-transfection, cells were centrifuged and the culture medium was harvested. After filtration on a 0.22 μm filter, supernatants were concentrated five times using a 10 kDa cut-off Vivaflow 200 System (Vivasciences). Soluble proteins were subjected to a 2 step purification process. His-tagged proteins were first purified on Ni-NTA Superflow (Qiagen) then passed through a Superdex 200 10/300 GL gel filtration column (GE Healthcare).

1.3. Affinity Determination by Surface Plasmon Resonance

Interactions between the conjugates and their respective molecular targets were studied by surface plasmon resonance (SPR), using a Biacore X100 instrument (GE Healthcare). All experiments were performed in HBSEP buffer (GE Healthcare) at 25 uC. Recombinant full-length $DARC_{325}$ or VAR2CSA protein was immobilized on the analysis Fc2 channel of a CM5 chip (GE Healthcare) by amine coupling to a total loading of 800 RU. Reference channel Fc1 was blocked with 1 M ethanolamine-HCl pH 8.5 using the same chemistry. Conjugates were injected at 30 μL/min in dilution series over the coated chips. The highest concentration of conjugates was 1 mM and ten twofold serial dilutions were also injected. Between the injections, the chip surface was regenerated with 2 injections of 15 ml of 10 mM HCl pH2. The specific binding response was obtained by subtracting the response given by the analytes on Fc2 by the response on Fc1. The kinetic sensorgrams were fitted to a global 1:1 interaction Langmuir model using the manufacturer's software.

1.4. Immune Recognition of the Conjugates

ELISA plates (Nunc) were coated with 100 ml per well of conjugates diluted in PBS at 1 μg/ml and incubated at 4° C. overnight. BSA (2% in PBS) was coated for background measurement. After coating, the wells were blocked with PBS 2% BSA at room temperatureT for 1 h. After removing the blocking solution, human plasma dilutions in PBS 2% BSA were added and the plates were incubated at room temperature for 1 h. The wells were then washed 3 times with 150 ml of PBS 0.05% Tween20 (PBST). Human IgG binding was detected with a horseradish peroxidase-conjugated (HRP) anti-human IgG (Jackson Immunoresearch 709-036-098), diluted 1:4000 in PBS 2% BSA, incubated at room temperature for 1 h. After washing with PBST, the plates were developed with 100 ml per well of TMB (3,39,5,59-tetramethylbenzidine) substrate (Biorad) and absorbance was measured at 655 nm.

1.5. Cell Surface Recognition by the Conjugates

The capacity of the $DARC_{VHH}$-EBV conjugates to recognize the native DARC expressed at the surface of erythrocytes, the one of the $hCD20_{ScFv}$-P18F3 conjugate to recognize the native CD20 protein expressed at the surface of B cells, the one of the VAR2CSA-P18F3 conjugate to recognize the native glycosaminoglycan chondroitin sulfate A (CSA) expressed at the surface of cancer cells, and the one of the EPCR-P18F3 conjugate to recognize the native VAR19 protein expressed at the surface of Plasmodium falciparum-infected cells, were tested by flow cytometry.

To do so, DARC+ erythrocytes (for $DARC_{VHH}$-EBV conjugates), CD20+ RAJI cells (for the $hCD20_{ScFv}$-P18F3 conjugate), CSA+ RAJI cells (for the VAR2CSA-P18F3 conjugate) or VAR19-expressing erythrocytes (for the EPCR-P18F3 conjugate) were incubated with serial dilution of conjugate in PBS 2% BSA, for 1 h at room temperature. The cells were then washed twice with PBS 2% BSA and incubated for 30 min at room temperature with a mouse anti-PentaHis IgG (Qiagen, Cat.no.34660) at 5 mg/ml diluted in PBS 2% BSA. After 30 min, cells were washed twice with PBS 2% BSA and incubated for 30 min at room temperature with a PE-conjugated goat F(ab')2 anti-mouse IgG (Beckman Coulter, IM0855, diluted 1:100 in PBS 2% BSA). Cells were washed with PBS and subjected to flow cytometry analysis. Data was acquired using a BD FACScanto II flow cytometer (Becton-Dickinson, San Jose, Calif.) and analysis was performed using the FLOWJO 8.1 software (Tree Star Inc.). Cellular debris were excluded from the analysis by appropriated gating using the forward and side scatters.

The reactivity of the tested conjugates to surface-expressed DARC (for $DARC_{VHH}$-EBV conjugates), to surface of RAJI cells (for the $hCD20_{ScFv}$-P18F3 and VAR2CSA-P18F3 conjugates), or to surface-expressed VAR19 (for the EPCR-P18 conjugate) was reflected by an increase geometric mean in fluorescence intensity in the PE channel (Geometric Mean PE).

1.6. Opsonization Assays

For opsonization assays, DARC+ erythrocytes were incubated with a constant concentration of the $DARC_{VHH}$-EBV conjugates in PBS 2% BSA, for 1 h at room temperature. The cells were then washed twice with PBS 2% BSA and incubated for 1 h at room temperature with serial dilutions of human plasma in PBS 2% BSA. Cells were then washed twice with PBS 2% BSA and incubated for 30 min at room temperature with a PE-conjugated donkey F(ab')2 anti-human IgG (Jackson Immunoresearch 709-116-098, diluted 1:100 in PBS 2% BSA). Cells were washed with PBS and subjected to flow cytometry analysis.

By contrast, RAJI cells were incubated with serial dilutions of the $hCD20_{ScFv}$-P18F3 or VAR2CSA-P18F3 conjugate in PBS 2% BSA, for 1 h at room temperature. These cells were then washed twice with PBS 2% BSA and incubated for 1 h at room temperature with a constant human plasma dilution (1:100) in PBS 2% BSA. Said cells were then washed according to the same protocol as the one applied for DARC+ erythrocytes.

1.7. Opsonic Phagocytosis Assays

The non-adherent human monocyte cell line THP-1 (Sigma) was maintained in 150 $cm^2$ flasks with RPMI 1640 medium supplemented with 10% (v/v) fetal bovine serum (Gibco, Grand Island, N.Y.), 2 mM L-Glutamine, 100 units/ml penicillin and 100 ug/ml streptomycin (THP-1 culture medium). The cells were subcultured every 3 days and density was maintained at less than $2 \times 10^5$ cells per ml; cultures were kept in a humidified 37° C. incubator with 5% (v/v) $CO_2$ and 95% (v/v) air.

THP-1 cells were seeded at 2.5×10⁵ cells per well in 6-well plates and the volume of each well was made to 3 ml with THP-1 culture media. To obtain macrophages, the cells were differentiated using 10 ng/ml phorbol 12-myristate 13-acetate for 24 h in 5% (v/v) $CO_2$ at 37° C. The supernatant and unattached cells were removed by aspiration and adherent macrophages were washed twice with THP-1 culture medium before the wells were filled with 3 ml of fresh THP-1 culture medium. These were further incubated for 48 h before performing phagocytic assay.

Erythrocytes were labeled with CellTrace™CFSE according to the manufacturer's instructions and opsonized with the conjugates and human plasma as described above. Labeled and opsonized erythrocytes were co-inbubated with THP-1 derived macrophages for 3 h. Erythrocytes were washed out from the wells and macrophages were then detached by trypsin treatment and subjected to flow cytometry analysis. CFSE positive THP-1 cells were regarded as cells having phagocyted at least one erythrocyte.

1.8. Complement Activation Assay

For complement activation assays, RAJI cells were incubated with 5 µg/ml of $hCD20_{ScFv}$ or $hCD20_{ScFv}$-P18F3 in PBS 1% BSA for 1 h at 4° C. The cells were then washed twice with PBS 1% BSA and incubated for 1 h at 37° C., 5% $CO_2$ with 10% EBV⁺ human plasma, in its active form of pre-inactivated by heat treatment (56° C. for 45 min). The cells were then washed three times with PBS and fixed with 4% PFA at room temperature for 15 min. The cells were then washed three times with PBS 5% BSA and blocked with PBS 5% BSA for 1 h at room temperature and then incubated with a mouse monoclonal antibody anti-C5b9 (Abcam ab66768, 1:100 in PBS 1% BSA). The cells were then washed three times with PBS 1% BSA and incubated for 30 min at room temperature with a PE-conjugated goat F(ab')2 anti-mouse IgG (Beckman Coulter, IM0855, diluted 1:100 in PBS 1% BSA). Cells were washed with PBS and subjected to flow cytometry analysis. Data was acquired using a BD FACScanto II flow cytometer (Becton-Dickinson, San Jose, Calif.) and analysis was performed using the FLOWJO 8.1 software (Tree Star Inc.). Cellular debris were excluded from the analysis by appropriated gating using the forward and side scatters. The C5-b9 deposition at the surface of RAJI cells was reflected by an increased fluorescence intensity in the PE channel.

1.9. Antibody-Dependent Cell Cytotoxicity (ADCC) Assay

For ADCC assays, RAJI cells were maintained at a density of 2.5.10⁵-10⁶ cells/ml in RPMI (Glutamax™-I) supplemented with 10% FCS and 1× antibiotic-antimycotic solution (Gibco) at 37° C., 5% $CO_2$. ADCC assays were performed using the ADCC Reporter Bioassay (Promega) according to manufacturer's instructions with slight modifications to fit our system. 300000 RAJI cells were first washed twice with PBS 2% BSA and incubated for 1 h at 4° C. with saturating concentration of conjugates (25 µg/ml $hCD20_{ScFv}$, $hCD20_{ScFv}$-P18F3 or 50 µg/ml VAR2CSA, VAR2CSA-P18F3. Cells were then washed once with PBS 2% BSA and 12500 cells (in 25 µl) were introduced into the wells of white, flat bottom 96-well plates. EBV⁺ human plasma was inactivated/decomplemented at 56° C. for 45 min. Serial dilutions were prepared in ADCC assay medium (RPMI 1640, 4% low IgG FCS) and 25 µl of diluted plasma were introduced to the wells together with the RAJI target cells. Effector cells were thawed and 75000 cells (in 25 µl) were immediately distributed into the wells. Plates were incubated at 37° C., 5% $CO_2$. After 6 h incubation, plates were removed from the incubator and let at room temperature for 15 min before addition of 75 µl of Bio-Glo™ reagent into each well. Luminescence was measured using a VICTOR plate reader platform (PerkinElmer).

2. Results 2.1. Expression and Purification of the Conjugates

The IMAC (Immobilized Metal ion Affinity Chromatography) purification in native conditions of the conjugates $DARC_{VHH}$-EBV P18 and $DARC_{VHH}$-EBV P23 (anti-$DARC_{VHH}$ fused to EBV P18 or EBV P23 antigen, respectively, each of said antigen being tagged in C-terminal with a poly-histidine sequence) was not successful (FIG. 1A-B). Indeed, the C-terminal His-tag was not accessible in native conditions as demonstrated by the successful purification of these conjugates by IMAC under denaturating conditions (FIG. 1C-D). Attempts to purify N-terminal His-tagged fusions did not lead to better results.

Figure 2:
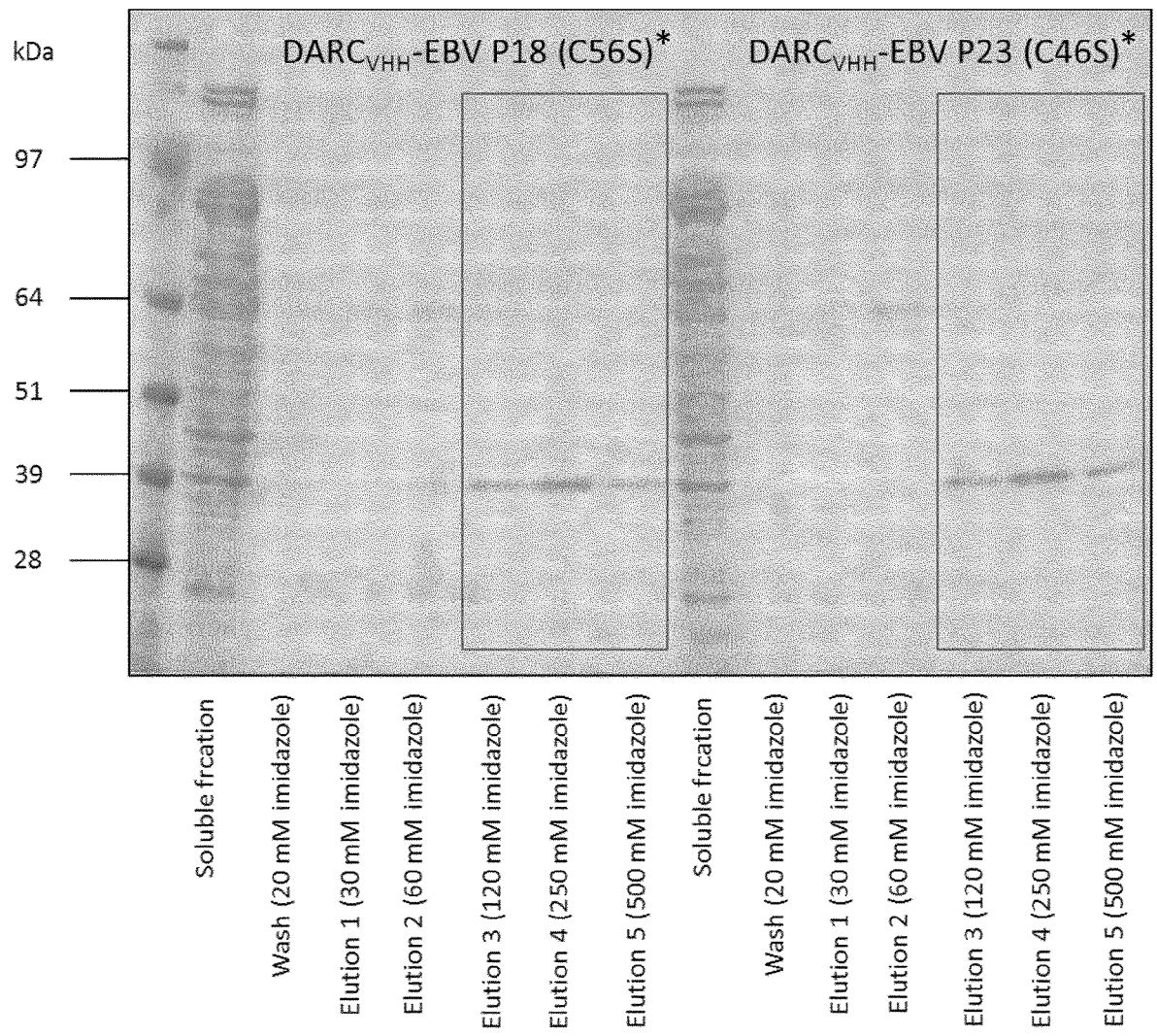
FIG. 2. IMAC purification of the conjugates DARC$_{VHH}$-EBV mutated P18 antigen and DARC$_{VHH}$-EBV mutated P23 antigen. Ni-NTA purification of the mutated conjugates DARC$_{VHH}$-P18 (C56S)* and DARC$_{VHH}$-P23 (C46S)* under native conditions. Following SDS PAGE, protein gels were stained with Coomassie blue.
Figure 3:
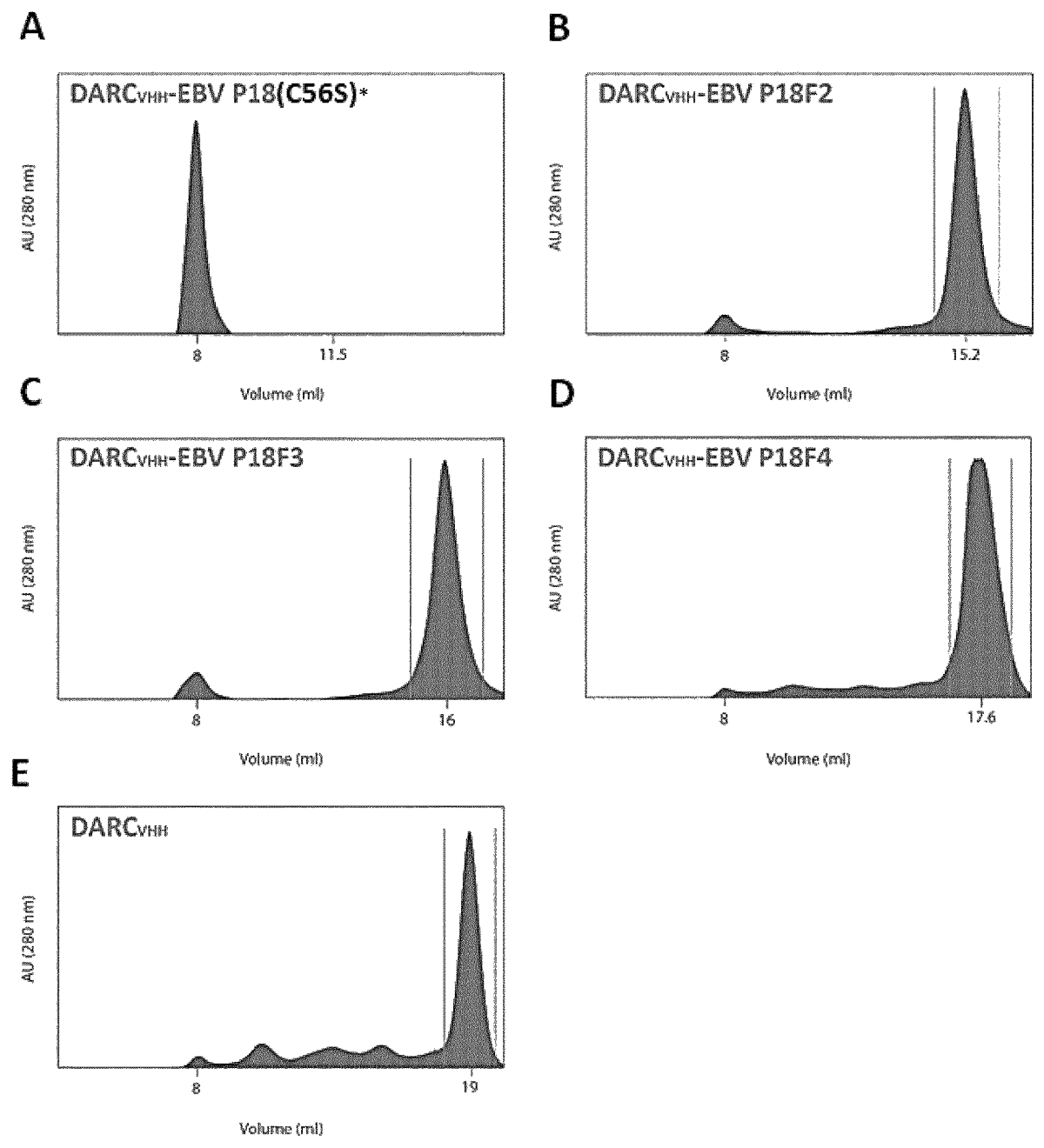
Figure 4:
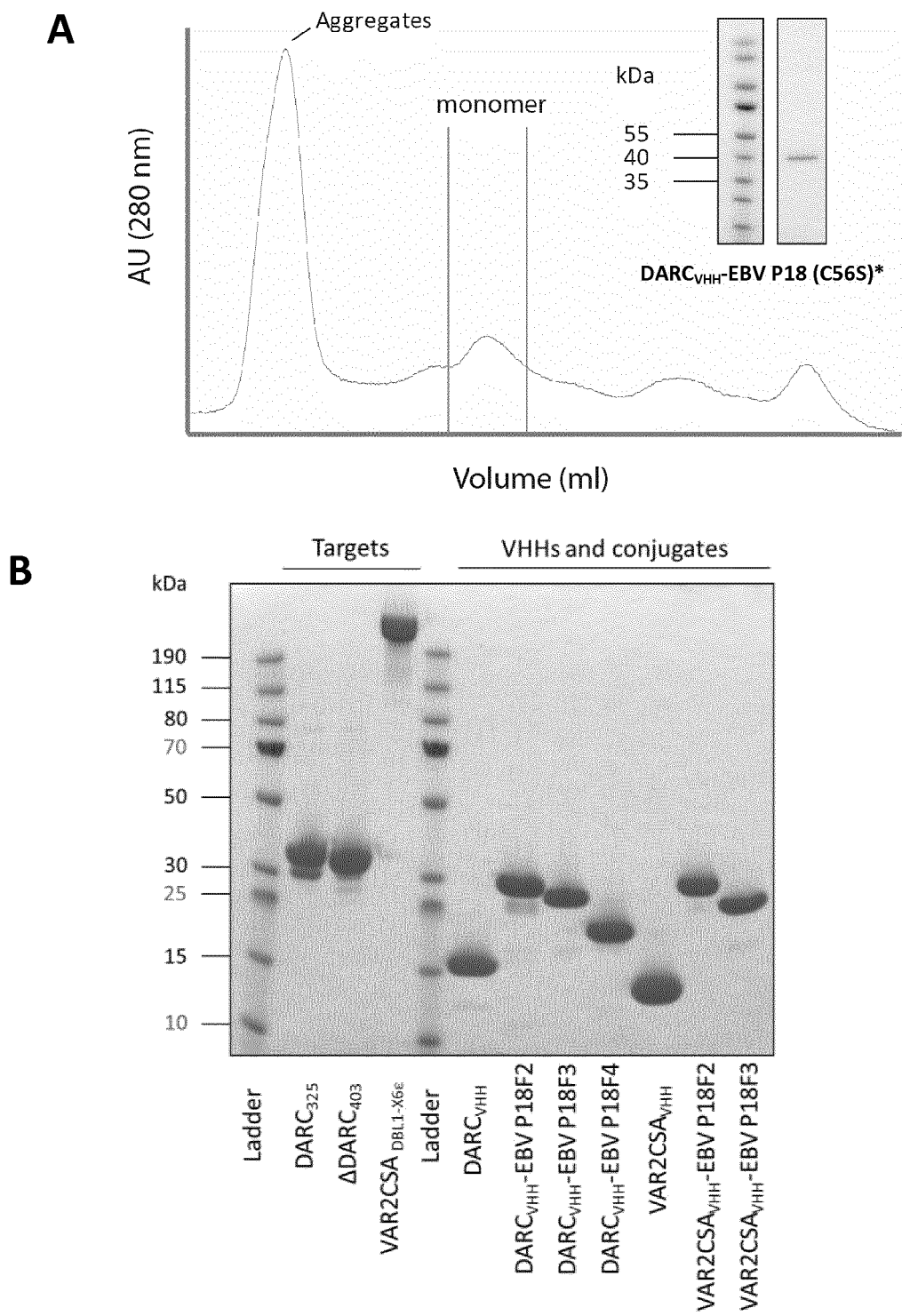
FIG. 4. IMAC purification and gel filtration chromatography purification of the conjugates DARC$_{VHH}$-EBV P18 and VAR2CSA$_{VHH}$-EBV P18 (mutated and fragments). Following IMAC purification, DARC$_{VHH}$-P18(C56S)* was subjected to size exclusion chromatography (A). Coomassie blue staining of purified conjugates DARC$_{VHH}$-P18 fragments and VAR2CSA$_{VHH}$-P18F2 fragments as well as of their purified respective molecular targets DARC and VAR2CSA (B). The recombinant DARC$_{325}$ protein contains the epitope targeted by DARC$_{VHH}$, whereas the recombinant DARC$_{403}$ lacks the epitope sequence. The full-length extracellular part of VAR2CSA comprises the 6 DBL domains (DBL1-DBL6ε), VAR2CSA$_{VHH}$ targeting the DBL4 ε domain.

A site-directed mutagenesis substituting the EBV P18 Cys (in amino-acid position 56) and the EBV P23 Cys (in amino-acid position 46) by serines was performed. The new conjugates $DARC_{VHH}$-EBV P18 (C56S)* and DARC-EBV P23 (C46S)* were successfully purified by IMAC (FIG. 2). Nevertheless, the second step of the purification process (chromatography) revealed that a large proportion of the fusion proteins tended to form aggregates even in high-salt buffers (FIGS. 3A and 4A).

To overcome this problem, shorter variants pf P18 and P23 were designed. The resulting fusion proteins $DARC_{VHH}$-EBV P18F2, $DARC_{VHH}$-EBV P18F3, $DARC_{VHH}$-EBV P18F4 considerably gained in solubility compared to $DARC_{VHH}$-EBV P18(C56S)* and formed very little aggregates during the gel filtration purification step (FIG. 3B-E). A similar approach was performed to improve $DARC_{VHH}$-EBV P23 (C46S)* solubility (data not shown).

In order to extend the proof of concept to another conjugation system, a VHH sequence capable to recognize a P. falciparum protein present at the surface of erythrocytes of placental origin infected by P. falciparum ($VAR2CSA_{VHH}$) was also fused to the EBV P18 and EBV P23 antigens. Similarly to the $DARC_{VHH}$ conjugates, removal of N-terminal clusters of EBV P18 and EBV P23 drastically improved conjugate solubility and stability in solution. Gel electrophoresis analysis of all the produced constructs revealed the high purity of the recombinant proteins used in the study (FIG. 4B,).

The affinity of the $DARC_{VHH}$-EBV P18 antigen conjugates and of the $VAR2CSA_{VHH}$ EBV P18 antigen conjugates for their respective molecular target was assessed by surface plasmon resonance. The specificity and affinity of the conjugates for their targets was not significantly modified in comparison to the affinity of the VHHs alone (FIG. 5).

Figure 10:
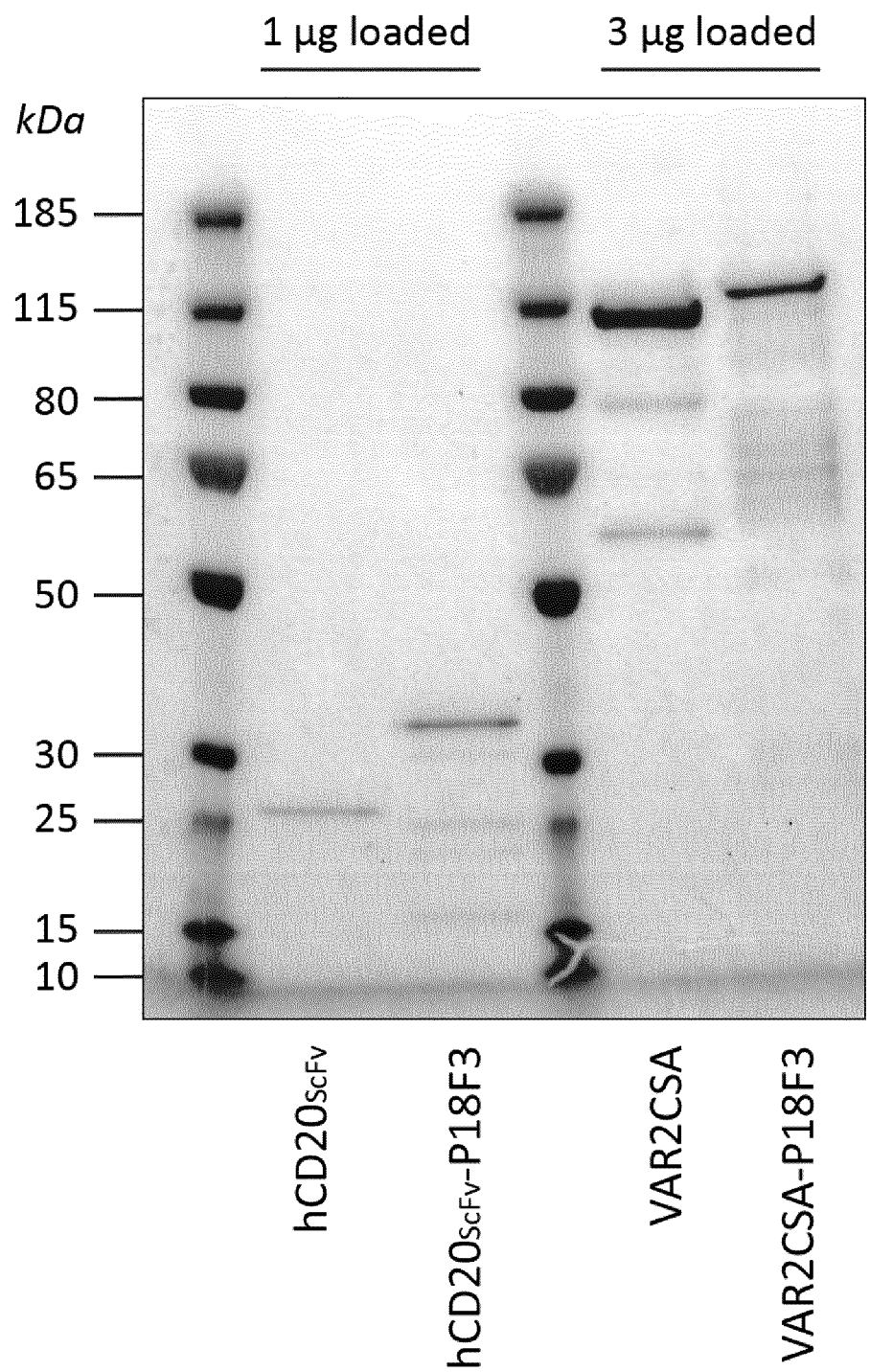
FIG. 10. IMAC purification and gel filtration chromatography purification of the hCD20$_{ScFv}$-P18F3 and VAR2CSA-P18F3 conjugates. Following IMAC purification, hCD20$_{ScFv}$-P18F3 and VAR2CSA-P18F3 were subjected to size exclusion chromatography. Coomassie blue staining of hCD20$_{ScFv}$-P18F3, VAR2CSA-P18F3 and of the "naked" proteins hCD20$_{ScFv}$ and VAR2CSA.
Figure 16:
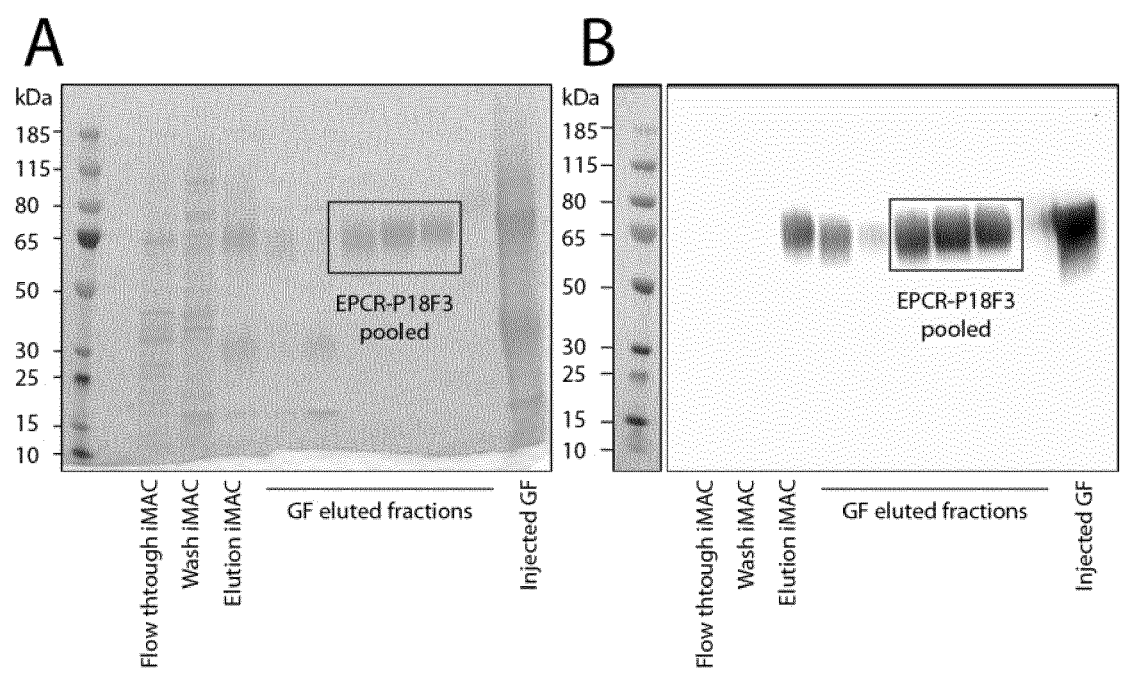
FIG. 16. IMAC purification and gel filtration chromatography purification of the conjugate EPCR-P18F3. Following IMAC purification, EPCR-P18F3 was subjected to size exclusion chromatography. (A) Coomassie blue staining of EPCR-P18F3 and (B) western blot analysis using an anti-His antibody. Gel filtration (GF) fractions containing purified EPCR-P18F3 were pooled and used in functional assays.

The proof of concept of the invention was further validated with three other conjugation systems:
- a scFv sequence capable of recognizing CD20 (a marker typically overexpressed by cancer cells) fused to the EBV P18F3 antigen, of which the purification was successful (FIG. 10); and
- the EPCR receptor fused to the EBV P18F3 antigen, of which the purification was also successful (FIG. 16).
- The VAR2CSA variant protein fused to the EBV P18F3 antigen, of which the purification was also successful (FIG. 10)

2.2. Immune Recognition of the Conjugates

Figure 6A:
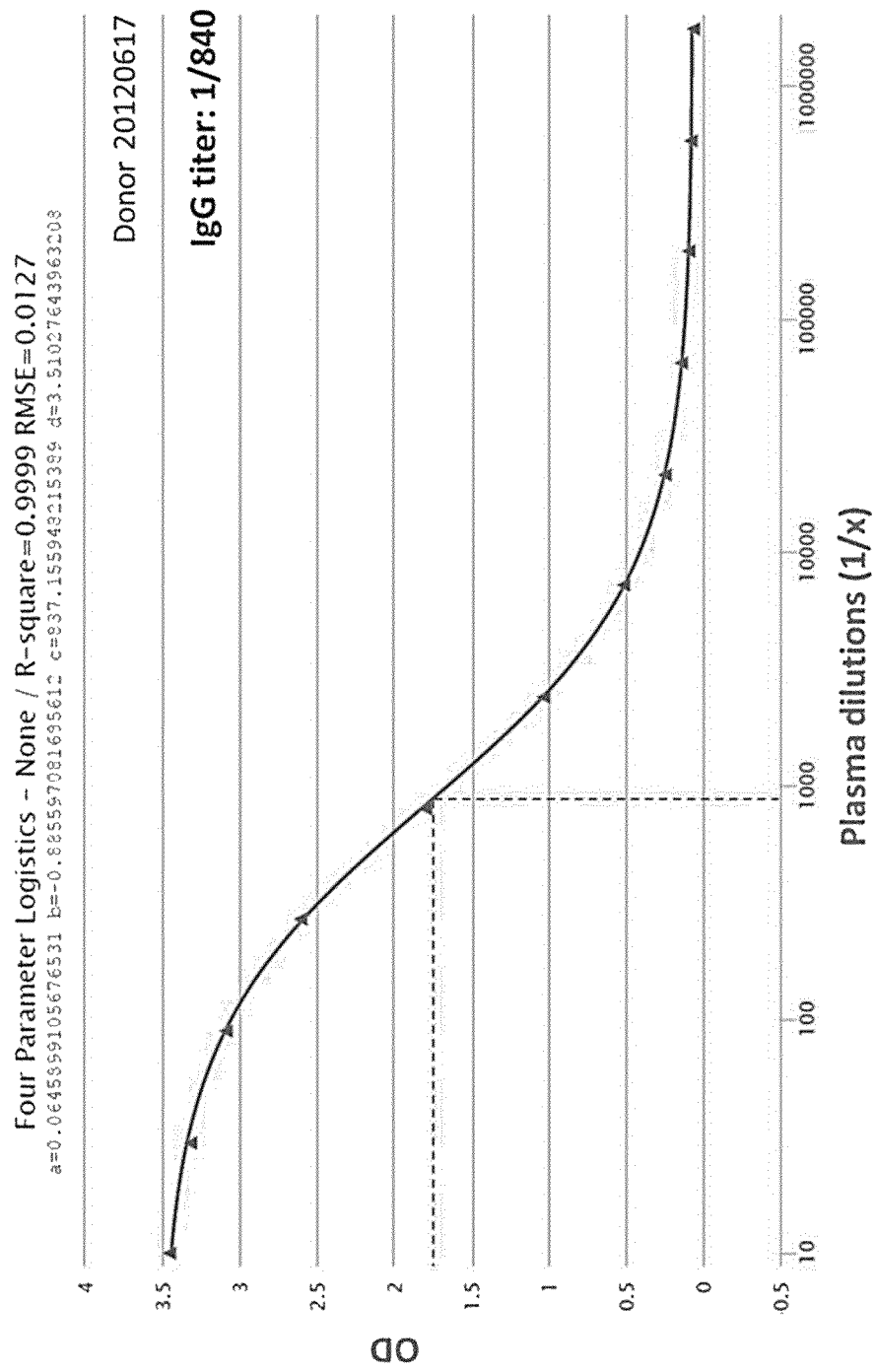
FIG. 6. Immune recognition of the DARC$_{VHH}$-EBV P18 and VAR2CSA$_{VHH}$-EBV P18 conjugates (fragments). Example of antibody titer (IgG) determination towards DARC$_{VHH}$-EBV P18F2. The antibody titer for donor 20120617 was regarded as the plasma dilution at which 50% of the maximum OD signal was reached (A). Comparative immune recognition (IgG) by 22 different plasma samples of DARC$_{VHH}$-P18F2, DARC$_{VHH}$-P18F3, DARC$_{VHH}$-P18F4, DARC$_{VHH}$, VAR2CSA$_{VHH}$-P18F2, VAR2CSA$_{VHH}$-P18F3, VAR2CSA$_{VHH}$ and of MBP EBV-P18 and MBP P23 (B). BSA and MBP were used as controls.

Immunoglobulin G titers, reflecting the immune recognition of the conjugates, were determined by serial dilutions of plasma from 12 healthy donors positive for EBV infection. $DARC_{VHH}$-EBV P18F2 was highly recognized by the IgG present in said plasma (Table 2 and FIG. 6A). Similar data were obtained with the conjugates $DARC_{VHH}$-EBV P18 (C56S)*, and $DARC_{VHH}$-EBV P23 (C46S)*.

TABLE 2

IgG titers (anti-DARCVHH-EBV P18F2) in plasma from 12 EBV+ donors.

| Donor ID | IgG titers |
| --- | --- |
| #20120621 | 460 |
| #20120617 | 840 |
| #20120312 | 230 |
| #20120327 | 190 |
| #20121029 | 130 |
| #20120618 | 70 |
| #20121001 | 440 |
| #20120220 | 120 |
| #20130313 | 360 |
| #20120820 | 60 |
| #20150217I | 430 |
| #20150217II | 2300 |
| Mean (SD): 470 (618) | |

A comparative immune recognition study performed with 22 plasma samples (dilution 1/200) showed that the C-terminal part of P18 possesses immuno-dominant epitopes. No significant differences in recognition was observed between conjugates comprises EBV P18F2 and EBV P18F3.

2.3. Cell Surface Recognition of the Conjugates

Recognition of the native target by the conjugates was assessed by flow cytometry.

Figure 7:
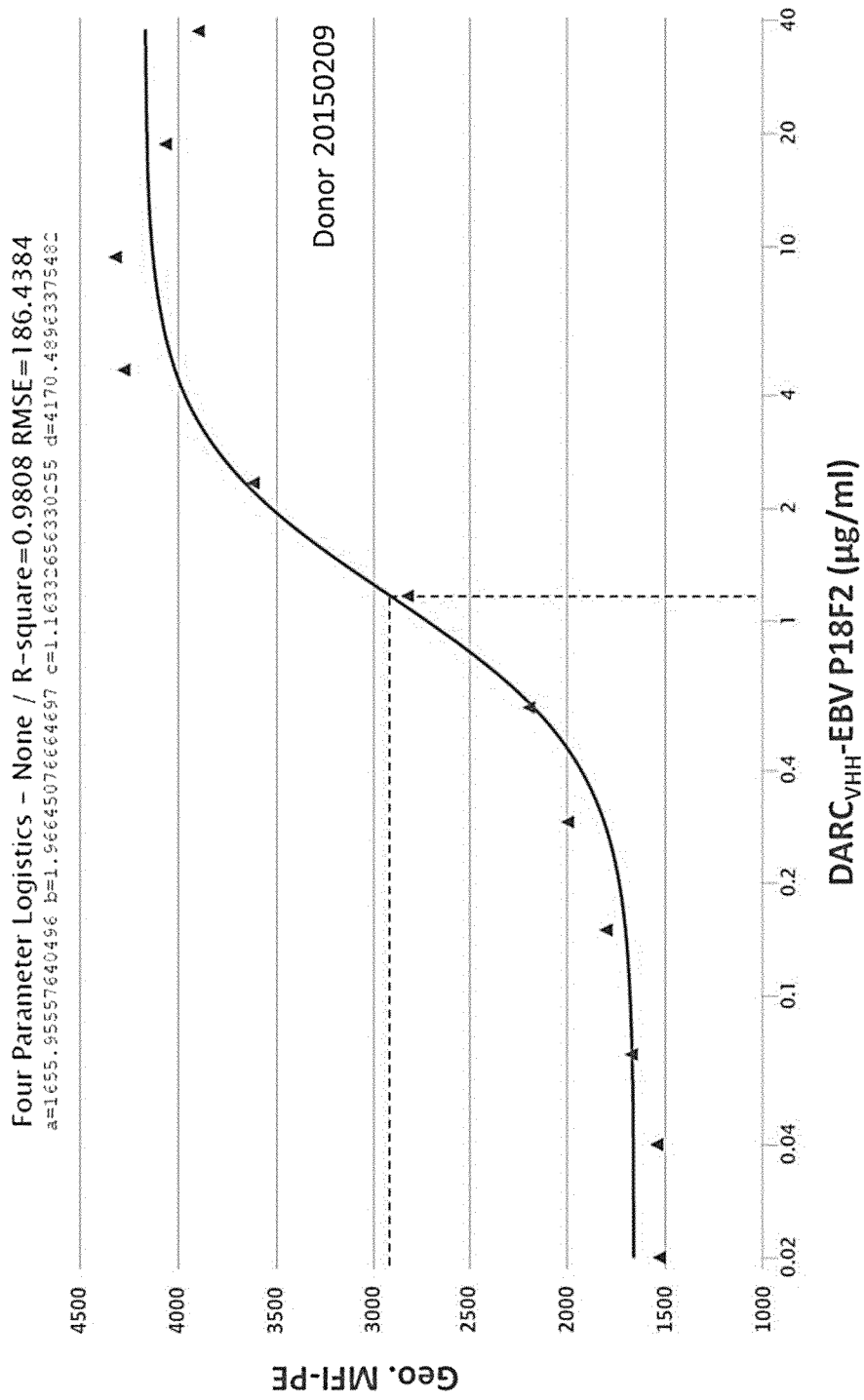
FIG. 7. Binding of the conjugate DARC$_{VHH}$-EBV P18 antigen fragment F2 to its native target, i.e. DARC expressed at the erythrocyte surface of a DARC+ donor. DARC+ erythrocytes were incubated with serial dilutions of DARC$_{VHH}$-P18F2. Membrane bound protein was monitored by flow cytometry using an anti-His PE-conjugated antibody.

$DARC_{VHH}$-EBV P18F2 was able to coat the surface of FY+ (DARC+) erythrocytes in a dose dependent manner (FIG. 7). Less than 250 ng of $DARC_{VHH}$-EBV P18F2 was sufficient to saturate all the VHH-specific DARC-epitopes present on 1,000,000 red blood cells. In a similar manner, $VAR2CSA_{VHH}$-EBV P18F2 was able to coat P. falciparum infected erythrocytes expressing VAR2CSA on their surface.

Figure 11:
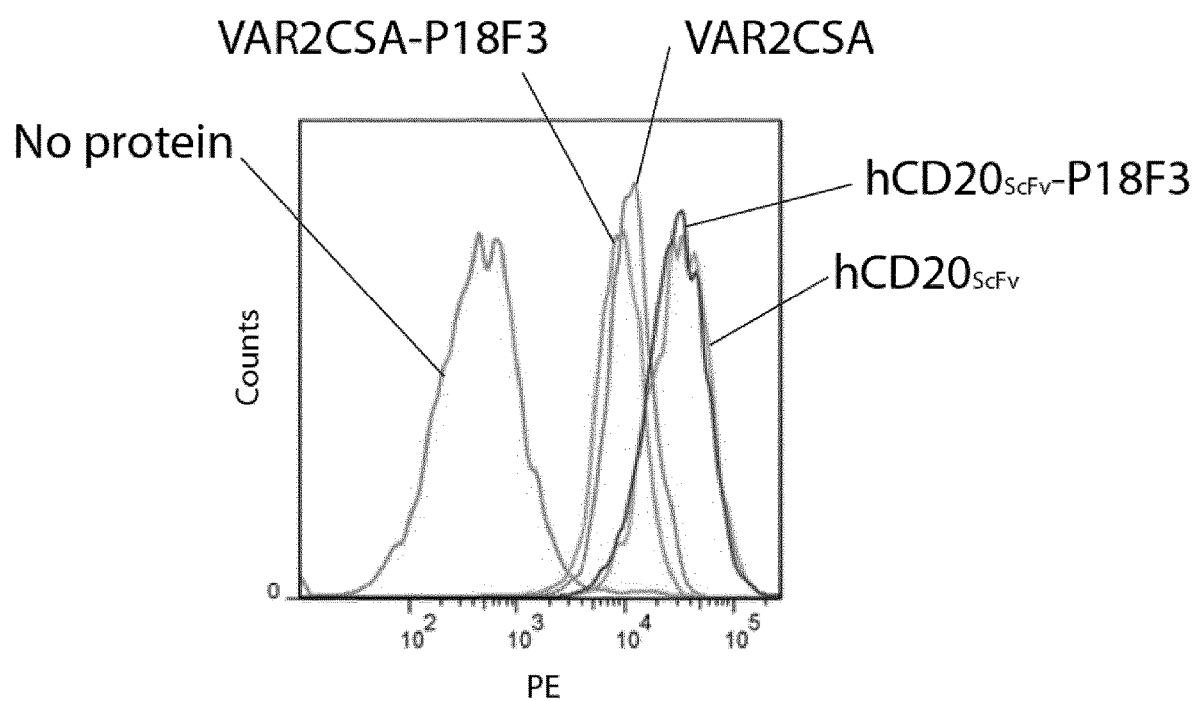
FIG. 11. Binding of the hCD20$_{ScFv}$-P18F3 and VAR2CSA-P18F3 conjugates to their native target, i.e CD20 expressed at the surface of B cells and CSA expressed at the surface of cancer cells, respectively. CD20- and CSA-expressing RAJI cells were incubated with 50 µg/ml of hCD20$_{ScFv}$, hCD20$_{ScFv}$-P18F3 or 50 µg/ml of VAR2CSA, VAR2CSA-P18F3. Membrane bound protein was monitored by flow cytometry using a mouse anti-His antibody and an anti-mouse IgG-PE-conjugated antibody.

The $hCD20_{ScFv}$-P18F3 conjugate was able to coat CD20+ RAJI cells (FIG. 11).

The VAR2CSA-P18F3 conjugate was able to coat CSA+ RAJI cells (FIG. 11).

Figure 17:
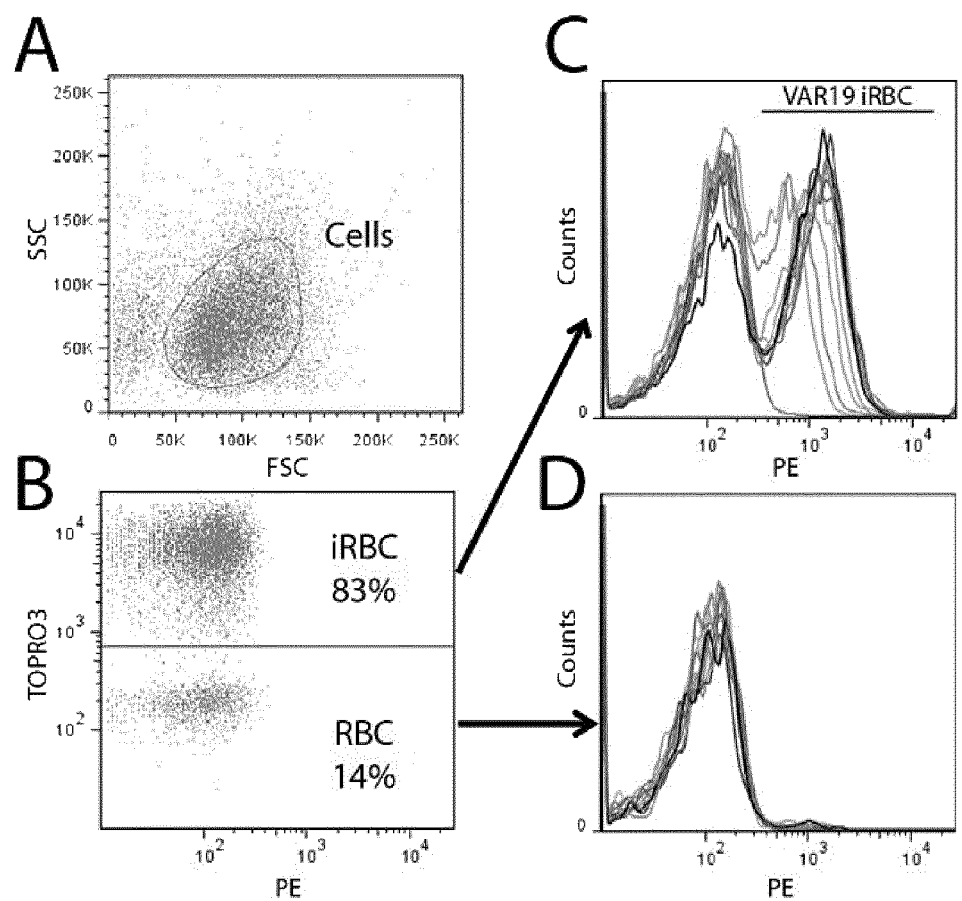
FIG. 17. Binding of the conjugate EPCR-P18F3 to its native target, i.e VAR19 expressed at the surface of Pf. infected erythrocytes. VAR19-expressing infected erythrocytes (iRBC) were incubated with serial dilutions of EPCR-P18F3 (ranging from 100 µg/ml to 0.19 µg/ml). Membrane bound protein was monitored by flow cytometry using a mouse anti-His antibody and an anti-mouse IgG-PE-conjugated antibody. (A) Morphological gating of cells. (B) TOPRO3 staining allowing the discrimination between infected red blood cells (iRBC) and non-infected red blood cells (RBC). Detection of membrane bound EPCR-P18F3 in (C) the iRBC population and (D) in the RBC population.

The EPCR-P18F3 conjugate was able to coat the surface of VAR19-expressing erythrocytes, in a dose dependent manner (FIG. 17).

2.4. Erythrocytes Opsonization by the Conjugates Targeting Said Cells

Figure 8A:
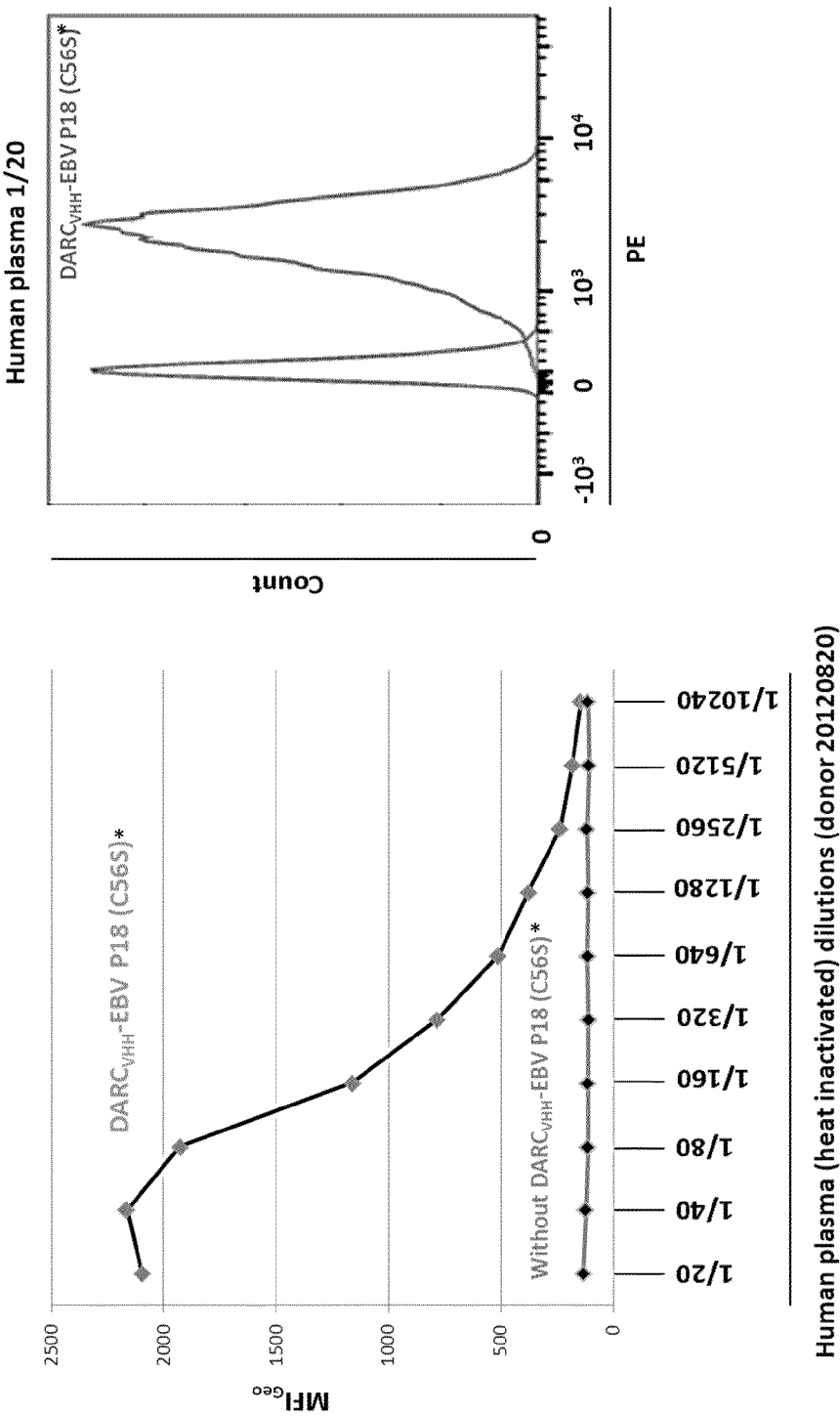
FIG. 8. Erythrocytes opsonization mediated by DARC$_{VHH}$-EBV P18 conjugates (mutated and fragments). (A) In order to demonstrate erythrocytes opsonization, DARC+ erythrocytes were incubated with DARC$_{VHH}$-P18 (C56S)*, and subsequently with serial dilutions of human plasma (left panel). Membrane associated IgG were detected by flow cytometry using an anti-hIgG PE-conjugated antibody (right panel). A shift in fluorescence intensity (PE) reflects the presence of an immune complex at the erythrocyte cell surface (right panel) (B). Erythrocytes agglutination mediated by the conjugate DARC$_{VHH}$-EBV P18 antigen fragment F3. DARC+ erythrocytes were incubated with DARC$_{VHH}$-P18F3 and subsequently with serial dilutions of human plasma. Following centrifugation of the plate, erythrocytes from control conditions (without human plasma) formed a well-defined cell pellet (a,b,c) whereas erythrocytes incubated in presence of DARC$_{VHH}$-P18F3 and human plasma formed diffused agglutinates (d, e, f) (B).

Furthermore, incubation of cell-bound conjugates with plasma samples of EBV+ donors led to FY+ (DARC+) erythrocytes opsonization, i.e. coating of cells with the donor plasma IgG (FIG. 8A). This was also illustrated in agglutination assays where successive incubation of FY+ erythrocytes with $DARC_{VHH}$-EBV P18F3 and human plasma (EBV positive) led to cell agglutination (FIG. 8B).

2.5. Opsonic Phagocytosis Assays

Figure 18:
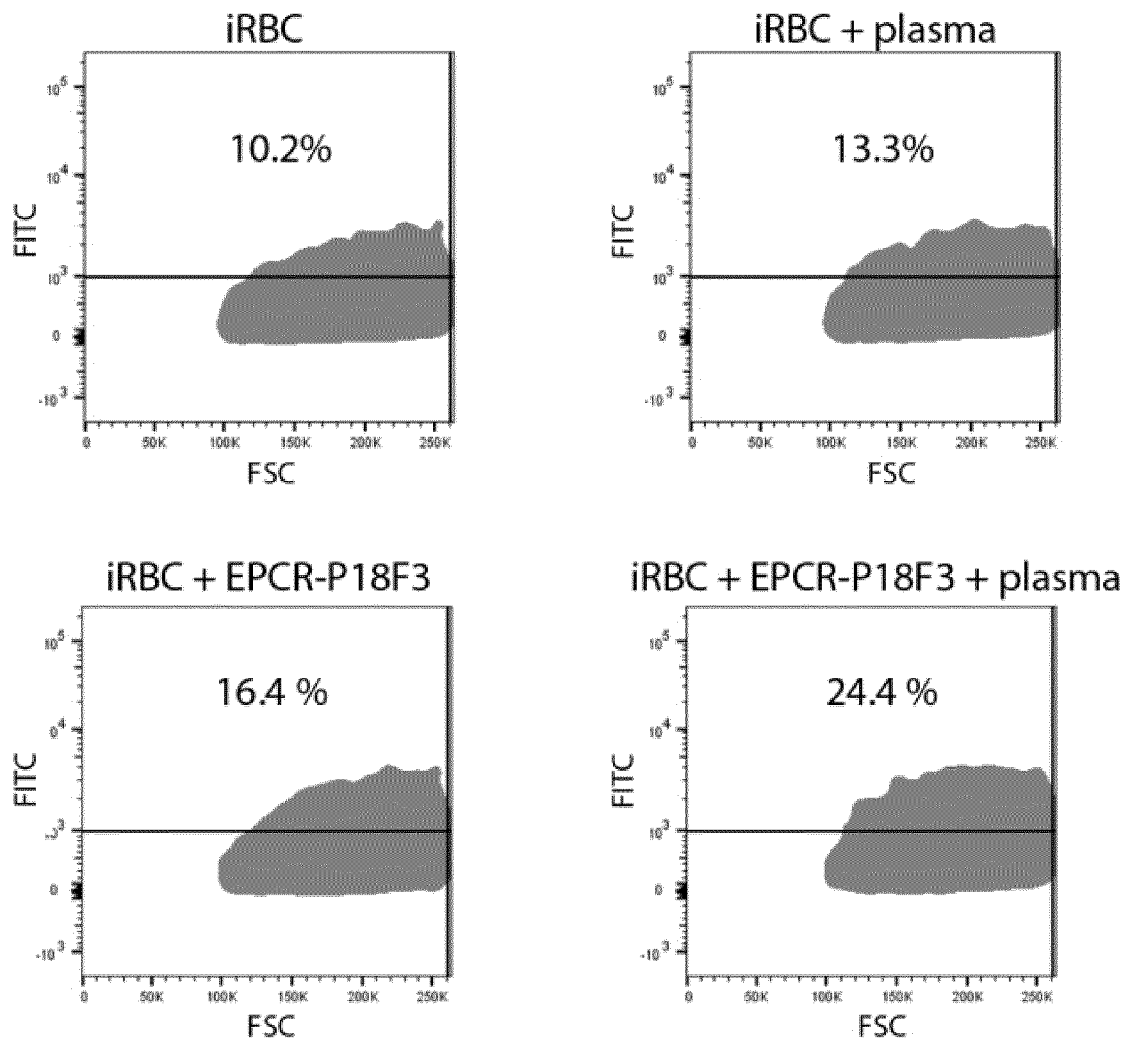
FIG. 18. Opsonic phagocytosis mediated by EPCR-P18F3. In order to demonstrate that VAR19-expressing infected erythrocytes (iRBC) opsonization mediated by EPCRP18F3 induces phagocytosis, THP1 derived macrophages were incubated with CFSE-stained VAR19-expressing iRBC pre-opsonized with EPCR-P18F3 and hIgG. After 3 hours, THP1 cells were analysed by flow cytometry. CFSE positive THP1 cells were regarded as cells having phagocyted at least one iRBC.

Phagocytic assays revealed an increased opsonic phagocytosis of erythrocytes by THP1 monocytes upon treatment with $DARC_{VHH}$-EBV P18 and EBV P23 antigen fusions. Indeed, the conjugate $DARC_{VHH}$-EBV P18 (C56S)* mediated an opsonic phagocytosis of FY+ red-blood cells by THP1-derived macrophages (FIG. 9A). Similar observations were made upon treatment with $DARC_{VHH}$-EBV P18F3 (FIG. 9B), and also with the EPCR-P18F3 conjugate (using VAR19-expressing infected erythrocytes) (FIG. 18).

Figure 12:
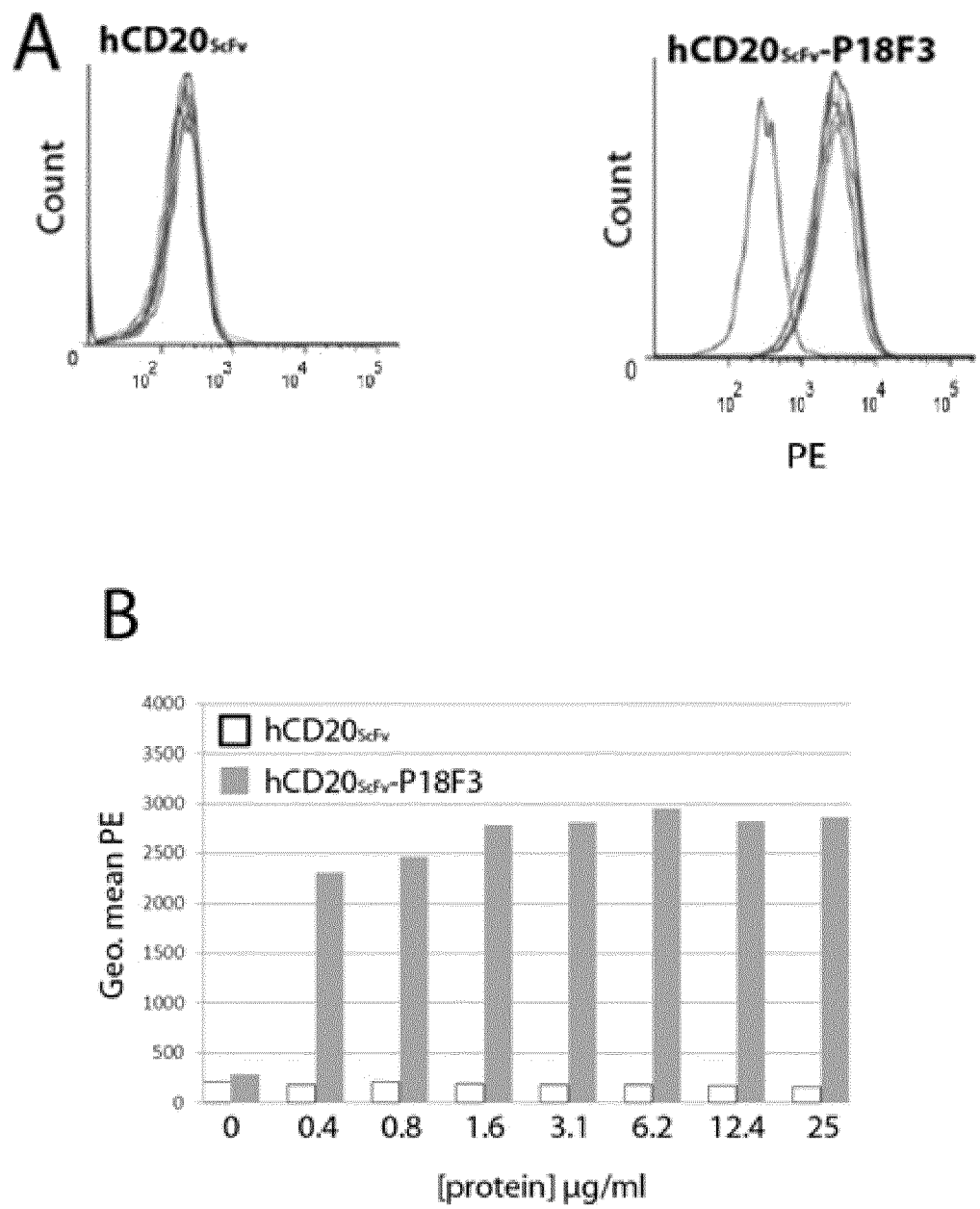
FIG. 12. CD20$^+$ RAJI cells opsonization mediated by the hCD20$_{ScFv}$-P18F3 conjugate. In order to demonstrate B cells opsonization, CD20$^+$ RAJI cells were incubated with serial dilutions of hCD20$_{ScFv}$ or hCD20$_{ScFv}$-P18F3 and subsequently with a constant human plasma dilution (1:100). (A) Membrane associated IgG were detected by flow cytometry using an anti-hIgG PE-conjugated antibody. A shift in fluorescence intensity (PE) reflects the presence of an immune complex at the cell surface. (B) Chart representation of the data generated by flow cytometry analysis.
Figure 13:
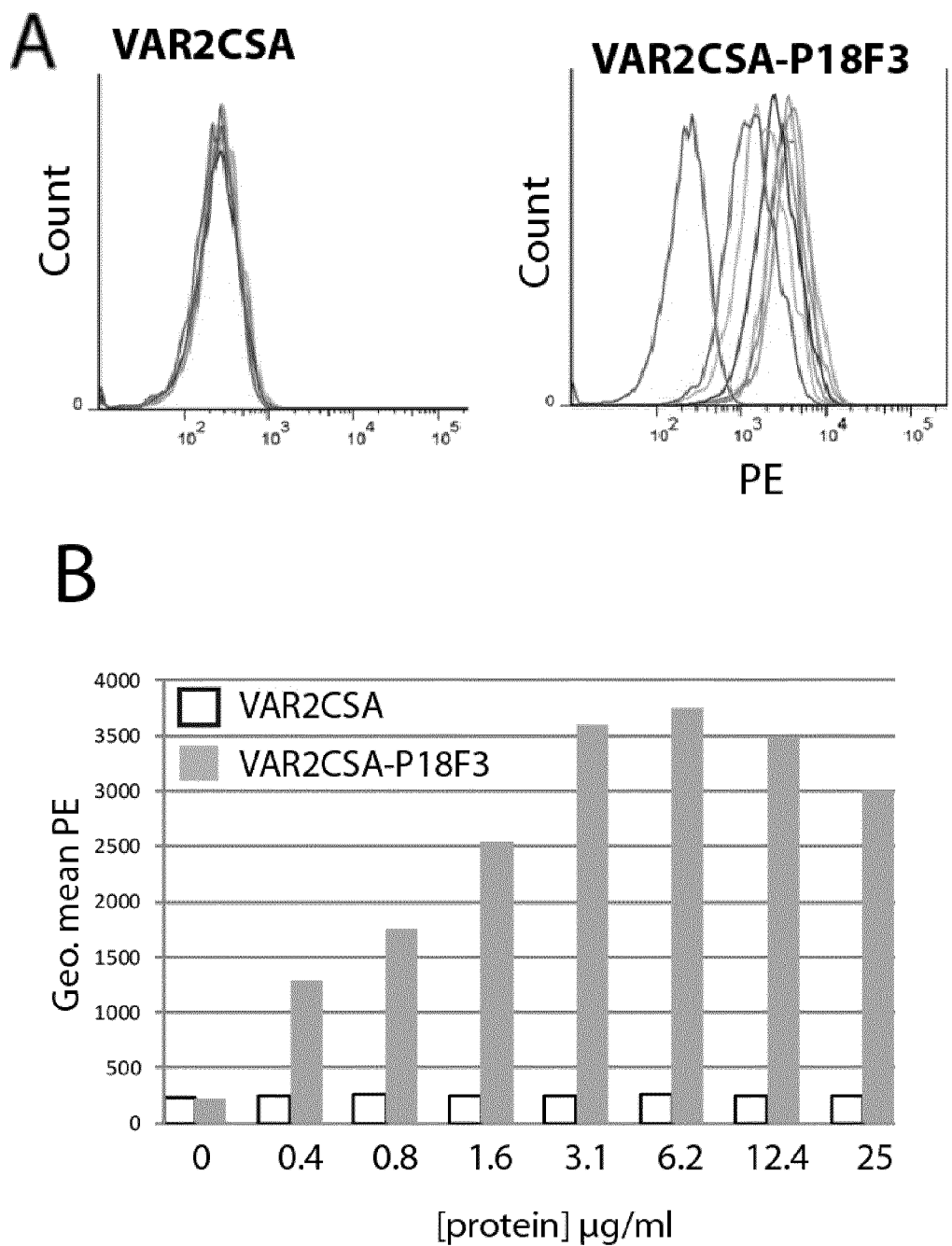
FIG. 13. CSA$^+$ RAJI cells opsonization mediated by the VAR2CSA-P18F3 conjugate. In order to demonstrate B cells opsonization, CSA$^+$ RAJI cells were incubated with serial dilutions of VAR2CSA or VAR2CSA-P18F3 and subsequently with a constant human plasma dilution (1:100). (A) Membrane associated IgG were detected by flow cytometry using an anti-hIgG PE-conjugated antibody. A shift in fluorescence intensity (PE) reflects the presence of an immune complex at the cell surface. (B) Chart representation of the data generated by flow cytometry analysis.

Incubation of cell-bound $hCD20_{ScFv}$-P18F3 and VAR2CSA-P18F3 conjugates with plasma samples of EBV+ donors also led to RAJI opsonization, i.e. coating of cells with the donor plasma IgG (FIGS. 12 and 13).

Figure 9:
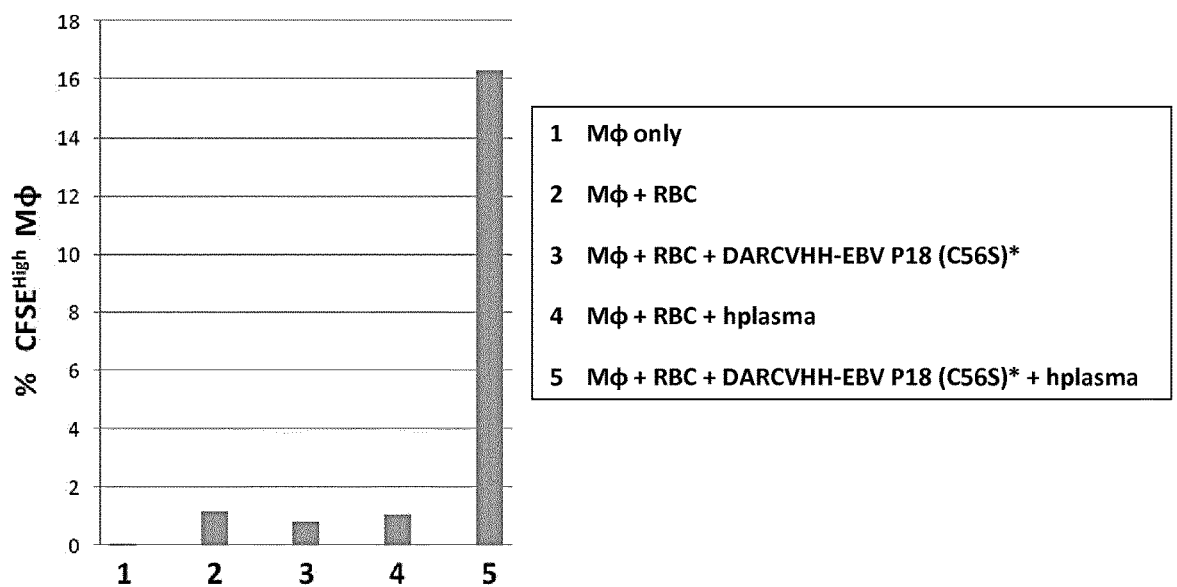
FIG. 9. Opsonic phagocytosis mediated by DARC$_{VHH}$-EBV P18 conjugates (mutated and fragments). (A) In order to demonstrate that erythrocytes opsonization leads to phagocytosis, THP1 derived macrophages were incubated with CFSE-stained DARC$^+$ erythrocytes pre-opsonized with DARC$_{VHH}$-P18(C56S)*, and human IgG. After 3 hours, THP1 cells were analysed by flow cytometry. CFSE positive THP1 cells were regarded as cells having phagocyted at least one erythrocyte. (B) THP1 cells were incubated with CFSE-stained DARC$^+$ erythrocytes pre-opsonized with DARC$_{VHH}$-P18F3 and human IgG. After 3 hours, THP1 cells were analysed by flow cytometry. CFSE positive THP1 cells were regarded as cells having phagocyted at least one erythrocyte. (C) Opsonic phagocytosis mediated by DARC$_{VHH}$-EBV P18 conjugates. In order to demonstrate that treatment of DARC+ erythrocytes with different DARC$_{VHH}$-EBV P18 conjugates mediates cell opsonization and subsequent phagocytosis by THP1 cells, CFSE-stained erythrocytes were incubated with equimolar concentrations (10 nM) of DARC$_{VHH}$, DARC$_{VHH}$-EBV P18F2, DARC$_{VHH}$-EBV P18F3, DARC$_{VHH}$-EBV P18F4 and with 10% human plasma. Human plasma samples were screened for their reactivity to P18 and pooled according to their capability to recognize the EBV antigens in 3 groups: highly reactive to P18 (High), moderately reactive to P18 (Medium) or low reactive (Low). After 3 h co-incubation, THP1 cells were analysed by flow cytometry. CFSE positive THP1 cells were regarded as cells having phagocyted at least one erythrocyte. Results are expressed as fold increase compared to the experimental condition without any conjugate, red blood cells (RBC) only.
Figure 9:
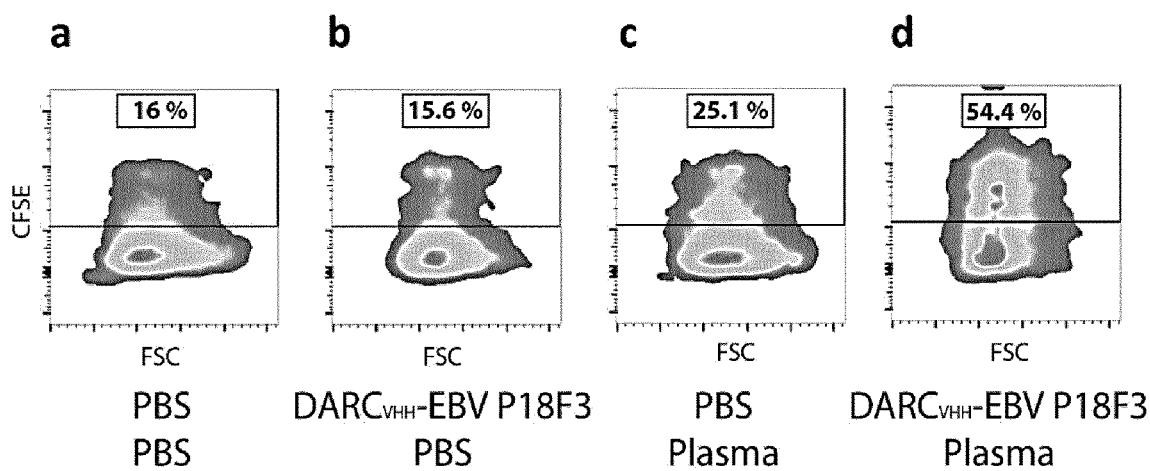
Figure 9C:
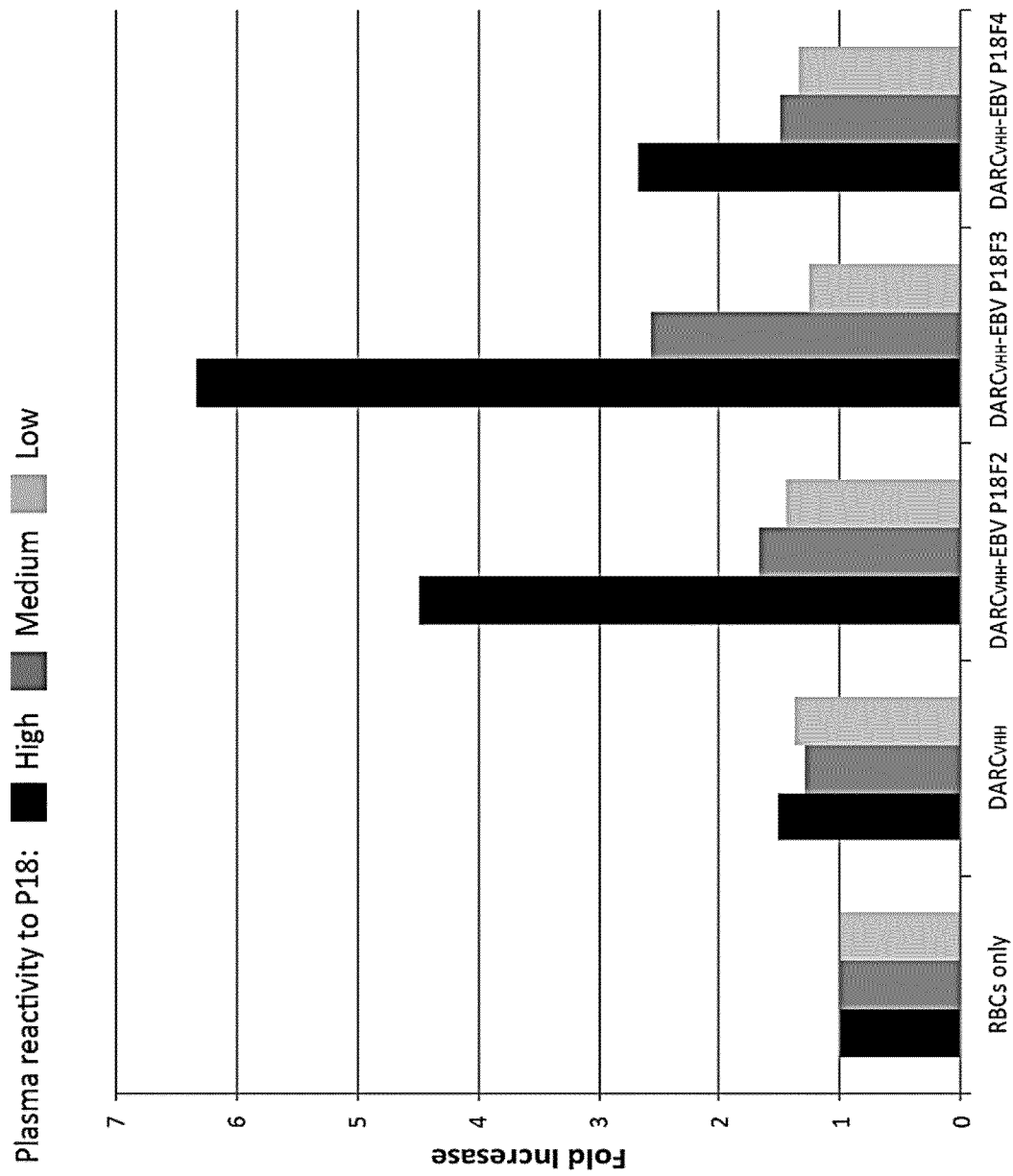

Interestingly, treatment of FY+ red-blood cells with $DARC_{VHH}$ fused to different EBV P18 fragments revealed a link between the capability of said fragments to recruit IgG and the intensity of the elicited cellular response (FIG. 9C). Notably, the results of FIG. 9C show (i) a correlation between the cellular response (phagocytosis) and the antibody titers (anti-P18) from the plasmas used for opsonisation, and (ii) a plasma reactivity to P18 differing between the different P18 fragments, the P18F3 antigen displaying a better response.

These results are the first promising in vitro data demonstrating that immune clearance of a define target cell can be achieved following treatment with binding moeity-EBV P18 or EBV P23 fusion proteins.

2.6. Complement Activation

Figure 14:
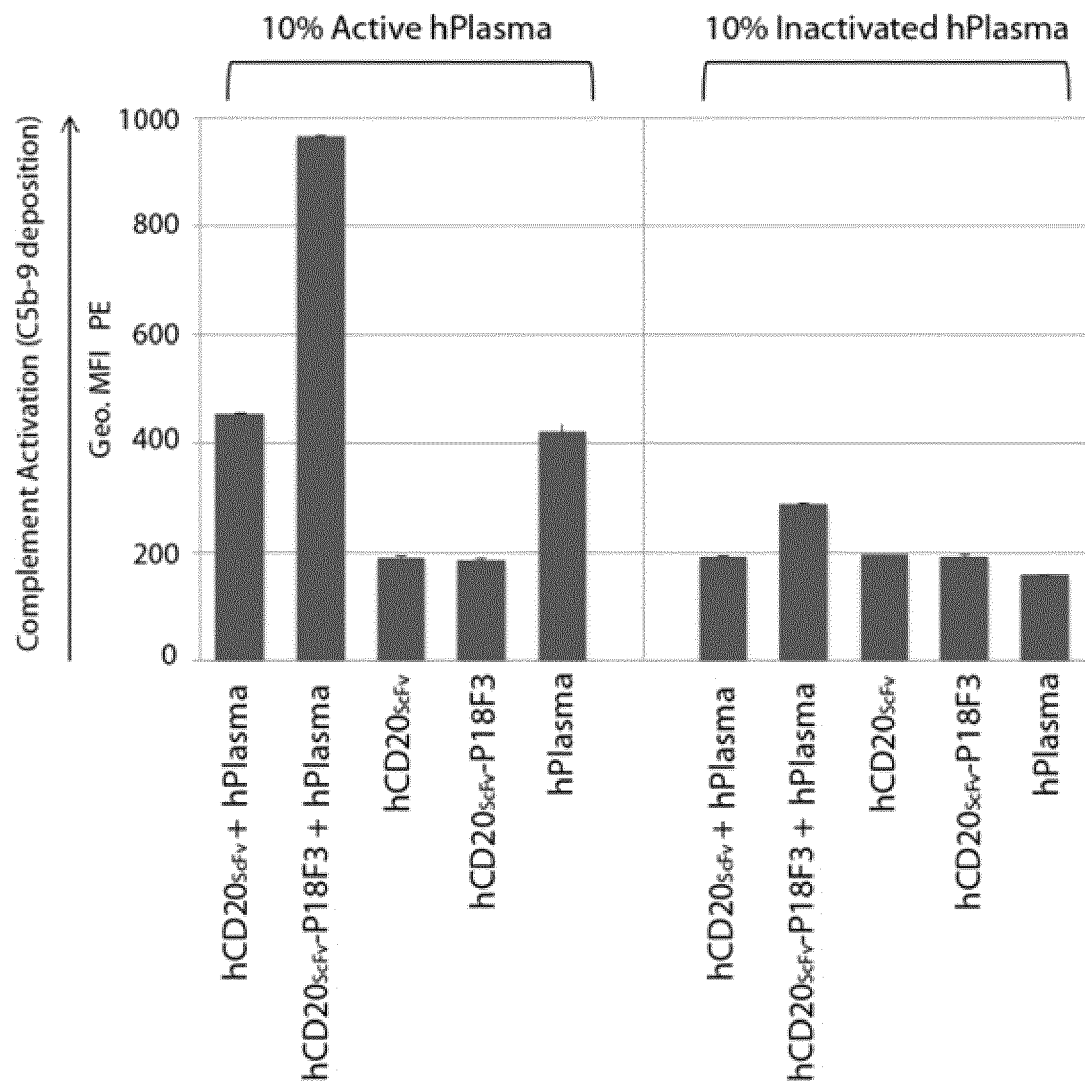
FIG. 14. Complement activation mediated by hCD20$_{ScFv}$-P18F3. In order to demonstrate that B cell opsonization mediated by hCD20$_{ScFv}$-P18F3 is able to activate the complement cascade to the formation of the membrane-attack complex, CD20$^+$ RAJI cells were incubated with 5 µg/ml of hCD20$_{ScFv}$ or hCD20$_{ScFv}$-P18F3 and subsequently with 10% EBV$^+$ human plasma in its active form or heat inactivated. The deposition of the membrane-attack complex constitutive element C5-b9 was detected at the cell membrane surface after 1 h incubation using a mouse monoclonal anti-C5-b9 antibody and an anti-mouseIgG-PE-conjugated antibody. The slight C5-b9 deposition at the RAJI cell surface observed with active human plasma alone is most likely due to the activation of the alternative (antibody independent) pathway of the complement by the cancer cell line.

Complement activation assays revealed an increased activation of the complement cascade upon treatment with the $hCD20_{ScFv-P}18F3$ conjugate, most likely the classical antibody dependent pathway. This is illustrated by the formation of the membrane-attack complex at the cell surface that will result in target cell lysis (FIG. 14).

2.7. ADCC

Figure 15:
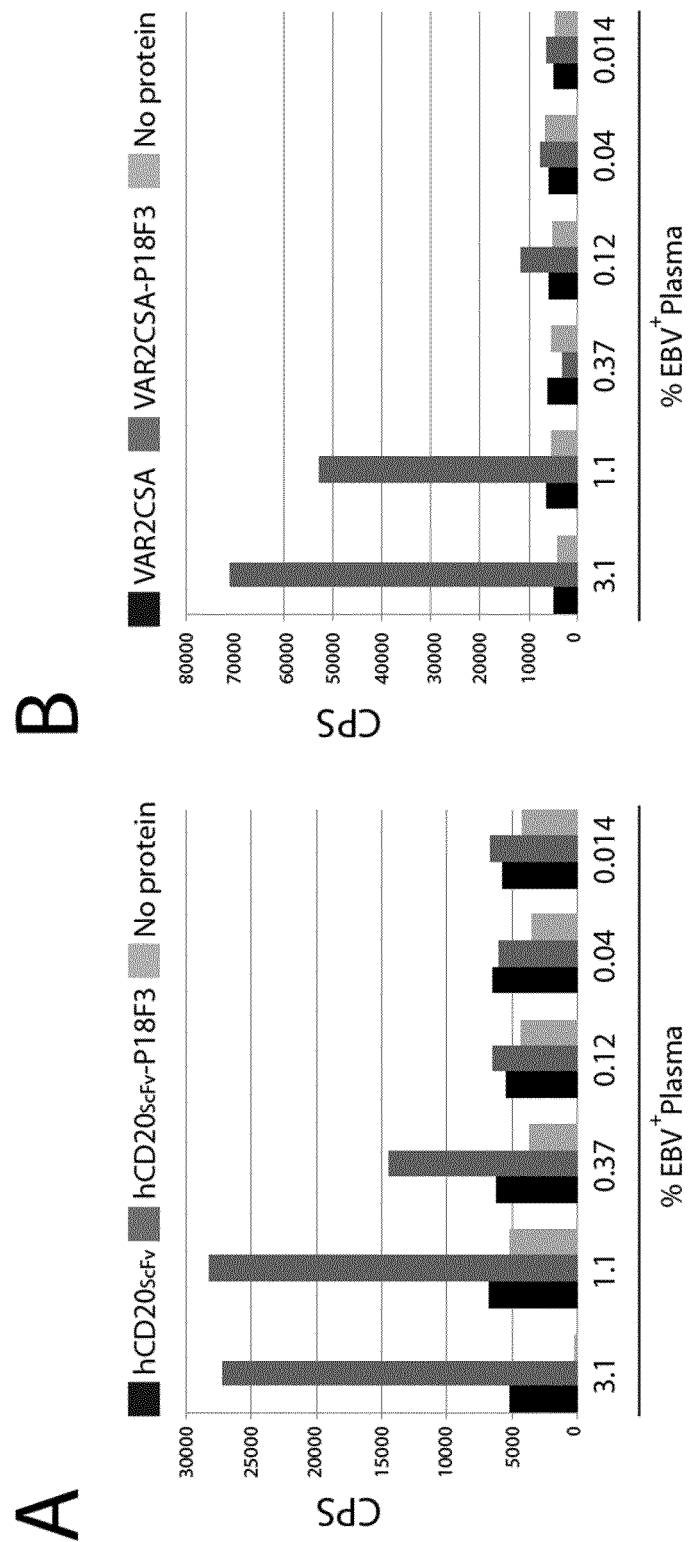
FIG. 15. Antibody Dependent Cell Cytotoxicity (ADCC) mediated by hCD20$_{ScFv}$-P18F3 (A) and VAR2CSA-P18F3 (B). Activation of gene transcription through the NFAT pathway in the effector cells reflects the conjugates biological activity in ADCC and is quantified through the luciferase produced (luminescence readout). RAJI cells were incubated with saturating concentration of conjugates and subsequently with serial dilution of EBV$^+$ human plasma. After a 6 h co-incubation with competent effector cells, NFAT pathway activation was monitored by reading the luminescence of each plate well (expressed in CPS: counts per seconds).

The ADCC assays revealed an increased activation of the NFAT pathway in competent effector cells by target cells (RAJI) pre-treated with either $hCD20_{ScFv-P}18F3$ or VAR2CSA-P18F3. This reflects that opsonization of target cells occurring in presence of EBV+ plasma is leading to engagement of surface Fc receptors on effector cells and subsequent activation of intracellular pathways that will ultimately lead to target cell lysis (FIG. 15).

3. Conclusion

Immunotherapies are being used against cancer cells, infectious diseases as well as Alzheimer's disease. Interestingly, a recent study has shown that macrophages eliminate circulating tumor cells after monoclonal antibody therapy through dependent FcγRI and FcγRIV phagocytosis. No cell mediated Fc effector function are driven by "antibody fragment" or "antibody-binding fragment" or alternative "proteic and non-proteic" moieties including, without limitation, Fab antibodies, Fab' antibodies, F(ab')2 antibodies, Fv antibodies, scFv antibodies, camelid single domain antibodies (VHH), and shark single domain antibodies (VNAR). One possibility is to fuse an Fc chain to those targeting moieties. However, adding an Fc chain will result in recombinant expression difficulties as well as decrease accessibility to epitopes present in small cavities and clefts.

The present invention proposes to overcome these issues with a new and innovative immunogenic construct, which is capable to redirect an EBV-existing (or pre-existing) immune response towards an undesired target cell and/or microorganism. In order to provide the proof of concept that a targeting moiety fused to an EBV antigen is capable to promote opsonization of a defined target, and the formation of immune complexes and subsequent clearance of said target, three in vitro models were used herein. In the first model, a single domain antibody ($DARC_{VHH}$) targeting a protein expressed at the surface of erythrocytes was conjugated to a couple of different EBV antigens (either EBV P18 or EBV P23). In a second model, a single domain antibody ($VAR2CSA_{VHH}$) and a proteic binding moiety not derived from antibodies (EPCR), both targeting malarial proteins expressed at the surface of Plasmodium falciparum infected erythrocytes ($VAR2CSA^{PfEMP1}$ and $VAR19^{PfEMP1}$, respectively) were conjugated to EBV P18. In a third model, an scFv antibody ($hCD20_{ScFv}$) directed towards the Cluster of Differentiation CD20 and a proteic binding moiety not derived from antibodies (VAR2CSA), targeting respectively the CD20 molecules present at the surface of B cells (including B lymphomas) or the CSA over-expressed at the surface of cancer cells were conjugated to EBV P18.

The present study demonstrates the capacity of the designed conjugates to opsonize the target cells, respectively erythrocytes, *Plasmodium falciparum* infected erythrocytes, cancer cells and promote their clearance by immune effector mechanisms namely opsonic phagocytosis, ADCC and CDC.

The N-terminal regions of EBV P18 and EBV P23 were identified as an obstacle for protein expression, which considerably decreased protein solubility and stability. The deletion of N-terminal segments of EBV P18 and EBV P23 allowed soluble expression and purification of the conjugates (FIG. 1-4). The presence of a protein linker between the VHH and the EBV antigens was not mandatory for correct protein production.

Importantly, surface plasmon resonance experiments showed that the affinity and specificity of the binding moieties (DARC$_{VHH}$ and VAR2CSA$_{VHH}$) for their defined targets was not affected by their fusion to an EBV-antigen (FIG. 5).

Figure 6B:
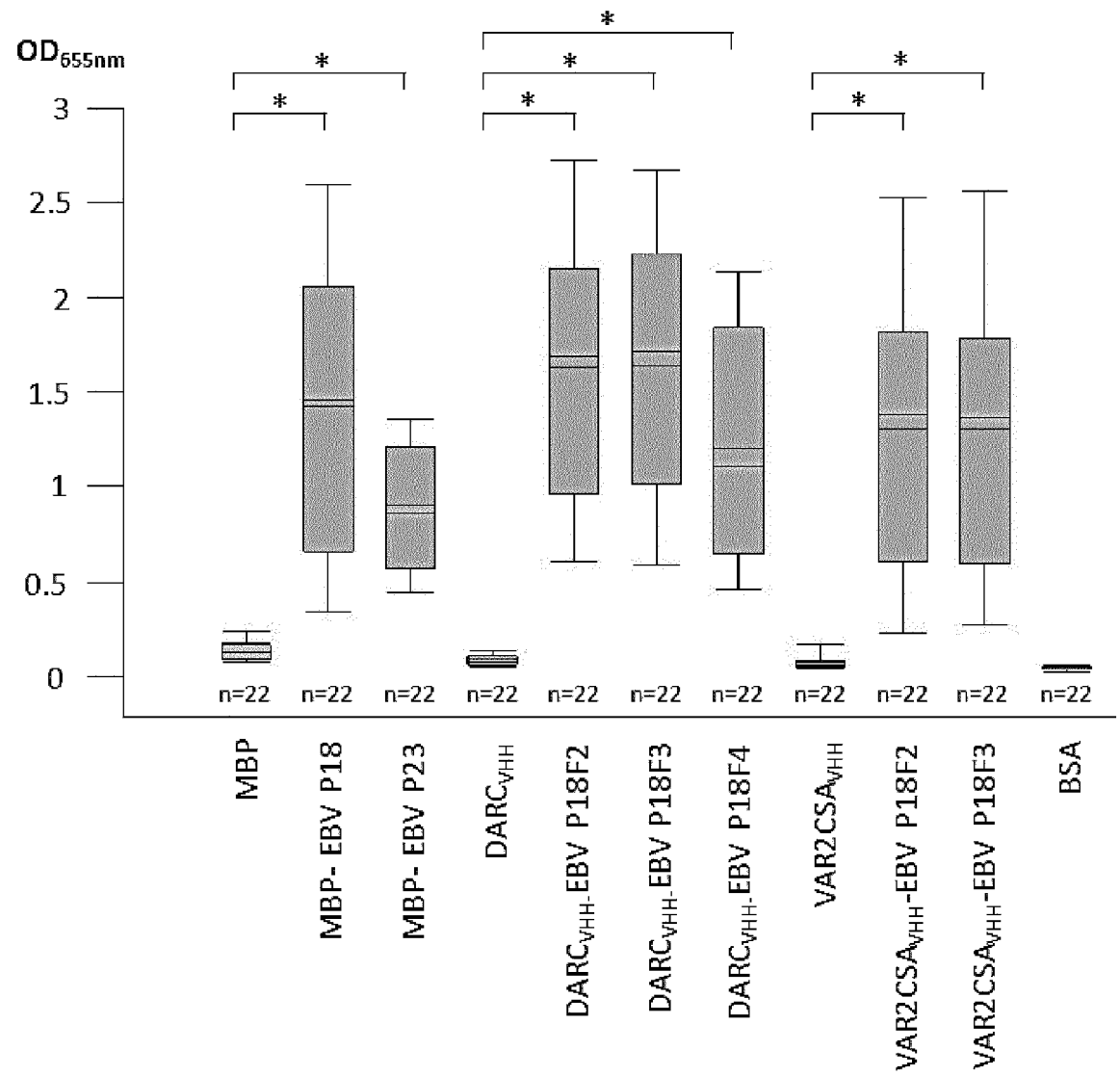

Immune recognition experiments performed with plasma from EBV positive individuals revealed that the conjugates comprising either EBV P18 or EBV P23 were highly recognized by circulating IgG (FIG. 6). Although F4 was still efficient to recruit IgG, the conjugates comprising the EBV P18 fragment EBV P18F3 (8.4 kDa) appeared to be the shortest fragment of EBV P18 giving maximum IgG reactivity. EBV P18F3 appeared as an adequate EBV antigen to be fused to diverse binding moieties and would allow the recruitment a variety of immune effectors to the target site. This was further confirmed by i) aggregation assays in which DARC$_{VHH}$-EBV P18F3 was showed to mediate aggregation of erythrocytes in the presence of EBV+ human plasma (FIG. 8) and ii) by opsonization assays in which EPCR-EBV P18F3, hCD20$_{ScFv-EBV}$ P18F3 and VAR2CSA-EBV P18F3 were shown to recruit plasma IgG to the surface of infected erythrocytes (for EPCR-EBV P18F3) and to the surface of RAJI cancer cells (for hCD20$_{ScFv-EBV}$ P18F3 and VAR2CSA-EBV P18F3) thus leading to the formation of immune complexes (FIGS. 12, 13 and 17).

Of major interest, the formation of immune complexes mediated by the conjugates led to immune effector responses. DARC$_{VHH}$-EBV P18F3 treatment of DARC+ erythrocytes promoted their elimination by macrophages (FIG. 9). In line with the results of EBV fragments immune recognition, DARC$_{VHH}$-EBV P18F3 was more potent to induce opsonic phagocytosis than DARC$_{VHH}$-EBV P18F4 (FIG. 9).

Furthermore, treatments of target cells with P18F3 conjugates also led to i) ADCC by competent effector cells (FIG. 15) and ii) activation of the complement cascade (FIG. 15) and formation of a MAC (membrane-attack complex) at the surface of the target cell.

Taken together, these results demonstrate that immunogenic constructs, such as DARC$_{VHH}$-EBV P18F3, EPCR-EBV P18F3, hCD20$_{ScFv}$-EBV P18F3 and VAR2CSA-EBV P18F3 are able to redirect an existing EBV immune response towards a specific target sequentially leading to the formation of immune complexes and subsequent recruitment of immune effector mechanisms such as opsonic phagocytosis, ADCC and CDC which ultimately lead to target elimination.

The types of agents, stable, easy to produce and highly efficient at opsonizing a target element are extremely valuable for clinical interventions either alone or in combination with existing therapies to fight pathogens and cancers.

REFERENCES

Aird W C, Mosnier L O, and Fairhurst R M (2014). Blood; 123(2): 163-167.

Birch C M, Hou H W, Han J, Niles J C (2015). Sci Rep.; 5:11347.

Chan C L, Renia L, and Tan K S (2012). PLoS One; 7(6):e38523.

Chen X, Zaro J L, Shen W C (2013). Adv Drug Deliv Rev; 65(10):1357-1369.

Clausen T M, Christoffersen S, Dahlback M, Langkilde A E, Jensen K E, Resende M, Agerbk MØ, Andersen D, Berisha B, Ditlev S B, Pinto V V, Nielsen M A, Theander T G, Larsen S, and Salanti A (2012). J Biol Chem.; 287(28):23332-45.

Conrath K, Vincke C, Stijlemans B, Schymkowitz J, Decanniere K, Wyns L, Muyldermans S, and Loris R (2005).

Estevez M C, Huang YF, Kang H, O'Donoghue M B, Bamrungsap S, Yan J, Chen X, Tan W (2010). Methods Mol Biol; 624:235-248. J. Mol. Biol.; 350: 112-125.

Eudes R, Le Tuan K, Delettre J, Mornon J P, Callebaut I (2007). BMC Struct Biol; 7:2.

Harboe M, Thorgersen E B, and Mollnes T E (2011). Adv Drug Deliv Rev; 63(12):976-987.

Hu W, Li F, Yang X, Li Z, Xia H, et al. (2004). J Biotechnol; 107: 83-90.

Jiang X R, Song A, Bergelson S, Arroll T, Parekh B, May K, Chung S, Strouse R, Mire-Sluis A, and Schenerman M (2011). Nat Rev Drug Discov; 10(2):101-111.

Liu A Y, Robinson R R, Murray E D Jr, Ledbetter J A, Hellstrom I, and Hellstrom K E (1987). J Immunol.; 139(10):3521-6.

Nunes-Silva S, Gangnard S, Vidal M, Vuchelen A, Dechavanne S, Chan S, Pardon E, Steyaert J, Ramboarina S, Chene A et al. (2014). Sci Rep; 4:7373.

Olafsen T, Betting D, Kenanova V E, Salazar F B, Clarke P, Said J, Raubitschek A A, Timmerman J M, and Wu A M (2009). J Nucl Med.; 50(9):1500-8.

Otz T, Grosse-Hovest L, Hofmann M, Rammensee H G, and Jung G. Leukemia; 23(1):71-7.

Skrlec K, Strukelj B, and Berlec A (2015). Trends in Biotechnology; 33(7): 408-418.

Smolarek D, Hattab C, Hassanzadeh-Ghassabeh G, Cochet S, Gutierrez C, de Brevern A G, Udomsangpetch R, Picot J, Grodecka M, Wasniowska K, Muyldermans S, Colin Y, Le Van Kim C, Czerwinski M, and Bertrand O (2010). Cell Mol Life Sci.; 67(19):3371-87.

Srivastava A1, Gangnard S, Dechavanne S, Amirat F, Lewit Bentley A, Bentley G A, and Gamain B (2011). PLoS One.;6(5):e20270.

Stoltenburg R, Reinemann C, and Strehlitz B (2007). Biomol Eng.; 24(4):381-403.

Zwicke G L, Mansoori G A, and Jeffery C J (2012). Nano Rev, 3: 18496.

Wu J, Nantz M H, and Zern M A (2012). Front Biosci; 7:d717-725.

Vogt A M, Barragan A, Chen Q, Kironde F, Spillmann D, and Wahlgren M (2003). Blood; 101(6):2405-2411.

The invention claimed is:

1. An immunogenic conjugate comprising:
an Epstein-Barr Virus (EBV) B-cell antigen,
wherein the EBV B-cell antigen is a P18 or a P23 antigen or a functional fragment or variant thereof,
wherein the P18 antigen or functional fragment or variant thereof comprises an amino acid sequence selected from the group consisting of SEQ ID NOs: 15, 17-22, 39, 41, 43-49, 52-58, 75, and 76; and
wherein the P23 antigen or functional fragment or variant thereof comprises an amino acid sequence selected from the group consisting of SEQ ID NOs: 16, 23-38, 40, 42, 50, 51, 59, and 60;
covalently coupled with a moiety binding to a target cell and/or microorganism,
wherein said moiety is a ligand binding protein selected from the group consisting of antibody fragments devoid of Fc, antibody mimetics, cell surface receptors, cell surface ligands, non-proteic moieties, and any combination thereof, and
wherein said antibody fragment devoid of Fc is selected from the group consisting of Fab, Fab', F(ab')2, Fv, single chain variable binding fragment (scFv), single-domain binding fragment (VHH), and any combination thereof.

2. The immunogenic conjugate according to claim 1, wherein said non-proteic moiety is selected from the group consisting of vitamins, carbohydrates, glycosaminoglycans, small nucleic acids, small chemical compounds, and any combination thereof.

3. The immunogenic conjugate according to claim 1, wherein the P18 antigen or functional fragment or variant thereof comprises the amino acid sequence of SEQ ID NO:15 and the P23 antigen or functional fragment or variant thereof comprises the amino acid sequence of SEQ ID NO:16.

4. The immunogenic conjugate according to claim 1, with the proviso that, when said moiety comprises a thiol group, the P18 and/or P23 antigens, functional fragments, or variants thereof do not comprise any cysteine residue.

5. The immunogenic conjugate according to claim 4, wherein or functional fragment or variant thereof comprises the amino acid sequence of SEQ ID NO:39 and the P23 antigen or functional fragment or variant thereof comprises the amino acid sequence of SEQ ID NO:40.

6. The immunogenic conjugate according to claim 1, wherein the P18 antigen or functional fragment or variant thereof comprises an amino acid sequence selected from the group consisting of SEQ ID NO:75 and SEQ ID NO:43 to SEQ ID NO:49and the P23 antigen or functional fragment or variant thereof comprises an amino acid sequence selected from the group consisting of SEQ ID NO:50 and SEQ ID NO:51.

7. The immunogenic conjugate according to claim 1, wherein the P18 antigen or functional fragment or variant thereof comprises an amino acid sequence selected from the group consisting of SEQ ID N0:76 and SEQ ID NO:52 to SEQ ID NO:58 and the P23 antigen or functional fragment or variant thereof comprises an amino acid sequence selected from the group consisting of SEQ ID NO:59 and SEQ ID NO:60.

8. The immunogenic conjugate according to claim 1, wherein the target cell is a diseased cell and/or the target microorganism is a pathogenic microorganism.

9. The immunogenic conjugate according to claim 8, wherein:
said diseased cell is a malaria infected erythrocyte and/or said pathogenic microorganism is *Plasmodium falciparum*; or
said diseased cell is a cancer cell or a cell infected by a pathogen; or
said pathogenic microorganism is an extracellular pathogen.

10. A pharmaceutical composition comprising at least one immunogenic conjugate according to claim 1 and at least one pharmaceutically acceptable excipient.

11. A method for treating cancer, viral infection, bacterial infection, fungal infection, and/or parasitic disease in a subject in need thereof, comprising administering the immunogenic conjugate of claim 1 to said subject.

12. The immunogenic conjugate according to claim 9, wherein said pathogen is a virus, a bacterium, a fungus, and/or a parasite.

13. The immunogenic conjugate according to claim 8, wherein said pathogenic microorganism is a virus, a bacterium, a fungus, and/or a parasite.

14. The immunogenic conjugate according to claim 1, wherein the P18 antigen or functional fragment or variant thereof comprises an amino acid sequence selected from the group consisting of SEQ ID NO:17 to SEQ ID NO:22 and the P23 antigen or functional fragment or variant thereof comprises an amino acid sequence selected from the group consisting of SEQ ID NO:23 to SEQ ID NO:38.

15. The pharmaceutical composition according to claim 10, wherein the P18 antigen or functional fragment or variant thereof comprises the amino acid sequence of SEQ ID NO:15 and the P23 antigen or functional fragment or variant thereof comprises the amino acid sequence of SEQ ID NO:16.

16. The pharmaceutical composition according to claim 10, wherein
the P18 antigen or functional fragment or variant thereof comprises an amino acid sequence selected from the group consisting of SEQ ID NO:17 to SEQ ID NO:22 and the P23 antigen or functional fragment or variant thereof comprises an amino acid sequence selected from the group consisting of SEQ ID NO:23 to SEQ ID NO:38, or
the P18 antigen or functional fragment or variant thereof comprises the amino acid sequence of SEQ ID NO:39 and the P23 antigen or functional fragment or variant thereof comprises the amino acid sequence of SEQ ID NO:40, or
the P18 antigen or functional fragment or variant thereof comprises an amino acid sequence selected from the group consisting of SEQ ID NO:75 and SEQ ID NO:43 to SEQ ID NO:49 and the P23 antigen or functional fragment or variant thereof comprises an amino acid sequence selected from the group consisting of SEQ ID NO:50 and SEQ ID NO:51, or
the P18 antigen or functional fragment or variant thereof comprises an amino acid sequence selected from the group consisting of SEQ ID NO:76 and SEQ ID NO:52 to SEQ ID NO:58 and the P23 antigen or functional fragment or variant thereof comprises an amino acid sequence selected from the group consisting of SEQ ID NO:59 and SEQ ID NO:60.

* * * * *